United States Patent [19]

Möhring et al.

[11] Patent Number: 4,684,728

[45] Date of Patent: Aug. 4, 1987

[54] SOLUBILIZING BIOLOGICALLY ACTIVE COMPOUNDS WITH REACTIVE HYDROGEN ATOMS

[75] Inventors: Edgar Möhring, Berg.-Gladbach; Hanns P. Müller, Odenthal; Peter Roessler, Berg.-Gladbach; Kuno Wagner; Helmut Tietz, both of Leverkusen, all of Fed. Rep. of Germany

[73] Assignee: Bayer Aktiengesellschaft, Leverkusen, Fed. Rep. of Germany

[21] Appl. No.: 107,976

[22] Filed: Dec. 28, 1979

[30] Foreign Application Priority Data

Jan. 12, 1979 [DE] Fed. Rep. of Germany ....... 2901060
Mar. 16, 1979 [DE] Fed. Rep. of Germany ....... 2910356

[51] Int. Cl.$^4$ ................. C07D 253/00; C07D 251/00; C07D 273/04; C07D 265/00
[52] U.S. Cl. .................... 544/182; 544/223; 544/67; 544/276; 544/63; 544/53; 548/163; 548/375; 560/34; 560/159; 549/51; 549/469; 549/285; 549/417; 549/494; 546/69; 546/316; 536/23; 536/55; 540/334; 558/171
[58] Field of Search ....... 544/223, 220, 182; 564/60

[56] References Cited

U.S. PATENT DOCUMENTS 2,857,261 10/1958 Kosmin ........................... 544/223
4,039,576 8/1977 Merz et al. ...................... 564/60
4,154,724 5/1979 Schulze .......................... 564/60
4,174,392 11/1979 Mohring et al. .................. 544/223
4,178,427 12/1979 Waddill et al. ................... 564/60

OTHER PUBLICATIONS

Condensed Chemical Dictionary, 9th ed. (1977).

Primary Examiner—Henry R. Jiles
Assistant Examiner—Robert C. Whittenbaugh
Attorney, Agent, or Firm—Sprung, Horn Kramer & Woods

[57] ABSTRACT

A biologically active compound can be solubilized by reaction in different sequences to form a derivative carrying the active moiety, a linking group such as an optionally substituted diisocyanate radical, a polyether moiety such as a polyoxyethylene radical, and a terminal group such as a butyl radical, e.g.

$$H_9C_4O+(CH_2)_2O\xrightarrow{}_{\overline{n}}CNH(CH_2)_4-$$

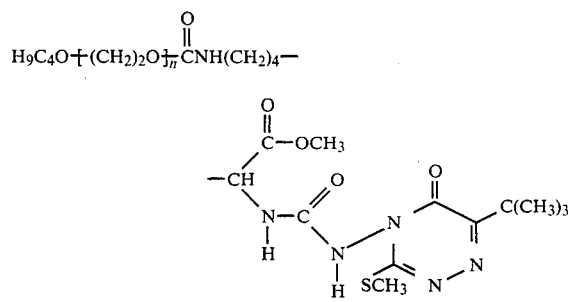

n=1 to 400. The active materials can be agricultural chemicals, pharmaceuticals, and the like.

12 Claims, No Drawings

SOLUBILIZING BIOLOGICALLY ACTIVE COMPOUNDS WITH REACTIVE HYDROGEN ATOMS

The present invention relates to a new process for improving the solubility in water and/or lower aliphatic alcohols of active compounds that have a biological action and have at least one hydrogen atom that is active in Zerewitinoff reactions and to new compounds that can be prepared by this process.

By the expression "active compounds that have a biological action" there are to be understood organic chemical compounds which are active in the field of plant protection and in human medicine and veterinary medicine. Many of these active compounds are sparingly soluble in water and in lower aliphatic alcohols. They can thus be used in the liquid form only with the aid of solubilizing agents. In order to reduce as far as possible the use of such auxiliary agents in the use forms of the active compounds that have a biological action, it is desirable to improve the solubility in water or lower aliphatic alcohols of these active compounds.

The present invention now provides compounds that are characterized in that they can be prepared by a process in which (a) an active compound that has a biological action and has at least one hydrogen atom that is active in Zerewitinoff reactions is reacted, in a molar ratio of 1:1, with a compound that is obtained by reacting a hydrophilic polyether containing one OH, NH or $NH_2$ group and having a water absorption capacity of at least about 15%, relative to the weight of the polyether, with an organic compound having at least two groups that are reactive towards hydrogen atoms that are active in Zerewitinoff reactions, in the ratio of the number of the OH, NH or $NH_2$ equivalents of the polyether to the number of the equivalents of groups, in the organic compound with at least two groups that are reactive towards hydrogen atoms that are active in Zerewitinoff reactions, that are reactive towards hydrogen atoms that are active in Zerewitinoff reactions, that is to say $(m-1):m$ (m being the number of groups that are reactive towards hydrogen atoms that are active in Zerewitinoff reactions), or in which (b) an active compound that has a biological action and has at least one hydrogen atom that is active in Zerewitinoff reactions is reacted, in a molar ratio of 1:1, with a compound that has m groups that are reactive towards hydrogen atoms that are active in Zerewitinoff reactions, m being at least 2, and the resulting compound is then reacted with a hydrophilic polyether containing one OH, NH or $NH_2$ group and having a water absorption capacity of at least 15%, relative to the weight of the polyether, in an equivalent ratio of $m:(m-1)$, or in which (c) an active compound that has a biological action and has at least one hydrogen atom that is active in Zerewitinoff reactions, a compound with m groups that are reactive towards hydrogen atoms that are active in Zerewitinoff reactions, m being at least 2, and a hydrophilic polyether containing one OH, NH or $NH_2$ group and having a water absorption capacity of at least 15%, relative to the weight of the polyether, are reacted in an equivalent ratio of $1:m:(m-1)$.

The present invention also provides a process for improving the solubility in water and/or lower aliphatic alcohols of an active compound that has a biological action and has at leat one hydrogen atom that is active in Zerewitinoff reactions, in which process (a) an active compound that has a biological action and has at least one hydrogen atom that is active in Zerewitinoff reactions is reacted, in a molar ratio of 1:1, with a compound which is obtained by reacting a hydrophilic polyether containing one OH, NH or $NH_2$ group and having a water absorption capacity of at least 15%, relative to the weight of the polyether, with a compound having at least two groups that are reactive towards hydrogen atoms that are active in Zerewitinoff reactions, in the ratio of the number of the OH, NH or $NH_2$ equivalents of the polyether to the number of the equivalents of groups, in the organic compound with at least two groups that are reactive towards hydrogen atoms that are active in Zerewitinoff reactions, that are reactive towards hydrogen atoms that are active in Zerewitinoff reactions, that is to say $(m-1):m$ (m being the number of groups that are reactive towards hydrogen atoms that are active in Zerewitinoff reactions), or (b) an active compound that has a biological action and has at least one hydrogen atom that is active in Zerewitinoff reactions is reacted, in a molar ratio of 1:1, with a compound that has m groups that are reactive towards hydrogen atoms that are active in Zerewitinoff reactions, m being at least 2, and the resulting compound is then reacted with a hydrophilic polyether containing one OH, NH or $NH_2$ group and having a water absorption capacity of at least 15%, relative to the weight of the polyether, in an equivalent ratio of $m:m-1$, or (c) an active compound that has a biological action and has at least one hydrogen atom that is active in Zerewitinoff reactions, a compound with m groups that are reactive towards hydrogen atoms that are active in Zerewitinoff reactions, m being at least 2, and a hydrophilic polyether containing one OH, NH or $NH_2$ group and having a water absorption capacity of at least 15%, relative to the weight of the polyether, are reacted in an equivalent ratio of $1:m:(m-1)$.

The invention also provides compounds whenever prepared by the foregoing process.

By the expression "hydrogen atom that is active in Zerewitinoff reactions" there is understood a hydrogen atom which is bonded, in an organic compound, to a centre which, compared with a C atom of a hydrocarbon, exerts a powerful electron-withdrawing effect. In the narrower sense, the expression "active in Zerewitinoff reactions" denotes a H atom which is active in the sense of the reaction:

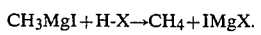

$$CH_3MgI + H\text{-}X \rightarrow CH_4 + IMgX.$$

(see also Beyer Lehrbuch der organischen Chemie (Beyer Textbook of Organic Chemistry) (1968) page 147.)

Surprisingly, compared with the starting active compounds, the compounds according to the present invention have a considerably better solubility in water and lower aliphatic alcohols, the biological activity remaining the same or, in some cases, being improved or extended.

The fact that an active compound obtained by the process according to the invention has an action which is the same as that of the starting active compound, in spite of a modification which changes the molecular weight, can be attributed to the fact that the polyether portion, which is used for rendering the active compound soluble and is bonded to the active compound via the difunctional or polyfunctional coupling member which is reactive towards hydrogen atoms which are active in Zerewitinoff reactions, can be split off again in the animal or vegetable organism. The bond between the coupling member and the active compound is evidently split more easily than the bond between the coupling member and the polyether, which, in the case where a lysine ester diisocyanate is used, can be explained by the different reactivity of the two functional groups.

Possible hydrophilic polyethers containing one OH, NH or $NH_2$ group are in principle all polyethers with a —OH, —NH or —$NH_2$ end group and containing at least two to at most four hundred ethylene oxide units, as well as block copolyethers with additional propylene oxide units. Polyethers of the general formula

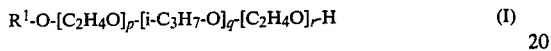
$$R^1\text{-O-}[C_2H_4O]_p\text{-}[i\text{-}C_3H_7\text{-O}]_q\text{-}[C_2H_4O]_r\text{-H} \quad (I)$$

in which
$R^1$ represents a radical of a starter molecule which has a hydrogen atom that is active in the sense of the alkoxylation reaction, and p, q and r each represent 0 or an integer from 1 to 400, provided that at least one of the indices p or r must represent an integer greater than 2, are preferably used.

So that the polyether has a water absorption capacity of at least 15%, relative to the weight of the polyether, the ratio (p+r):q should be about $\geq 0.5$.

Examples of starter molecules which can be used are monohydric alcohols, phenols or secondary amines, preferably methanol, ethanol, 1-propanol, 2-propanol, 1-butanol, 2-butanol, 2-methyl-2-propanol, 1-pentanol, 3-methyl-1-butanol, 2,2-dimethylpropanol, 1-hexanol, 4-methyl-2-pentanol, 2-ethyl-1-butanol, 1-octanol, 2-ethyl-1-hexanol, 1-nonanol, 1-decanol, 1-dodecanol, 1-tetradecanol, 1-hexadecanol, 1-octadecanol, 1,2-diethoxy-2-propanol, cyclohexanol, 2-methylcyclohexanol, 3-methylcyclohexanol, 4-methylcyclohexanol, cyclohexanemethanol, 3,3,5-trimethylcyclohexanol, 4-tert.-butylcyclohexanol, 2-methylphenol, 3-methylphenol, 4-methylphenol, benzyl alcohol, 2-ethylphenol, 1-phenylethanol, 2-phenylethanol, 2,3-dimethylphenol, 3,4-dimethylphenol, 2,6-dimethylphenol, 2,4-dimethylphenol, 3,5-dimethylphenol, 3-phenyl-1-propanol, 2-isopropylphenol, 3-ethyl-5-methylphenol, 2,3,5-trimethylphenol, 2-(1-methylpropyl)-phenol, 2-(1,1-dimethylethyl)-phenol, 4-(1,1-dimethylethyl)-phenol, 3-methyl-5-(1-methylethyl)-phenol, 5-methyl-2-(1-methylethyl)-phenol, 4-methoxyphenol, 4-methoxy-benzyl alcohol, dimethylamine, diethylamine, di-n-propylamine, di-isopropylamine, di-n-butylamine, di-iso-butylamine, bis-(2-ethylhexyl)-amine, methyloctadecylamine, N-methylcyclohexylamine, N-ethylcyclohexylamine, 2-methylcyclohexylamine, 3-methylcyclohexylamine, 4-methylcyclohexylamine, N-methylaniline, N-ethylaniline, N-propylaniline, N-butyaniline, N-isobutylaniline, diphenylamine, N,2-dimethylaniline, N-ethyl-2-methylaniline, N-ethyl-3-methylaniline, N-butyl-3-methylaniline, N,4-dimethylaniline, N-ethyl-4-methylaniline, methylbenzylamine and phenylbenzylamine.

Polyethers of the general formula

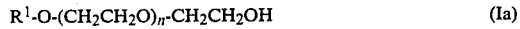
$$R^1\text{-O-}(CH_2CH_2O)_n\text{-}CH_2CH_2OH \quad (Ia)$$

in which $R^1$ represents a radical of a monoalcohol with 1–6 C atoms and n is an integer from 1 to about 160.

are particularly preferably used.

Polyethers in which $R^1$ represents n-butyl and n is an integer from 1 to about 90 are very particularly preferred. The polyethers or block copolyethers to be employed in the process according to the invention must have a water absorption capacity of at least 15%, relative to the weight of the polyether or block copolyether.

Compounds of the general formula

$$X\text{-}R^2\text{-Y} \quad (II),$$

in which $R^2$ represents a substituted or unsubstituted divalent aliphatic, cycloaliphatic, araliphatic or aromatic hydrocarbon radical and X and Y represent identical or different functional groups which are reactive towards hydrogen atoms which are active in Zerewitinoff reactions, are preferably used as compounds with at least two groups that are reactive towards hydrogen atoms that are active in Zerewitinoff reactions.

Preferred compounds of the formula (II) are those wherein $R^2$ represents divalent aliphatic hydrocarbon radicals with 2 to about 40 C atoms, especially with 2 to about 18 C atoms which are optionally substituted by halogen, cyano, nitro, optionally substituted alkyl- or arylmercapto, alkoxycarbonyl, alkoxysulphonyl, alkoxyphosphoryl, halogenocarbonyl, amidoyl, alkoxy, aryloxy, aryloxycarbonyl, aryloxysulphonyl or aryloxyphosphoryl, "aryl" denoting phenyl or naphthyl, either of which is optionally substituted by $C_{1-6}$-alkyl, halogen, cyano, nitro, optionally substituted alkoxy, alkylmercapto, aryloxy, arylmercapto or halogenoalkyl, or $R^2$ represents cycloaliphatic hydrocarbon radicals with 4–15 C atoms or aromatic hydrocarbon radicals with 6–15 C atoms, which in each case are optionally monosubstituted or polysubstituted by alkyl with 1 to atoms [which is optionally monosubstituted or polysubstituted by halogen, cyano, nitro, optionally substituted alkylmercapto, aryl (aryl denoting phenyl or naphthyl, either of which is optionally monosubstituted or polysubstituted by alkyl with 1–6 C atoms, halogen, cyano, optionally substituted alkoxy, alkylmercapto, arylmercapto or halogenoalkyl), alkoxycarbonyl, alkoxysulphonyl, alkoxyphosphoryl, halogenocarbonyl, amidoyl, alkoxy, aryloxy, arylmercapto, aryloxycarbonyl, aryloxysulphonyl or aryloxyphosphoryl, aryl in each case having the meaning indicated above], by cycloalkyl with 5–20 C atoms [which is optionally monosubstituted or polysubstituted by alkyl with 1–6 C atoms, halogen, cyano, nitro, optionally substituted alkylmercapto, alkoxycarbonyl, alkoxysulphonyl, alkoxyphosphoryl, halogenocarbonyl, amidoyl, alkoxy, aryl, aryloxy, arylmercapto, aryloxycarbonyl, aryloxysulphonyl or aryloxyphosphoryl, aryl in each case having the meaning indicated above], by phenyl or naphthyl [either of which is optionally monosubstituted or polysubstituted by alkyl, halogen, CN, optionally substituted alkoxy, alkylmercapto, alkoxycarbonyl, alkoxysulphonyl, alkoxyphosphoryl, halogenocarbonyl, amidoyl, aryloxy, arylmercapto, aryloxycarbonyl, aryloxysulphonyl or aryloxyphosphoryl, aryl having the meaning indicated above] or by halogen, cyano, nitro, alkoxycarbonyl, alkoxysulphonyl, alkoxyphosphoryl, halogenocarbonyl, amidoyl, optionally substituted alkoxy, alkylmercapto, amidoyl, optionally substituted alkoxy, alkylmercapto, aryloxy, arylmercapto, aryloxycarbonyl, aryloxysulphonyl or aryloxyphosphoryl, aryl in each case having the meaning indicated above, or $R^2$ represents araliphatic hydrocarbon radicals with 7–15 C atoms, one of the radicals X or Y being bonded to the aliphatic part and the other radical X or Y being bonded to the aromatic part, or both radicals X and Y being bonded to the aliphatic part. Both the aliphatic part and the aromatic part can be substituted by the substituents indicated above in the case of the aromatic hydrocarbons.

Preferably, X and Y, which are identical or different, each represent halogenocarbonyl, alkoxycarbonyl, carboxyl, carboxylic acid anhydride, sulphonic acid, sulphonic acid halide, sulphonic acid alkyl ester, phosphoric acid, phosphoric acid halide, phosphoric acid alkyl ester, isothiocyanate, isocyanate or isocyanide dihalide.

Particularly preferred compounds of the formula (II) are those wherein $R^2$ represents divalent aliphatic hydrocarbon radicals with 2–18 C atoms, which are optionally substituted by halogen, cyano, nitro, alkoxycarbonyl, alkoxysulphonyl, alkoxyphosphoryl, alkoxy, aryloxy, aryloxycarbonyl, aryloxysulphonyl or aryloxyphosphoryl, aryl having the meaning indicated above, or $R^2$ represents divalent cycloaliphatic hydrocarbon radicals with 5–10 C atoms or aromatic hydrocarbon radicals with 6–13 C atoms, which are in each case optionally monosubstituted or polysubstituted by alkyl with 1–4 C atoms, which is optionally substituted as indicated above, and/or by halogen, cyano, nitro, alkoxycarbonyl, alkoxysulphonyl, alkoxyphosphoryl, alkoxy, aryloxy, aryloxycarbonyl, aryloxysulphonyl or aryloxyphosphoryl, aryl having the meaning indicated above, or $R^2$ represents divalent araliphatic radicals with 8–13 C atoms, which are in each case optionally monosubstituted or polysubstituted by halogen, cyano, nitro, alkoxycarbonyl, alkoxysulphonyl, alkoxyphosphoryl, optionally substituted alkoxy, alkylmercapto, aryloxy, arylmercapto, aryloxycarbonyl, aryloxysulphonyl or aryloxyphosphoryl, aryl having the meaning indicated above. In addition to the substituents indicated, the aromatic part of the araliphatic radical can be substituted by $C_{1-4}$-alkyl or halogenoalkyl.

X and Y particularly preferably represent identical or different radicals selected from halogenocarbonyl, alkoxycarbonyl, carboxyl, carboxylic acid anhydride and isocyanate.

Compounds of the general formula (II) in which $R^2$ represents a divalent aliphatic hydrocarbon radical with 2–8 C atoms, which is optionally monosubstituted or polysubstituted by $C_{1-4}$-alkoxycarbonyl, and X and Y represent isocyanate are very particularly preferred.

In this connection there may be mentioned, for example, succinic acid, adipic acid, suberic acid, azelaic acid, sebacic acid, phthalic acid, isophthalic acid, trimellitic acid, tetrahydrophthalic anhydride, endomethylenetetrahydrophthalic anhydride, glutaric anhydride, maleic acid, maleic anhydride, fumaric acid, oleic acid and ethylene diisocyanate, dodecane 1,12-diisocyanate, cyclobutane 1,3-diisoycanate, cyclohexane 1,4-diisocyanate, 1-isocyanato-3,3,5-trimethyl-5-isocyanatomethylcyclohexane (DE-Auslegeschrift (German Published Specification) No. 1,202,785 and U.S. Pat. No. 3,401,190), hexahydrotoluylene 2,4- and 2,6-diisocyanate, hexahydrophenylene 1,3- and 1,4-diisocyanate, perhydrodiphenylmethane 2,4'- and 4,4'-diisocyanate, phenylene 1,3- and 1,4-diisocyanate, toluylene 2,4- and 2,6-diisocyanate, diphenylmethane 2,4- and 4,4'-diisocyanate and naphthylene 1,5-diisocyanate. Hexamethylene diisocyanate, tetramethylene diisocyanate, isophorone diisocyanate, toluylene diisocyanate and 1,6-diisocyanato-hexanoic acid methyl ester are particularly preferred.

Compounds which are active in the field of plant protection and in human medicine and veterinary medicine are employed as the active compounds which have a biological action and have at least one hydrogen atom that is active in Zerewitinoff reactions. Active compounds in the field of plant protection which may be mentioned are, inter alia, insecticides, acaricides, fungicides, bactericides, microbicides, herbicides, plant growth regulators, rodenticides and nematicides.

Active compounds in the field of human medicine and veterinary medicine which may be mentioned are, inter alia, medicaments for combating pain, hypnotic agents, psychopharmaceuticals, analeptic agents, appetite depressants, antiphlogistic agents, antihistamine agents, haemologic agents, diuretic agents, antidiuretic agents, medicaments having an action on the heart and vessels, on vascular walls and blood lipids, on the gastro-intestinal tract and on the respiratory tract, antimycotic agents, anthelmintic agents, antibacterial agents and agents against protozoal diseases. The prerequisite is that these active compounds must have at least one hydrogen atom that is active in Zerewitinoff reactions.

In this connection, there may be mentioned, especially, active compounds which contain one or more >N-H groups in the molecule. These include, inter alia, derivatives of nitrogen-containing heterocyclic compounds, such as pyrrole, indole, carbazole, pyrazole, imidazole, benzimidazole, hydantoin, oxazole, isoxazole, triazole, oxadiazole, tetrazole, pyridine, quinoline, isoquinoline, pyridazine, pyrimidine, uracil, barbituric acid, pyrine, quinazoline, pyrazine, pteridine, phenazine, oxazine (1,2 and 1,3 and 1,4), triazine (v, as and s), thiazine (1,2 and 1,3 and 1,4), thiadiazine or urea derivatives, carbamates, hydroxylamine derivatives, aminoalcohols, aminophenols, aminocarboxylic acids, carboxylic acid hydrazides, amidines, thiourea derivatives, guanidine derivatives, cyanic acid derivatives or naturally occurring substances (prepared by a natural, semi-synthetic or synthetic means), such as, for example, aminoacids, peptides, carbohydrates and nucleic acids with a free NH valency.

In this connection, there may also be mentioned biologically active alcohols, carboxylic acids, sulphonic acids, sulphenic acids, sulphinic acids, mercaptans, carbonic acid and phosphoric and phosphonic acids, and derivatives thereof.

Compounds with a nitrogen-heterocyclic grouping in the molecule which may be mentioned are: triazole derivatives, thiazole derivatives, imidazole derivatives, pyrimidine derivatives, uracil derivatives and triazine derivatives. The following compounds are specially preferred: 2-amino-4-methyl-5-carboxanilido-thiazole, 3-amino-1,2,4-triazole, 2-methoxy-4-ethylamino-6-isopropylamino-s-triazine, 5-bromo-3-sec.-butyl-6-methyluracil, 4-o-chlorophenylhydrazinyl-3-methylisoxazol-5-one, 2,4-dichloro-6-(o-chloroaniline)-s-triazine, 5-amino-1-bis-(dimethylamido)-phosphoryl-3-phenyl-1,2,4-triazole, 2,4-dimethyl-5-carboxanilidothiazole, O,O-dimethyl S-(4,6-diamino-1,3,5-triazin-2-yl)-methyl-phosphorodithioate, 4-(2-chlorophenylhydrazonyl)-3-methylisoxazol-5-one, 3,3'-ethylene-bis-(tetrahydro-4,6-dimethyl-2H-1,3,5-thiadiazine-2-thione), 2-(2'-furyl)-benzimidazole, S-(4,6-diamino-1,3,5-triazin-yl-methyl)-dimethylphosphorodithioate, 3-methyl-5-carboxymethyl-tetrahydro-1,3,5-thiazine-2-thione, 2,4-bis-isopropylamino-6-methylmercapto-s-triazine, 2-methylamino-4-isopropylamino-6-methylmercapto-s-triazine, 2-isopropylamino-4-ethylamino-6-methylmercapto-s-triazine, 2-ethylamino-4-tert.-butylamino-6-methylmercapto-s-triazine, 2-isopropylamino-4-methoxypropylamino-6-methylmercapto-s-triazine, 1,2-(3'-pyridyl)-pyrrolidine, dibenzo-1,4-thiazine, 2-methoxy-4,6-bis(isopropylamino)-s-triazine, 2-chloro-4,6-bis(isopropylamino)-s-triazine, 5-amino-4-chloro-2-phenyl-3(2H)-pyridazinone, 2-chloro-4,6-bis-ethylamino-s-triazine, 1-(p-sulphamylphenyl)-2,5-dimethyl-4-nitroso-pyrazole, 3-cyclohexyl-5,6-trimethyleneuracil, 4-amino-6-tert.-butyl-3-(methylthio)-1,2,4-triazin-5-(4H)-one, 3-methyl-4-amino-6-phenyl-1,2,4-triazin-5-(4H)-one, 1,3-di-p-chlorophenyl-(1H,2H,3H,4H,5H,6H)-1,3,5-triazine-2,4-dione, 7-chloro-2,3-dihydro-2,2-dihydroxy-5-phenyl-(1H)-benzo(f)-1,4-diazepine-3-carboxylic acid, 3,5-dioxo-2,3,4,5-tetrahydro-1,2,4-triazine, 2-nitroimidazole, 2-amino-5-nitrothiazole, D-4-amino-3-isoxazolidinone, 1,3-dimethyl-(1H,2H,3H,4H,5H,6H)-1,3,5-triazine-2,4-dione, 1,3diisopropyl-(1H,2H,3H,4H,5H,6H)-1,3,5-triazine-2,4-dione, 5,5-dibromo-hexahydropyrimidine-2,4,6-trione, 5-fluoro-pyrimidine-2,4-diol, 4-amino-5-fluoropyrimidin-2-(1H)-one, 2-thioxo-hexahydropyrimidine-4,6-dione, 1,3-di-p-fluorophenyl-(1H,2H,3H,4H,5H,6H)-1,3,5-triazine-2,4-dione, 2-amino-5-nitropyrimidine, 5-amino-(1H)-vic.-triazolo(d)-pyrimidin-7-ol, 1,3-bis-4-trifluoromethylphenyl-(1H,2H,3H,4H,5H,6H)-1,3,5-triazine-2,4-dione, 1-methyl-2-mercaptoimidazole, 2-amino-4-methylthiazole, 4-aminoperhydro-1,2-oxazin-3-one, 3,5-diiodo-4(1H)-pyridone, 1H-pyrazolo-(3,4,d)-pyrimidin-4-ol, 1H-pyrazolo-(3,4,d)pyrimidine-4-thiole, 6-mercaptopurine, 6-aminopurine, 6-aminopyrin-8-(9H)-one, 4-methyl-3-thiouracil, 1,3-bis-4-chloro-3-trifluoromethylphenyl(1H,2H,3H,4H,5H,6H)-1,3,4-triazine-2,4-dione, 6-carbamoyl-3-hydrazino-pyridazine, 2-(5-nitro-2-furyl)-5-amino-1,3,4-thiaziazole, trimethylolmelamine, N-guanidino-formimidoylmorpholine, 4-amino-2,2,5,5-tetrakis(trifluoromethyl)-3-imidazoline, 6-chloro-7-sulphamoyl-(2H)-1,2,4-benzothiadiazine. 1,1-dioxide, 1,3-bis-3-chloro-4-trifluoromethylphenyl-(1H,2H,3H,4H,5H,6H)-1,3,5-triazine-2,4-dione, 1,3-dimethylpurine-2,6(1H,3H)-dione, 4-amino-1-ribofuranosyl-1,3,5-triazin-2-(1H)-one, 2-amino-5-p-chlorophenyl-2-oxazoline, 2-sulphanilamidothiazole, 3,3-diethylpyridine-2,4(1H,3H)-dione, 3-ethyl-1-allyl-6-aminouracil, 3(5)-ribofuranosyl-4-hydroxy-pyrazole-5(3)-carboxamide, 5-ethyl-5-isopropyl-hexahydropyrimidine-2,4,6-trione, 3-chloro-4-(3-chloro-2-nitrophenyl)-pyrrole, 5,7-dichloro-2-methylquinolin-8-ol, 2-amino-5-(4-trifluoromethylphenyl)-2-oxazoline, 2-sulphanilamidopyrimidine, 1,3-bis-(3,4-dichlorophenyl)(1H,2H,3H,4H,5H,6H)-1,3,5-triazine-2,4-dione, 1-(3-aminophenyl)-2(1H)-pyridone, 4-benzyl-2-thiouracil, 4-amino-6-methyl-2-phenyl-3(2H)-pyridazinone, 2(p-aminobenzenesulphonamido)-4-methyl-pyrimidine, 2-(p-aminobenzenesulphonamido)-5-methylpyrimidine, 3-(p-aminobenzenesulphonamido)-6-methoxy-pyridazine, 2-(p-aminobenzenesulphonamido)-5-methoxypyrimidine, 4-(p-aminobenzenesulphonamido)-6-methoxypyrimidine, 2-(p-aminobenzenesulphonamido)-3-methoxypyrazine, 2-(p-aminobenzenesulphonamido)-4,5-dimethoxyloxazole, 5-(p-aminobenzenesulphonamido)-3,4-dimethylisoxazole, 2-sulphonanilamide-4,5-dimethoxy-1,3,5-triazine, 1,3-bis-(p-chloro-4-phenoxyphenyl)-(1H,2H,3H,4H,5H,6H)-1,3,5-triazine-2,4-dione, 4,6-diamino-1-(p-chlorophenyl)-1,2-dihydro-2,2-dimethyl 1,3,5-triazine, 5-allyl-5-isobutyl-2-thiobarbituric acid, 4,6-dimethyl-2-sulphanilamido-pyrimidine, 2,4-dimethyl-6-sulphanilamidopyrimidine, 5,5-diallylbarbituric acid, 4-hydroxy-1H-pyrazolo(3,4,d)pyrimidine, 6-(1-methyl-4-nitro-imidazolyl-5-thio)-purine, 5,5-diethylbarbituric acid, 4-methyl-4-ethyl-piperidine-2,6-dione, 3-benzyl-6-trifluoromethyl-7-sulphamoyl-3,4-dihydro-3,4-dihydro-2H-1,2,4-benzothiadiazine 1,1-dioxide, 1-{1-[3-(4-fluorobenzoyl)-propyl]-4-piperidyl}benzimidazolone, 2-(2-methylaminoethyl)-piperidine, 7-bromo-2-oxo-5-(2-pyridyl)-2,3-dihydro-1H-1,4-benzodiazepine, 3-hydroxymethyl-6-oxo-5-semicarbazono-2,3,5,6-tetrahydro-indole, 7-chloro-2-methylamino-5-phenyl-3H-1,4-benzodiazepine 4-oxide, 7-chloro-4-[(4-diethylamino-1-methyl-butyl)-amino]quinoline, 5-chloro-1,3-benzoxazolone, 5-(2-chlorophenyl-7-nitro-2-oxo-2,3-dihydro-1H-1,4-benzodiazepine, 2-(2,6-dichloroanilino)-$\Delta^2$-imidazoline, 5-(3-methylaminopropyl)-10,11-dihydro-5H-dibenzo(b,f)azepine, 5-amino-1,3-bis-(2-ethylhexyl)-5-methyl-hexahydropyrimidine, 5-methylisoxazole-3-carboxylic acid $N^2$-benzylhydrazide, pyridine-4-carboxylic acid hydrazide, 2-(1-naphthylmethyl)-$\Delta^2$-imidazoline, 8-amino-2-methyl-4-phenyl-1,2,3-tetrahydroisoquinoline, 2-(4-tert.-butyl-3-hydroxy-2,6-dimethyl-benzyl)-$\Delta^2$-imidazoline, 2-(2,2-dicyclohexylethyl)-piperidine, 4-(2-hydroxy-3-isopropylaminopropoxy)-indole, 6-chloro-2-methyl-7-sulphamoyl-3-(2,2,2-trifluoroethylmercaptomethyl)-3,4-dihydro-2H-1,2,4-benzothiadiazine 1,1-dioxide, 4-aminobenzenesulphonic acid 4,5-dimethyl-1,3-oxazol-2-yl-guanide, 3-(4-aminobenzenesulphonamido)-5-methylisoxazole, 4-(4-aminobenzenesulphonamido)-2,6-dimethylpiperidine, 2-(4-1,3-thiazolyl)-benzimidazole, 2-(5-tetralylamino)-$\Delta^2$-imidazoline, 2-(4-tert.-butyl-2,6-dimethylbenzyl)-$\Delta^2$-imidazoline, 2,4-dimethoxy-6-sulphanilamidopyrimidine, 5,6-dihydro-2-(2,6-xylidino)-4H-1,3-thiazine, triacetyl-6-azauridine, 1-(4-chloro-3-sulphamoylbenzamido)-2,6-dimethylpiperidine, 1-phenyl-5-sulphanilamidopyrazole, 4-(m-hydroxyphenyl)-1-methyl-4-propionylpiperidine, 3-[3-(3-hydroxy-2-piperidyl)-acetonyl]-4-(3H)-quinazolone, 4-(4-diethylamino-1-methylbutylamino)-7-chloro-quinoline, 2-(2,2-dicyclohexylvinyl)-piperidine, 1-methyl-2-(β-hydroxy-β-phenylethyl)-6-phenacylpiperidine, diethylbarbituric acid, ethylcyclohexenylbarbituric acid, methyl-cyclohexenylmethylbarbituric acid, 2,6-dimethyl-3,5-diacetyl-4-o-nitrophenyl-1,4-dihydropyridine, N-(4'-chloro-3'-sulphamoylbenzenesulphonyl)-N-methyl-2-aminomethyl-2-methyltetrahydrofurane, 2-(4-sulphamoylphenyl)-tetrahydro-2H-1,2-thiazine 1,1-dioxide and 5-acetamido-2-sulphamoyl-1,3,4-thiadiazole.

Active compounds which may be mentioned from the series of urea derivatives are: 1-(1-naphthyl)-2-thiourea, 3-(p-bromophenyl)-1-methyl-1-methoxyurea, 3-(p-chlorophenyl)-1,1-dimethylurea, 3-[p-(p-chlorophenoxy)phenyl)]-1,1-dimethylurea, 1,3-bis-(1-hydroxy-2,2,2-trichloroethyl)urea, 1,1-dimethyl-3-(3-(N-tert.-butylcarbamyloxy)-phenyl)-urea, 3-(3,4- dichlorophenyl)-1,1-dimethylurea, 3-phenyl-1,1-dimethylurea, 1,1-dimethyl-3-(m-trifluoromethylphenyl)-urea, 3-(3,4-dichlorophenyl)-1-methoxy-1-methylurea, 3-(4-chlorophenyl)-1-methoxy-1-methylurea, 3-(3,4-dichlorophenyl)-1-n-butyl-1-methylurea, 1-(2-methylcyclohexyl)-3-phenylurea, 3-(2-benzothiazolyl)-1-methylurea, 3-(4-bromo-3-chlorophenyl)-1-methoxy-1-methylurea, 3-cyclooctyl-1,1-dimethylurea, 3-(3-methylphenyl)-1,1-dimethylthiourea, 3-[5-(3a,4,5,6,7,7a-hexahydro-4,7-methaneindanyl)]-1,1-dimethylurea, 1,3-dimethyl-3-(2-benzthiazolyl)-urea, 3-[3-chloro-4-(2'-chloro-4'-nitrophenoxy)phenyl]-1-(2,2'-dichlorobenzoyl)-urea, 3-[4-(2-chloro-4-trifluoromethylphenoxy)-phenyl]-1-(2,2'-difluorobenzyl)-urea, 3-[4-(2-chloro-4-trifluoromethylphenoxy)phenyl]-1-o-chlorobenzoylurea, 3-(4-chlorophenyl)-1-(2,2'-difluorobenzoyl)-urea, 3-(4-nitrophenyl)-1-(2,2'-difluorobenzoyl)-urea, 3-(4-trifluoromethoxyphenyl)-1-o-chlorobenzoylurea, 3-(4-trifluoromethoxyphenyl)-1-(2,2-dichlorobenzoyl)-urea, 1,3-bis-(3,4-dichlorophenyl)-urea, phenylthiourea, 1,3-bis-(4-dichlorophenyl)-urea, 1-p-chlorophenyl-3-o-chlorophenylurea, 1-p-chlorophenyl-3-o,m-dichlorophenylurea, 1-p-chlorophenyl-3-o,p-dichlorophenylurea, 1-p-chlorophenyl-3-(2,5-dichlorophenyl)-urea, 1-hydroxymethyl-3-methyl-2-thiourea, 2-ethylisothiourea, allylthiourea, N,N-dimethylbiguanide, 5-nitro-2-furaldehyde semicarbazone, 1-ethyl-3-(5-nitro-2-thiazolyl)-urea, 2-ethyl-cis-crotonoylurea, α-ethyl-bromobutyrylurea, α-chlorophenylacetyl-urea n-ethoxy-phenylurea, vanillin thiosemicarbazone, N-acetyl-N'-diethyl-bromoacetylurea, 2-isopropyl-4-pentenoylurea, p-acetamide-benzaldehyde thiosemicarbazone 1-(p-chlorophenylsulphonyl)-3-propyl-urea, 2-phenylbutyryl-urea, p-(3-ethylureido)-benzaldehyde thiosemicarbazone, 1-butyl-3-sulphanilylurea, phenylethylmalonylurea, N,N'-(m-amidinophenyl)-urea, p-cinnamoyloxyiphenyl-urea, 1-(hexahydro-1H-azepin-1-yl)-3-{p[5-(methyl-3-isoxazole-carboxamido)-ethyl]-phenylsulphonyl}-urea, N-acetyl-N'-(2,2-diethyl-2-bromo)-acetyl-urea, α-bromo-isovaleroyl-urea and 2-β-aminoethyl-isothiourea.

Active compounds of the carbamate series which may be mentioned are: 4-benzothienyl N-methylcarbamate, 1-naphthyl N-methylcarbamate, 2-chlorophenyl N-methylcarbamate, isopropyl-N-(m-chlorophenyl)-carbamate, 3,4-dimethyl-phenyl-N-methylcarbamate, 4-dimethylamino-3,5-xylyl-N-methylcarbamate, 2,6-di-tert.-butyl-p-tolyl N-methylcarbamate, 3-(1-methylbutyl)phenyl-N-methylcarbamate, 3-isopropyl-phenyl N-methylcarbamate, 4-(methylthio)-3,5-xylyl N-methylcarbamate, O-methyl N-3,4-dichlorophenylcarbamate, O-isopropyl-N-phenylcarbamate, 2-isopropoxyphenyl-N-methylcarbamate, m-tolyl-N-methylcarbamate, 3,4-xylyl-6-chloro-N-methylcarbamate, O-methyl N-4-aminobenzenesulphonylcarbamate, 1-methylprop-2-ynyl N-(3-chlorophenyl)-carbamate, 2,3-dihydro-2,2-dimethyl-7-benzofuranyl-N-methylcarbamate, 2-isopropylphenyl N-methylcarbamate, 3,5-dimethyl-4-methylmercaptophenyl N-methylcarbamate, 2-chlorophenyl-N-o,o'-difluorobenzoylcarbamate, 4-chlorophenyl N-o,o'-difluorobenzoylcarbamate, methyl N-o,o'-difluorobenzoylcarbamate, isopropyl- N-o,o'-difluorobenzoylcarbamate, 2,6-dichlorophenyl N-o,o'-difluorobenzoylcarbamate, 2,6-dichlorophenyl-N-o,o'-dichlorobenzoylcarbamate, 2-nitrophenyl-N-o,o'-difluorobenzoylcarbamate, 4-nitrophenyl-N-o,o'-difluorobenzoylcarbamate, 2-nitro-4-chlorophenyl-N-o,o'-difluorobenzoylcarbamate, 2-chloro-4-nitrophenyl-N-o,o'-difluorobenzoylcarbamate, N-o,o'-difluorobenzoyl-carbaminic acid S-p-chlorophenylthioester, 1-methyl-5-nitro-azol-2-yl methylcarbamate, 1-ethyl-1-methylpropyl carbamate, 3-methyl-2,4-pentanediol dicarbamate, 1-ethynylcyclohexyl carbamate, 2-methyl-2-n-propyl-1,3-propanediol dicarbamate, α-ethynylbenzylcarbamate, 3-(p-chlorophenoxy)-2-hydroxypropyl carbamate, α-methylphenylethyl carbamate, 2-hydroxyethyl N-benzylcarbamate, 1-cyclohexyl-propyl carbamate, α-isopropyl-benzyl carbamate, (2-methyl-2-nonyl-1,3-dioxolan-4-yl)-methyl carbamate and 2-methyl-2-propylpropane-1,3-diol dicarbamate.

Active compounds which may be mentioned from the series of carboxylic acid, sulphonic acid and phosphoric acid derivatives are: N-[2-mercaptoethyl-benzensulphonamido-S(O,O'-diisopropylphosphorodithioate)]4-tert.-butyl-2-chlorophenyl-O,N-dimethylphosphorimidate, 3-amino-2,5-dichlorobenzoic acid, N-(3-chloro-4-methylphenyl)-2-methylpentanamide, O,O-dimethyl(2,2,2-trichloro-hydroxyethyl)phosphonate, 5,2-dichloro-4-nitro-salicylanilido-ethanolamine, O,O-dimethyl S-(N-methylcarbamoylmethyl)thiophosphate, O-ethyl O-(3-methyl-4-methylthiophenyl)isopropylamido-phosphate, O-ethyl-O-(2-isopropoxy-carbonyl)-phenyl-N-isoropyl-amidothiophosphate, 3,4-dichlorophenylpropionanilide, 5-methyl-1,3,4-thiadiazole-2-sulphonamide, L-2-amino-3-(N-nitrosohydroxyamino)-propionic acid, pryazole-1-carboxamide, pyrazole-1-thiocarboxamide, 2-acetylamino-1,3,4-thiadiazole-5-sulphonamide, pyrazine-carboxamide, 5-acetylimino-4-methyl-$4^2$-1,3,4-thiadiazoline-2-sulphonamide, pyridine-3-carboxamide, 4-amino-3-iodobenzenesulphonamide, pyridine-4-carboxylic acid hydrazide, p-aminobenzenesulphonamide, 2-methyl-4-aminopyridine-5-carboxylic acid hydrazide, α-aminotoluene-p-sulphonamide, 2-ethyl-isonicotinic acid thioamide, α,α-dichloro-N-[β-(hydroxymethyl)-p-nitrophenacyl]-acetamide, D(−)-threo-N-(β-hydroxy-α-hydroxymethyl-p-nitrophenylethyl)dichloroacetamide, D(−)-threo-N-(β-hydroxy-α-hydroxymethyl-p-nitrophenylethyl)-azidoacetamide, N-sulphanilyl-3-methyl-2-butenamide, N-(2-chloro-4-nitrophenyl)-5-chlorosalicylamide, p-aminosalicylic acid phenyl ester, 4-chloro-$N^1$-methyl-$N^1$-(2-methyltetrahydrofurfuryl)-m-benzenedisulphonamide, 2-diethylaminoethyl p-aminobenzoate, 2-(diethylaminoacetylamino)-3-methylbenzoic acid methyl ester, 2-ethyl-6-methyl-α-diethylaminoacetanilide, β-dimethylaminoethyl p-butylaminobenzoate, D-7-(2-amino-2-phenylacetamido)-3-methyl-8-oxo-5-thia-1-azabicyclo(4,2,0)-oct-2-ene-2-carboxylic acid, β-diethylaminoethyl 3-amino-4-propoxybenzoate, 7-chloro-4-dimethylamino-1,4,4a,5,5a,6,11,12a-octahydro-3,6,10,12,12a-pentahydroxy-1,11-dioxo-2-naphthacenecarboxamide, 2,2-diallyl-N,N'-bis-(4-amino-2-methyl-6-quinolyl)-malonamide, 4-methyl-3-(2-propylamino-propionylamino)-thiophene-2-carboxylic acid methyl ester and 4-chloro-5-sulphamoyl-salicylic acid 2,6-dimethylanilide.

Active compounds which may be mentioned from the series of naturally occurring substances are: 2-ethylisonicotinthioamide, 5-hydroxytryptamine, (−)-3-(3,4-dihydroxyphenyl)-2-methylalanine, 7-(2,3-dihydroxypropyl)theophylline, α-1-(methylaminoethyl)-benzyl alcohol, DL-α-methyltryptamine, 4-(2,2'-dichloroethylamino)-proline ethyl ester, p-[bis-(2-chloroethyl)-amino]-L-phenylalanine, D-4-amino-4-carboxybutylpenicillin, 2',4-epoxy-3-(4'-hydroxyphenyl)-7-hydroxycoumarin, 4-hydroxybenzylpenicillin, 6-[D-(−)-α-aminophenylacetamido)]-pencillanic acid, 7-(5-amino-5-carboxyvaleramido)-cephalosporanic acid, 6-(3-amino-2-phenylpropionamido)-penicillanic acid, 6-(α-phenoxybutyramido)-pencillanic acid, 7-(2-(α-methylphenethylamino)ethyl)-theophylline, N-(2-hydroxy-1-methylethyl)-D-(+)-lysergamide, 4-chloro-17β-hydroxyandrost-4-en-3-one, N²-{p-[1-(2-amino-4-hydroxy-6-pteridinyl)-ethyl-methylamino]-benzoyl}-glutamine, 1,4-pregnadiene-17α-21-diol-3,11,20-trione, 7-chloro-4-dimethylamino-1,4,4a,5-,5a,6,11,12a-octahydro-3,6,10,12,12a-pentahydroxy-6-methyl-1,11-dioxo-2-naphthacenecarboxamide, 9-acetyl-7,8,9,10-tetrahydro-6,7,9,11-tetrahydroxy-4-methoxy-5,12-naphthacenequinone-7-(3-amino-5-methyl-2,3-dideoxy-L-lyxopyranoside, 2α,11-dimethoxy-3-(3,4,5-trimethoxybenzoyloxy)-yohimbane-1-carboxylic acid methyl ester, O-[2,6-diamino-2,3,4,6-tetradeoxy-D-glycerohex-4-ene-pyranosyl(1→4)]-O-[3-deoxy-4-C-methyl-3-methylamino-β-L-arabinopyranosyl-(1→6)]-2-deoxy-D-streptamine, 1-β-D-arabinofuranosylcytosine 5'-(1-adamantane-carboxylate), 6-aminopenicillanic acid, D-α-aminobenzoylaminopenicillanic acid, L-3-(3,4-dihydroxyphenyl)-2-methylalanine, 6-[(R)-2-(2-oxo-imidazolidine-1-carboxamido)-2-phenylacetamido]-penicillanic acid, 7-(D-α-aminophenylacetamido)-3-methyl-3-cephem-4-carboxylic acid, and 7-[2-(1-methyl-2-phenylethylamino)ethyl]-theophylline.

The herbicidally active compound 4-amino-6-tert.-butyl-3-methylthio-1,2,4-triazin-5-(4H)-one, which, after modification according to the present invention, also has some insecticidal activity, may be mentioned in particular.

The procedure followed in carrying out process variant (a) according to the invention is advantageously as described below:

If, for example, an ethylene oxide polyether started from n-butanol and having a terminal OH group, hexamethylenediisocyanate and, as the active compound, 4-amino-6-tert.-butyl-3-(methylthio)-1,2,4-triazin-5-(4H)-one are used, the process according to the invention can be carried out as follows:

The amount of the ethylene oxide polyether which corresponds to one equivalent of OH groups is dehydrated under a vacuum of 10 to 200 mm Hg at a temperature of 60°–160° C., preferably 80°–120° C., for 10 minutes to 2 hours, preferably 20 minutes to 60 minutes and is then brought to the external pressure with an inert gas. 0.01 to 1% by weight, relative to the amount of ethylene oxide polyether which remains, of an organic carboxylic acid halide, preferably benzoyl chloride, is added and the mixture is subsequently stirred at 60°–160° C., preferably 70°–120° C., for 1 to 30 minutes, preferably 5–10 minutes. The amount of OH equivalents that remain is determined titrimetrically on a sample. An amount of hexamethylenediisocyanate equivalent to the OH amount which remains is added, such that an equivalent ratio of OH:NCO=1:2 is maintained. The mixture is subsequently stirred at a temperature of 60°–160° C., preferably 80°–100° C., care being taken that no moisture enters the apparatus, until the calculated residual isocyanate content is achieved. The mixture is cooled and a polyether isocyanate of the ideal formula

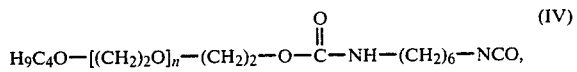

in which n has the meaning indicated above, is obtained.

This polyester isocyanate is reacted with the active compound in a second stage of the process, which directly follows the first, at a temperature of 25°–150° C., preferably 80°–140° C., and with exclusion of moisture, it being possible for the active compound to be dissolved in an inert solvent. The reaction has gone to completion when no further isocyanate can be detected in the reaction mixture by IR spectroscopy. The modified active compound has the general ideal formula

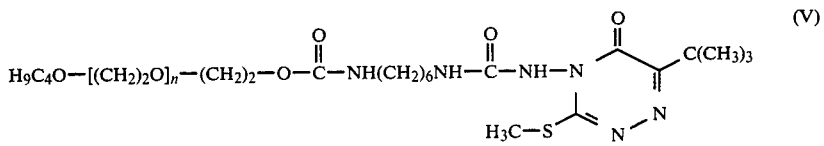

in which n has the meaning indicated above.

Reactions of other polyethers having hydroxyl end groups with other diisocyanates or polyisocyanates or diisothiocyanates or polyisothiocyanates and other active compounds containing, per molecule, at least one hydrogen atom that is active in Zerewitinoff reactions can, of course, also be carried out in an analogous manner.

A further possibility for the preparation of the substances according to the invention consists in using a polyether having a hydroxyl end group and a dicarboxylic acid or a dicarboxylic acid derivative, preferably a dicarboxylic acid anhydride or a dicarboxylic acid dimethyl ester, as the starting components, and an active compound containing at least one hydrogen atom that is active in Zerewitinoff reactions, for example a triazine-2,4-dione.

The polyether-esters necessary for the reaction which proceeds in the second stage can be prepared in a manner which is in itself known and customary. The two processes below, in particular, can be used for this process.

In the first process, a dicarboxylic acid which is free from mineral acid and which is to be purified, if necessary, by recrystallization is used as the starting material. The desired polyether-alcohol is added as the second starting component, the equivalent ratio —OH:—COOH being 1:2. After adding 0.05 to 0.5% by weight, preferably 0.05 to 0.2% by weight, of a catalyst, for example a tin compound, such as di-n-butyl-tin oxide, di-n-butyl-tin diesters and others, or titanic acid esters, especially tetraisopropyl titanate, the reaction components are heated in a suitable apparatus, while passing an inert gas, for example nitrogen, through. The first water is split off at about 180° C. The water is removed from the reaction mixture by distillation. The reaction temperature is increased up to 240° C. in the course of several hours. The reaction medium remains heterogeneous until shortly before the end of the complete esterification. After about 24 hours, the reaction has ended.

In the second process, a dicarboxylic acid dimethyl ester is used as the starting material and is trans-esterified with the desired polyether-alcohol, while passing a stream of an inert gas, for example nitrogen, through. Titanic acid esters, dialkyl-tin esters or di-n-butyl-tin oxide can again be employed as trans-esterification catalysts, in concentrations of 0.005 to 0.5% by weight. After a temperature of about 120° C. has been reached, the first methanol is split off. The temperature is increased to 220° to 230° C. in the course of several hours. The trans-esterification has ended after 2 to 24 hours, depending on the mixture chosen.

Further reaction of the polyether-carboxylic acid, formed by the first process, or of the polyether-carboxylic acid ester, formed by the second process, with the active compound to be employed, preferably a compound containing an NH group, is effected by methods which are in themselves known.

In the case where the polyether-carboxylic acid is used as the starting compound this is reacted with a lower aliphatic alcohol, preferably methanol, optionally in the presence of a suitable organic solvent, to give the polyether-carboxylic acid ester.

In both cases the polyether-carboxylic acid ester is then reacted with the biologically active compound in a suitable organic solvent at a temperature which is high enough to enable the methanol formed to be distilled off, preferably between about 80° and 140° C., to give, in the case of a compound containing an NH group, the corresponding amide.

In this procedure, it is frequently particularly advantageous to add a catalytic amount of an alkali metal, especially sodium, to the reaction, since the reaction times can thereby be shortened considerably.

The reaction has ended when no further methanol can be distilled off, usually after 1 to 24 hours. The mixture is then allowed to cool, the solvent is removed and the resulting modified active compound according to the invention is optionally recrystallized.

If a polyether started from butanol, tetramethylene-dicarboxylic acid dimethyl ester and, as the active compound, 1,3-di-p-chlorophenyl-(1H,2H,3H,4H,5H,6H)-triazine-2,4-dione are used, the procedure can be represented by formulae in the manner below:

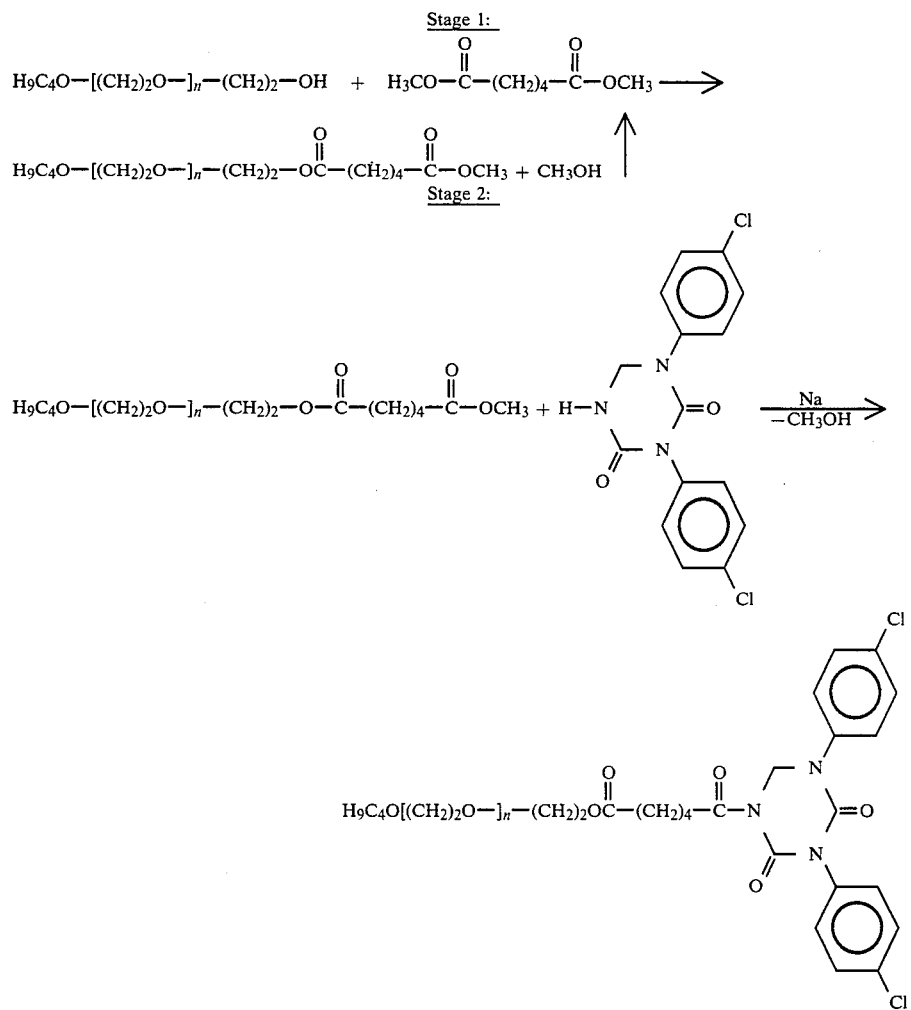

wherein n has the meaning indicated above.

A further possibility for the preparation of the substances according to the invention consists in using a polyether having a hydroxyl end group, a di-carbonic acid ester chloride and an active compound containing at least one hydrogen atom that is active in Zerewitinoff reactions, for example a triazinedione. The polyether-carbonic acid ester chloride necessary for the reaction which proceeds in the second stage can be prepared in a manner which is in itself known and customary (see Houben-Weyl, Methoden der organischen Chemie (Methods of Organic Chemistry) VIII, pages 101–105). The process below can be used in particular.

A bifunctional compound with two terminal OH groups, for example butane-1,4-diol, is used as the starting material. This compound is dissolved in a suitable organic solvent and reacted with phosgene at room temperature. For this reaction, phosgene is passed through the solution for between 0.5 and 10 hours, while the mixture is simultaneously kept at room temperature (at most 40° C.) by external cooling. The mixture is then heated to 80°–150° C., preferably 100°–120° C., whereupon the reaction is brought to completion and excess phosgene is removed. If, for example, butane-1,4-diol is used, at this point in time butane-1,4-chlorocarbonic acid ester is present in the crude form in the particular acid ester is present in the crude form in the particular solvent. The bis-chlorocarbonic acid ester is then reacted with the monofunctional polyether to give the monochlorcarbonic acid-monocarbonic acid polyether-ester.

A procedure is appropriately followed in which the bis-chlorocarbonic acid ester is initially introduced in a suitable solvent, together with an amount of an organic and/or inorganic base which is sufficient to bond the hydrochloric acid formed during the reaction, and the polyether containing hydroxyl groups is metered in very slowly, two equivalents of chlorocarbonic acid ester end groups being present per one equivalent of hydroxyl groups. The mixture is then allowed to react completely at a temperature of 10° to 100° C., preferably 30° to 70° C., for 0.5 to 12 hours, preferably 1 to 4 hours. The base hydrochlorde is separated off in a manner which is in itself known. The resulting monochlorocarbonic acid ester-monocarbonic acid polyether-ester is sufficiently pure for subsequent reaction with the active compound to be modified.

This reaction with the active compound, in particular a compound containing an NH group, is preferably carried out in the manner decribed below. In a preliminary stage, the mono-chlorocarbonic acid-monocarbonic acid polyether-ester is reacted with equivalent amounts of methanol to give the carbonic acid methyl ester-carbonic acid polyether-ester or, in the case of butane-1,4-diol, to give the butane-1,4-carbonic acid methyl ester-carbonic acid polyether-ester. Such esterification reactions with methanol as the alcohol component are known.

In the reaction directly following this preliminary reaction, the carbonic acid methyl ester-carbonic acid polyether-ester is reacted with the active compound component in a suitable organic solvent at a temperature which is sufficient to enable methanol formed to be distilled off, preferably between 80° and 140° C., to give, in the case of a compound containing an NH group, the corresponding amine. It is frequently of particular advantage to add catalytic amounts of an alkali metal, especially sodium, during the reaction, since the reaction times can thereby be shortened considerably. The reaction has ended when no further methanol can be distilled off, usually after 1 to 24 hours. The mixture is then allowed to cool, the solvent is removed and the resulting active compound modified by the process according to the invention is optionally recrystallized.

In the case where a polyether started from butanol and butane-1,4-bischlorocarbonic acid ester are used as the starting components and 1,3-dimethyl-(1H,2H,3H,4H,5H,6H)-triazine-2,4-dione is used as the active compound, the procedure indicated above can be represented by means of formulae in the following manner:

Stage 1:

$$H_9C_4O-[(CH_2)_2O]_n-(CH_2)_2-OH +$$

$$Cl-\overset{O}{\underset{\|}{C}}-O-(CH_2)_4-O-\overset{O}{\underset{\|}{C}}-Cl \xrightarrow{-HCl}$$

$$H_9C_4O[(CH_2)_2O]_n-(CH_2)_2-O-\overset{O}{\underset{\|}{C}}-O-(CH_2)_4-O-\overset{O}{\underset{\|}{C}}-Cl$$

Stage 2:

$$H_9C_4O-[(CH_2)_2O]_n-(CH_2)_2-O-\overset{O}{\underset{\|}{C}}-O-(CH_2)_4-O-\overset{O}{\underset{\|}{C}}-Cl + CH_3OH \xrightarrow{-HCl}$$

$$H_9C_4O[(CH_2)_2O]_n-(CH_2)_2-O-\overset{O}{\underset{\|}{C}}-O-(CH_2)_4-O-\overset{O}{\underset{\|}{C}}-OCH_3$$

Stage 3:

$$H_9C_4O[(CH_2)_2O]_n-(CH_2)_2-O-\overset{O}{\underset{\|}{C}}-O-(CH_2)_4-O-\overset{O}{\underset{\|}{C}}-OCH_3 +$$

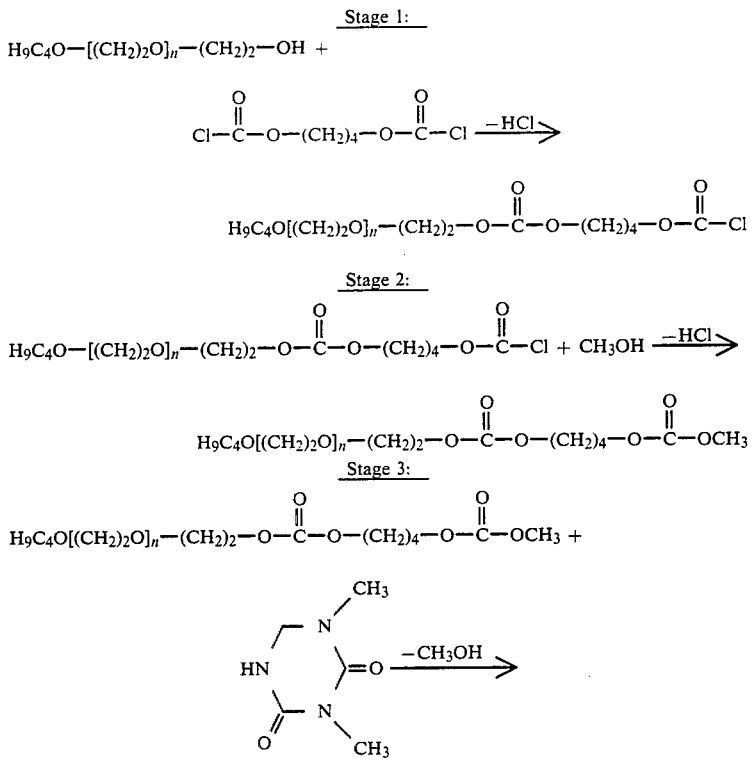

-continued

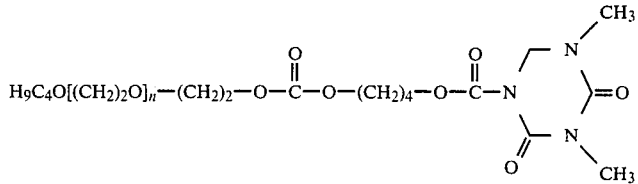

wherein n has the meaning indicated above.

Possible diluents or solvents for the process according to the invention are any of the inert organic solvents. These include, as preferences, benzene, toluene, xylene, methylene chloride, chloroform, chlorobenzene, diethyl ether, dibutyl ether and dioxane, as well as acetone, methyl ethyl ketone, ethyl acetate and acetonitrile.

The procedure for carrying out process variant (b) according to the invention is advantageously as described below.

If, for example, an ethylene oxide polyether started from n-butanol and having a terminal OH group, hexamethylene diisocyanate and 4-amino-6-tert.-butyl-3-(methylthio)-1,2,4-triazin-5-(4H)-one are used, the process according to the invention can be carried out as follows.

The amount of the ethylene oxide polyether which corresponds to one equivalent of OH groups is dehydrated under a vacuum of 10 to 200 mm Hg at a temperature of 60°–160° C., preferably 80°–120° C., for 10 minutes to 2 hours, preferably 20 minutes to 60 minutes, and is then brought to the external pressure with an inert gas. 0.01 to 1% by weight, relative to the amount of ethylene oxide polyether which remains, of an organic carboxylic acid halide, preferably benzoyl chloride, is added and the mixture is subsequently stirred at 60°–160° C., preferably 70°–120° C., for 1 to 30 minutes, preferably 5–10 minutes. The amount of OH equivalents which remain is determined titrimetrically on a sample.

Hexamethylene diisocyanate is then initially introduced into a second reaction vessel in an amount such that an equivalent ratio of OH:NCO=1:2, relative to the OH equivalents of the polyether which remain, is maintained. The active compound, if necessary dissolved in a suitable solvent, is then metered in, while stirring vigorously, in an amount such that an equivalent ratio of NCO groups:H atoms that are active in Zerewitinoff reactions, of 2:1 is maintained. The mixture is subsequently stirred at 40°–160° C., preferably 60°–120° C., for 10 minutes to 48 hours and the entire amount is then added to the dehydrated polyether. The reaction has proceeded to completion when no further isocyanate can be detected in the reaction mixture by IR spectroscopy. The modified active compound has the ideal formula

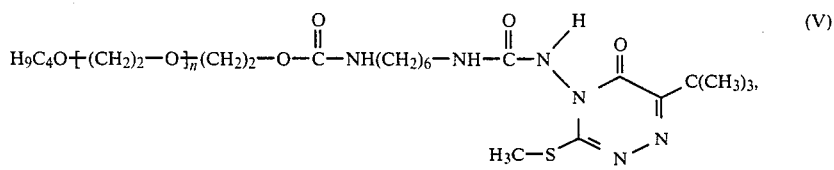 (V)

in which n has the meaning indicated above.

It should be pointed out that the products obtainable both by process variant (a) and by process variant (b) have the same ideal formula only in the case of compounds X-R²-Y which are built up symmetrically. In contrast, if a compound which is not built up symmetrically is chosen as the compound X-R²-Y, and the end groups X and Y thereof are indeed indentical structurally (for example both NCO) but have a different reactivity because of the chemical surroundings, the product in which the more reactive end group X and Y has reacted with the compound first employed, containing a hydrogen atom that is active in Zerewitinoff reactions, is always preferentially obtained.

Thus, for example, when an ethylene oxide polyether started from n-butanol, isophorone diisocyanate and 3-methyl-4-amino-6-phenyl-1,2,4-triazin-5-(4H)-one are employed, a product of the ideal formula

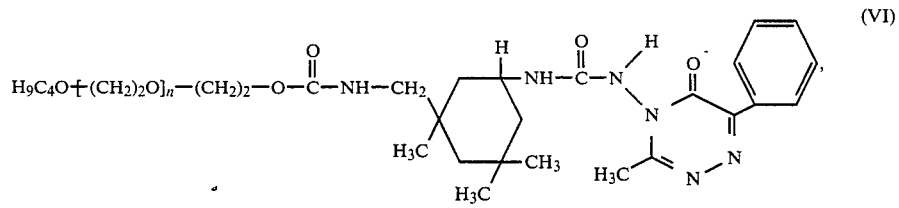 (VI)

in which n has the meaning indicated above, is obtained according to process variant (a), whereas according to the process variant (b) a product of the ideal formula

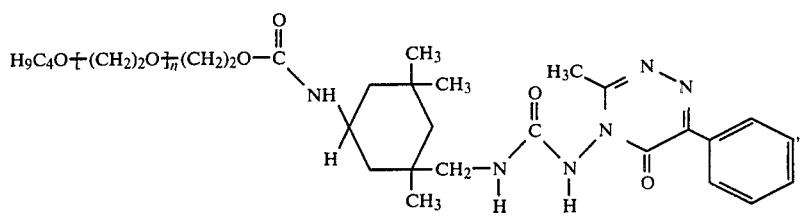
(VII)

in which n has the meaning indicated above, is obtained.

The procedure followed in carrying out process variant (c) according to the invention is advantageously as described below.

If, for example, an ethylene oxide/propylene oxide block copolyether started from n-butanol and having a terminal hydroxyethylene group, 1,6-diisocyanatohexanoic acid methyl ester and 2,6-dimethyl-3,5-diacetyl-4-o-nitrophenyl-1,4-dihydropyridine are used, the process according to the invention can be carried out as follows:

The amount of the polyether which corresponds to one equivalent of OH groups is dehydrated under a vacuum of 10 to 200 mm Hg at a temperature of 60°–160° C., preferably 80°–120° C., for 5 minutes to 1 hour, preferably 10 minutes to 30 minutes, and is then brought to the external pressure with an inert gas. 0.01 to 1% by weight, relative to the amount of polyether which remains, of an organic carboxylic acid halide, preferably benzoyl chloride, is then added and the mixture is subsequently stirred at 60°–160° C., preferably 70°–120° C., for 1 to 30 minutes, preferably 5–10 minutes. The amount of OH equivalents which remain is determined titrimetrically on a sample. The required amount of active compound, if necessary dissolved in a suitable solvent, is then added in a ratio, of OH equivalents of the polyether:equivalents of H atoms in the active compound that are active in Zerewitinoff reactions, of 1:1. The mixture is homogenized and the required amount of diisocyanate is then added dropwise, in the equivalent ratio, of the sum of equivalents of H atoms that are active in Zerewitinoff reactions:sum of all the NCO equivalents, of 1:1. The mixture is subsequently stirred at 60°–120° C. for 10 minutes to 48 hours, with exclusion of moisture. If appropriate, the solvent is then stripped off in vacuo. The modified active compound has the ideal formula

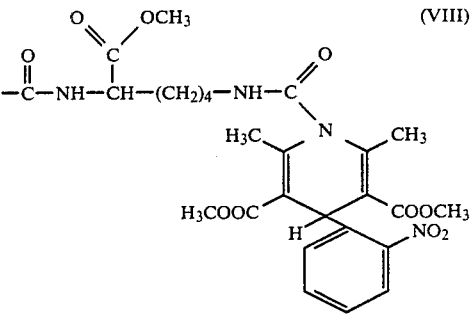
(VIII)

in which p, q and r have the meanings indicated above.

A further possibility for the preparation of the active compounds according to the invention consists in using a polyether with a terminal N-(isocyanatophenyl)-urethane group, which is obtained by known processes from a polyether with a terminal hydroxyl group by reaction with n-nitrophenyl isocyanate, subsequent reduction of the nitro group to the amino group and subsequent phosgenation, and an active compound with a hydrogen atom that is active in Zerewitinoff reactions.

The procedure followed in carrying out this process is appropriately analogous to that described above in the case where polyether-isocyanates are used.

If, for example, an ethylene oxide polyether, started from n-butanol, which had been converted to the polyether-isocyanate by reaction with p-nitrophenyl isocyanate and then by reduction and phosgenation, and 2-isopropoxyphenyl N-methylcarbamate are used, the new modified active compound formed by the process according to the invention has the general ideal formula

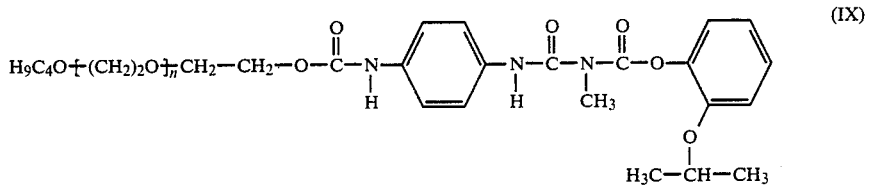
(IX)

wherein n has the meaning indicated above.

As already mentioned, the active compounds modified by the process according to the invention have a better solubility in water or lower aliphatic alcohols than the non-modified active compounds. They can thus be employed in a more simple and less expensive manner, since no solubilizing agents, or a smaller amount of solubilizing agents, are required to prepare the ready-to-use agents.

The improved solubility in water also has the effect that active compounds which could not hitherto be employed systemically in the field of plant protection can also be employed systemically, since they can now be transported by the flow of sap in the plants.

The preparative examples which follow illustrate the process according to the invention with the aid of examples in which ethylene oxide polyethers started from butanol were used as starting component A. However it is not intended that the present invention shall be restricted to these samples and procedures. The products prepared according to the invention and disclosed in Examples 9 to 151 are all new.

PREPARATIVE EXAMPLES

Example 1(a)

600 g (0.3 mol) of a monofunctional ethylene oxide polyether started from n-butanol and having an average molecular weight of 2,000 (average number of ethylene oxide units n=43) and an OH number of 27.6 were stirred under 20 mbars and at 120° C., for 30 minutes, whereby any traces of water which may have been present were removed. Flushing with dry nitrogen was then carried out and 3 ml of benzoyl chloride were added. The mixture was evacuated once more to 20 mbars and flushing with nitrogen was then again carried out. The mixture was allowed to cool to 90° C. and 63.7 g (0.3 mol) of 1,6-diisocyanatohexanoic acid methyl ester were then added. After 25 minutes, the NCO content had fallen to the calculated value of 1.9% by weight. The mixture was cooled and 662 g of a whitish-yellow product of the ideal formula

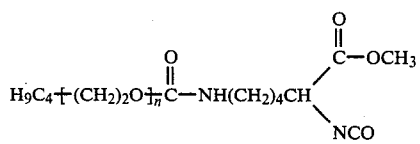

in which n=43 were obtained. This product could be reacted, without further purification, with compounds which are reactive towards the remaining NCO group.

Example 1(b)

600 g (0.3 mol) of the monofunctional ethylene oxide polyether started from n-butanol and having an average molecular weight of 2,000 (average number of ethylene oxide units n=43) and an OH number of 27.6 were reacted with 50.5 g (0.3 mol) of hexamethylenediisocyanate analogously to Example 1(a). After 18 minutes, the NCO content had fallen to the calculated value of 1.9% by weight. 648 g of a grey-yellow product of the ideal formula

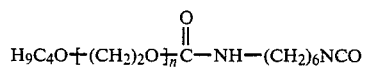

in which n=43.

Example 1(c)

600 g (0.3 mol) of a monofunctional ethylene oxide polyether started from n-butanol and having an average molecular weight of 2,000 (average number of ethylene oxide units n=43) and an OH number of 27.6 were heated to 130° C. together with 0.033 g (0.005% by weight) of di-n-butyl-tin oxide and 52.2 g (0.3 mol) of adipic acid dimethyl ester. About 4 g of methanol passed over at this temperature in the course of 2 hours. The temperature was increased to 225° C. in the course of 2 hours. When this temperature had been reached, the mixture was subsequently stirred until no further methanol passed over (20 minutes) and was then allowed to cool. 641 g of a dark yellow product of the ideal formula

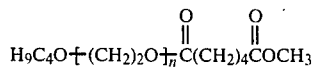

in which n=43 were obtained.

Example 2(a)

600 g (0.6 mol) of a monofunctional ethylene oxide polyether started from n-butanol and having an average molecular weight of 1,002 (average number of ethylene oxide units n=21) and an OH number of 56 were stirred under 20 mbars and at 120° C. for 30 minutes, whereby any traces of water which may have been present were removed. Flushing with dry nitrogen was then carried out and 3 ml of benzoyl chloride were added. The mixture was evacuated once more to 20 mbars and flushing with nitrogen was then again carried out. The mixture was allowed to cool to 90° C. and 127.3 g (0.6 mol) of 1,6-diisocyanatohexanoic acid methyl ester were then added. After 18 minutes, the NCO content had fallen to the calculated value of 3.5% by weight. The mixture was cooled and 721 g of yellow product of the ideal formula

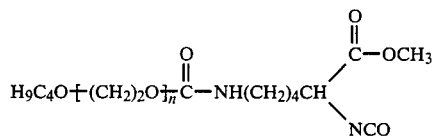

in which n=21 were obtained. This product could be reacted without further purification, with compounds which are reactive towards the remaining NCO group.

Example 2(b)

600 g (0.6 mol) of a monofunctional ethylene oxide polyether started from n-butanol and having an average molecular weight of 1,002 (average number of ethylene oxide units n=21) and an OH number of 56 were reacted with 101 g (0.6 mol) of hexamethylene diisocyanate analogously to Example 2(a). After 16 minutes, the NCO content had fallen to the calculated value of 3.6% by weight. 694 g of a grey-yellow soap-like product of the ideal formula

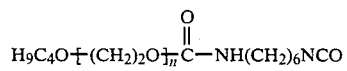

in which n=21 were obtained.

Example 3(a)

470 g (0.6 mol) of a monofunctional ethylene oxide polyether started from n-butanol and having an average molecular weight of 784 (average number of ethylene oxide units n=16) and an OH number of 71.6 were stirred under 20 mbars and at 120° C. for 30 minutes, whereby any traces of water which may have been present were removed. Flushing with dry nitrogen was then carried out and 3 ml of benzoyl chloride were added. The mixture was evacuated once more to 20 mbars and flushing with nitrogen was then again carried out. The mixture was allowed to cool to 85° C. and 127.3 g (0.6 mol) of 1,6-diisocyanatohexanoic acid methyl ester were then added. After 17 minutes, the NCO content had fallen to the calculated value of 4.2% by weight. The mixture was cooled and 593 g of a white product of the ideal formula

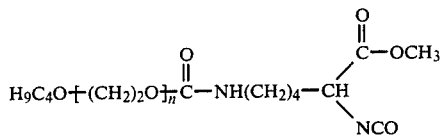

in which n=16 were obtained. This product could be reacted, without further purification, with compounds which are reactive towards the remaining NCO group.

Example 3(b)

470 g (0.6 mol) of a monofunctional ethylene oxide polyether started from n-butanol and having an average molecular weight of 784 (average number of ethylene oxide units n=16) and an OH number of 71.6 were reacted with 101 g (0.6 mol) of hexamethylene diisocyanate analogously to Example 3(a). After 12 minutes, the NCO content had fallen to the calculated value of 4.4% by weight. 564 g of a pale yellow soap-like product of the ideal formula

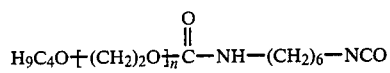

in which n=16 were obtained.

Example 3(c)

470 g (0.6 mol) of a monofunctional ethylene oxide polyether started from n-butanol and having an average molecular weight of 784 (average number of ethylene oxide units n=16) and an OH number of 71.6 were reacted with 52.2 g (0.3 mol) of adipic acid dimethyl ester in the presence of 0.05 g of di-n-butyl-tin oxide analogously to Example 1(c). Total reaction time: 2.5 hours.

521 g of a highly viscous, red-yellow liquid product of the ideal formula

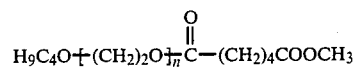

in which n=16 were obtained.

Example 4

312 g (0.6 mol) of a monofunctional ethylene oxide polyether started from n-butanol and having an average molecular weight of 519 (average number of ethylene oxide units n=10) and an OH number of 108 were stirred under 20 mbars and at 120° C. for 30 minutes, whereby any traces of water which may have been present were removed. Flushing with dry nitrogen was then carried out and 2 ml of benzoyl chloride were added. The mixture was evacuated once more to 20 mbars and flushing with nitrogen was then again carried out. The mixture was allowed to cool to 80° C. and 127.3 g (0.6 mol) of 1,6-diisocyanatohexanoic acid methyl ester were then added. After 9 minutes, the NCO content had fallen to the calculated value of 5.74% by weight. The mixture was cooled and 431 g of a yellowish, liquid product of the ideal formula

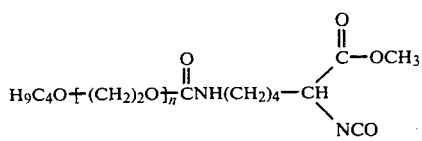

in which n=10 were obtained. The product could be reacted, without further purification, with compounds which are reactive towards the remaining NCO group.

Example 5

162.2 g (1.0 mol) of 2-(2-butoxyethoxy)-ethanol were stirred under 20 mbars and at 80° C. for 30 minutes, whereby any traces of moisture which may have been present were removed. Flushing with dry nitrogen was then carried out and 1 ml of benzoyl chloride was added. The mixture was evacuated once more to 20 mbars and flushing with nitrogen was then again carried out. The mixture was allowed to cool to 75° C. and 212.2 g (1.0 mol) of 1,6-diisocyanatohexanoic acid methyl ester were then added. After 8 minutes, the NCO content had fallen to the calculated value of 11.2% by weight. The mixture was cooled and 371 g of a colorless, liquid product of the ideal formula

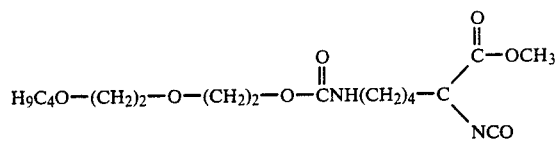

were obtained. The product could be reacted, without further purification, with compounds which are reactive towards the remaining NCO group.

Example 6

134.2 g (1.0 mol) of 2-(2-ethoxyethoxy)-ethanol were stirred under 20 mbars and at 80° C. for 30 minutes, whereby any traces of moisture which may have been present were removed. Flushing with dry nitrogen and then carried out and 1 ml of benzoyl chloride was added. The mixture was evacuated once more to 20 mbars and flushing with nitrogen was then again carried out. The mixture was allowed to cool to 70° C. and 212.2 g (1.0 mol) of 1,6-diisocyanatohexanoic acid methyl ester were then added. After 12 minutes, the NCO content had fallen to the calculated value of 12.1% by weight. The mixture was cooled and 339 g of a colorless, liquid product of the ideal formula

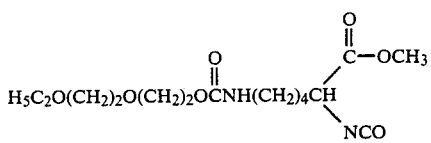

were obtained. The product could be reacted, without further purification, with compounds which are reactive towards the remaining NCO group.

Example 7

120.1 g (1.0 mol) of 2-(2-methoxyethoxy)-ethanol were stirred under 20 mbars and at 80° C. for 30 minutes, whereby any traces of moisture which may have been present were removed. Flushing with dry nitrogen was then carried out and 1 ml of benzoyl chloride was added. The mixture was evacuated once more to 20 mbars and flushing with nitrogen was then again carried out. The mixture was allowed to cool to 70° C. and 212.2 g (1.0 mol) of 1,6-diisocyanatohexanoic acid methyl ester were then added. After 10 minutes, the NCO content had fallen to the calculated value of 12.6% by weight. The mixture was cooled and 227 g of a colorless, liquid product of the ideal formula

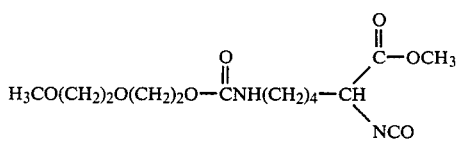

were obtained. The product could be reacted, without further purification, with compounds which are reactive towards the remaining NCO group.

Example 9

148.2 g (1.0 mol) of 1,3-diethoxy-2-propanol were stirred under 20 mbars and at 90° C. for 20 minutes, whereby any traces of moisture which may have been present were removed. Flushing with dry nitrogen was then carried out and 1 ml of benzoyl chloride was added. The mixture was evacuated once more to 20 mbars and flushing with nitrogen was then again carried out. The mixture was allowed to cool 65° C. and 212.2 g (1.0 mol) of 1,6-diisocyanatohexanoic acid methyl ester were then added. After 20 minutes, the NCO content had fallen to the calculated value of 11.7% by weight. The mixture was cooled and 351 g of a yellowish, liquid product of the ideal formula

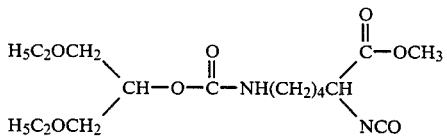

were obtained. The product could be reacted, without further purification, with compounds which are reactive towards the remaining NCO group.

EXAMPLE 9

22.1 g (0.01 mol) of the compound obtained according to Example 1(a) were dissolved in 50 ml of absolute toluene (solution 1) and 3.4 g (0.01 mol) of 1,3-di-p-chlorophenyl-(1H,2H,3H,4H,5H, 6H)-triazine-2,4-dione were dissolved in 50 ml of absolute acetone (solution 2). Solution 1 was initially introduced at 40° C. and solution 2 was then added dropwise very slowly, the mixture being stirred rapidly. The acetone was then stripped off at 40° C. and under 200–300 mbars. Flushing with dry nitrogen was carried out. A further 200 ml of absolute toluene were then added and the mixture was boiled under reflux, with exclusion of moisture, until the band at 2,270 cm$^{-1}$ belonging to the NCO group, in the IR spectrum, was negligibly small (1 hour). The toluene was then distilled off, first under normal pressure and then under a waterpump vacuum.

25.5 g of a solid with a softening point of 46°–50° C. were obtained as the residue. This active compound modified according to the invention was very readily soluble in water and/or lower alcohols and had the ideal formula

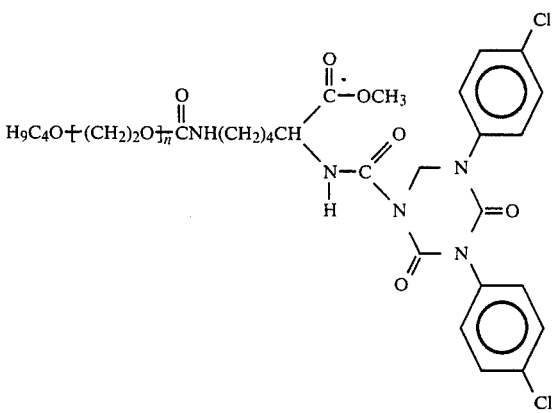

in which n=43.

EXAMPLE 10

12.0 g (0.01 mol) of the compound obtained according to Example 2(a) were dissolved in 50 ml of absolute toluene (solution 1). 3.4 g (0.01 mol) of 1,3-di-p-chlorophenyl-(1H,2H,3H,4H,5H,6H)-S-triazine-2,4-dione were dissolved in 50 ml of absolute acetone (solution 2). Solution 1 was initially introduced at 40° C. and solution 2 was then added dropwise very slowly, the mixture being stirred rapidly. The acetone was then stripped off at 40° C. and under 200–300 mbars. Flushing with dry nitrogen was carried out. A further 200 ml of absolute toluene were then added and the mixture was boiled under reflux, with exclusion of moisture, until the band at 2,270 cm$^{-1}$ belonging to the NCO group, in the IR spectrum, had become negligibly small (50 minutes). The toluene was then distilled off, first under normal pressure and then under a waterpump vacuum.

15.4 g of a solid which was wax-like at room temperature were obtained as the residue. This active compound modified according to the invention was readily soluble in water and/or lower alcohols and had the ideal formula

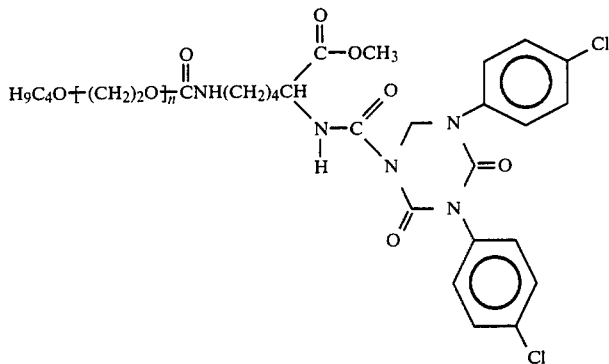

in which n=21.

EXAMPLE 11

9.9 g (0.01 mol) of the compound obtained according to Example 3(a) were initially introduced in the molten form at 50° C. 3.4 g (0.01 mol) of 1,3-di-p-chlorophenyl-(1H,2H,3H,4H,5H,6H)-triazine-2,4-dione were dissolved in 150 ml of absolute acetone and the solution was then added dropwise to the first compound, while stirring vigorously. The acetone was stripped off under 200–300 mbars and flushing with dry nitrogen was then carried out. The mixture was stirred at 90° C. until the band at 2,270 cm$^{-1}$ belonging to the NCO group, in the IR spectrum, had become negligibly small (50 minutes). 13.3 g of a golden yellow-colored liquid were obtained. This active compound modified according to the invention was readily soluble in water and/or lower alcohols and had the ideal formula

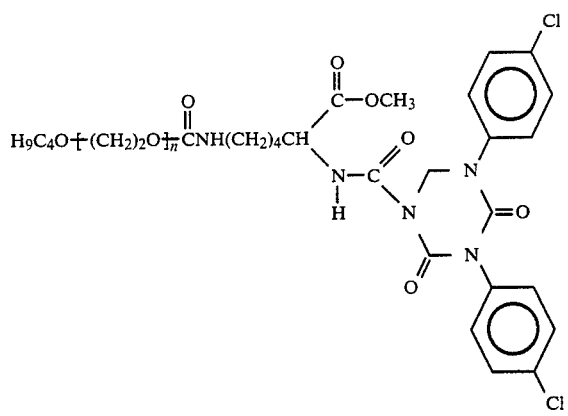

in which n=16.

EXAMPLE 12

7.3 g (0.01 mol) of the compound obtained according to Example 4 were introduced into a flask at 40° C. 3.4 g (0.01 mol) of 1,3-di-p-chlorophenyl-(1H,2H,3H,4H,5H,6H)-triazine-2,4dione, dissolved in 150 ml of absolute acetone, were added dropwise to this compound, while stirring vigorously. The acetone was then stripped off again under 200–300 mbars and the flask was flushed with dry nitrogen. The mixture was stirred at 70° C. for 2.5 hours, with exclusion of moisture. After this time, the band at 2,270 cm$^{-1}$ belonging to the NCO group, in the IR spectrum, had become negligibly small.

10.7 g of a golden yellow-colored liquid were obtained. This active compound modified according to the invention was readily soluble in water and/or lower alcohols and had the ideal formula

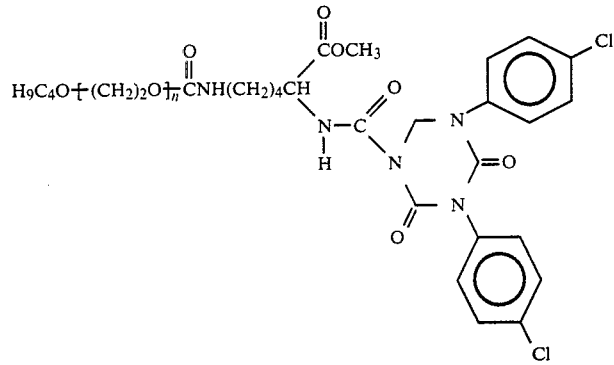

in which n=10.

EXAMPLE 13

7.5 g (0.02 mol) of the compound obtained according to Example 5 were initially introduced at 50° C. 6.7 g (0.02 mol) of 1,3-di-p-chlorophenyl-(1H,2H,3H,4H,5H,6H)-triazine-2,4-dione, dissolved in 150 ml of absolute acetone, were added dropwise to this compound, while stirring vigorously. The acetone was then stripped off again under 200–300 mbars and flushing with dry nitrogen was carried out. The mixture was stirred at 75° C. for 120 minutes, with exclusion of moisture; the band at 2,270 cm$^{-1}$ belonging to the NCO group, in the IR spectrum, had then become negligibly small.

14.2 g of a yellow-colored viscous liquid were obtained. This active compound modified according to the invention was readily soluble in water and/or lower alcohols and had the ideal formula

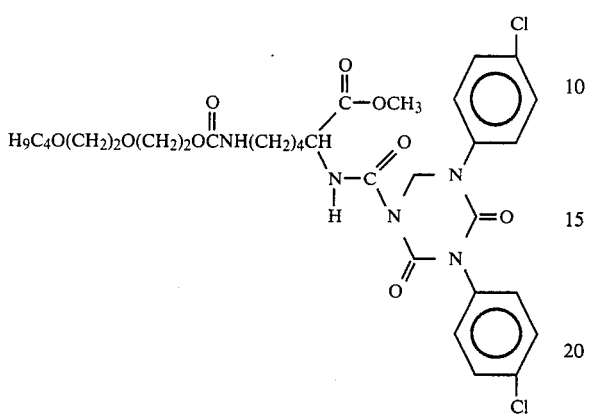

EXAMPLE 14

6.9 g (0.02 mol) of the compound obtained according to Example 6 were reacted with 6.7 g (0.02 mol) of 1,3-di-p-chlorophenyl-(1H,2H,3H,4H,5H,6H)-triazine-2,4-dione, analogously to Example 13. Subsequent stirring time: 140 minutes at 70° C.

13.6 g of a yellow-colored viscous liquid were obtained. This active compound modified according to the invention was moderately soluble in water but soluble in lower alcohols and had the ideal formula

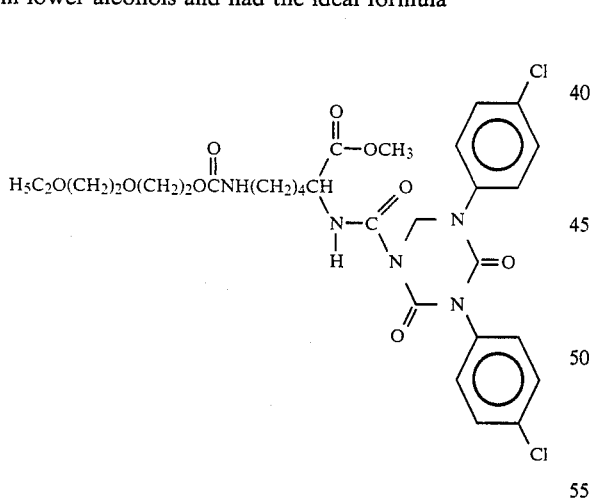

EXAMPLE 15

6.6 g (0.02 mol) of the compound obtained according to Example 7 were reacted with 6.7 g (0.02 mol) of 1,3-di-p-chlorophenyl-(1H,2H,3H,4H,5H,6H)-triazine-2,4-dione analogously to Example 13. Subsequent stirring time: 110 minutes at 80° C.

13.3 g of a dark yellow viscous liquid were obtained. This active compound modified according to the invention was moderately soluble in water but soluble in lower alcohols and had the ideal formula

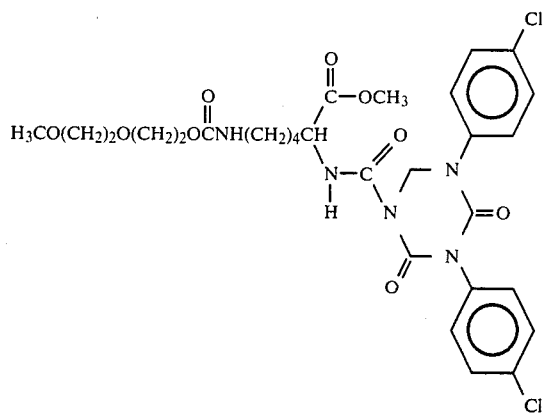

EXAMPLE 16

7.2 (0.02 mol) of the compound obtained according to Example 8 were reacted with 6.7 g (0.02 mol) of 1,3-di-p-chlorophenyl-(1H,2H,3H,4H,5H,6H)-triazine-2,4-dione analogously to Example 13. Subsequent stirring time: 120 minutes at 75° C.

13.9 g of a yellow-red viscous liquid were obtained. This active compound modified according to the invention was readily soluble in water as well as methanol and had the ideal formula

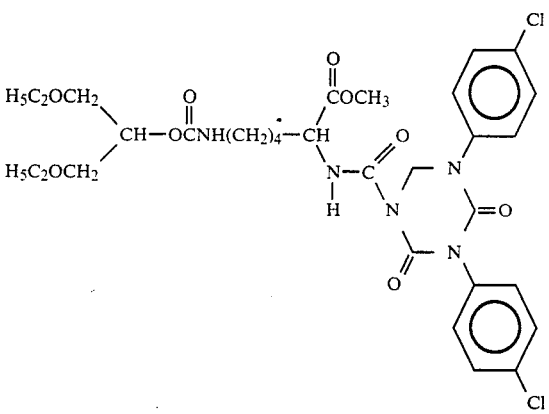

EXAMPLE 17

100 g (0.045 mol) of the compound obtained according to Example 1(a) were reacted with 12.0 g (0.045 mol) of 1,3-diphenyl-(1H,2H,3H,4H,5H,6H)-triazine-2,4-dione analogously to Example 9. Subsequent stirring time: 110 minutes at 110° C.

112 g of a wax-like solid were obtained. This active compound modified according to the invention was very readily soluble in water and/or lower alcohols and had the ideal formula

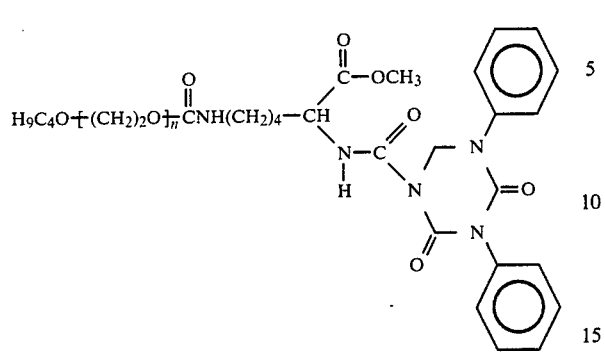

in which n=43.

EXAMPLE 18

12.0 g (0.01 mol) of the compound obtained according to Example 2(a) were reacted with 2.7 g (0.01 mol) of 1,3-diphenyl-(1H,2H,3H,4H,5H,6H)-triazine-2,4-dione analogously to Example 10. Subsequent stirring time: 110 minutes at 110° C.

14.7 g of a wax-like solid were obtained. This active compound modified according to the invention was very readily soluble in water and/or lower alcohols and had the ideal formula

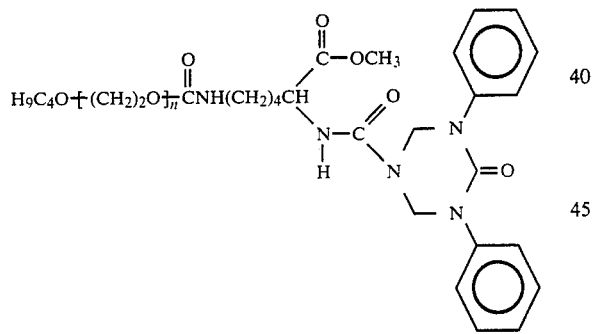

in which n=21.

EXAMPLE 19

9.9 g (0.01 mol) of the compound obtained according to Example 3(a) were reacted with 2.7 g (0.01 mol) of 1,3-diphenyl-(1H,2H,3H,4H,5H,6H)-triazine-2,4-dione analogously to Example 11. Subsequent stirring time: 100 minutes at 90° C.

12.6 g of a wax-like solid were obtained. This active compound modified according to the invention was very readily soluble in water and/or lower alcohols and had the ideal formula

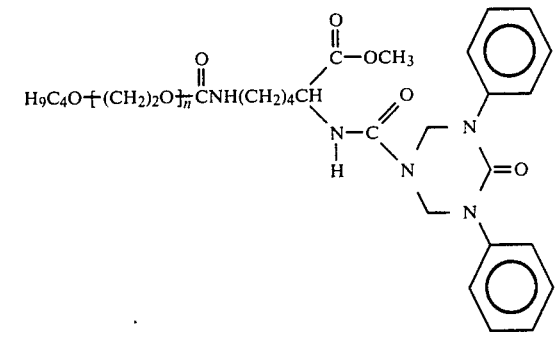

in which n=16.

EXAMPLE 20

7.3 g (0.01 mol) of the compound obtained according to Example 4 were reacted with 2.7 g (0.01 mol) of 1,3-diphenyl-(1H,2H,3H,4 H,5H,6H)-triazine-2,4-dione analogously to Example 12. Subsequent stirring time: 120 minutes at 70° C.

10.0 g of a golden yellow viscous liquid were obtained. This active compound modified according to the invention was very readily soluble in water and/or lower alcohols and had the ideal formula

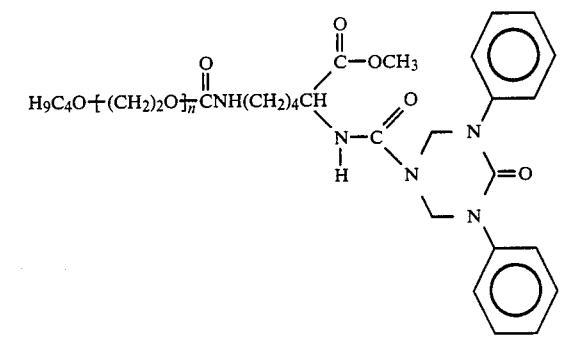

in which n=10.

EXAMPLE 21

110.6 g (0.05 mol) of the compound obtained according to Example 1(a) were reacted with 7.2 g (0.05 mol) of 1,3-dimethyl-(1H,2H,3H,4H,5H,6H)-triazine-2,6-dione analogously to Example 9. Subsequent stirring time: 140 minutes at 110° C.

117 g of a whitish-yellow, wax-like solid were obtained. This new active compound modified according to the invention was very readily soluble in water and/or lower alcohols and had the ideal formula

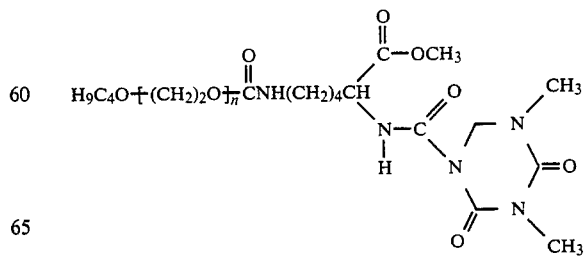

in which n=43.

EXAMPLE 22

12.0 g (0.01 mol) of the compound obtained according to Example 2(a) were reacted with 1.43 g (0.01 mole) of 1,3-dimethyl-(1H,2H,3H,4H,5H,6H)-triazine-2,4-dione analogously to Example 10. Subsequent stirring time: 110 minutes at 110° C.

13.4 g of a yellow wax-like substance were obtained. This active compound modified according to the invention was very readily soluble in water and/or lower alcohols and had the ideal formula

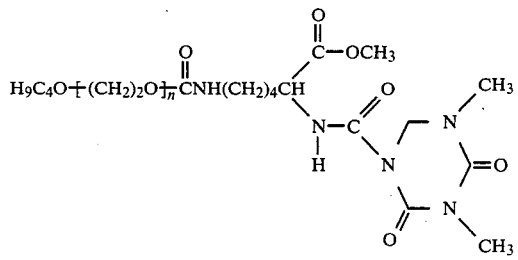

in which n=21.

EXAMPLE 23

9.9 g (0.01 mol) of the compound obtained according to Example 3(a) were reacted with 1.43 g (0.01 mol) of 1,3-dimethyl-(1H,2H,3H,4H,5H,6H)-triazine-2,4-dione analogously to Example 11. Subsequent stirring time: 60 minutes at 90° C.

11.3 g of a yellow viscous liquid were obtained. This active compound modified according to the invention was very readily soluble in water and/or lower alcohols and had the ideal formula

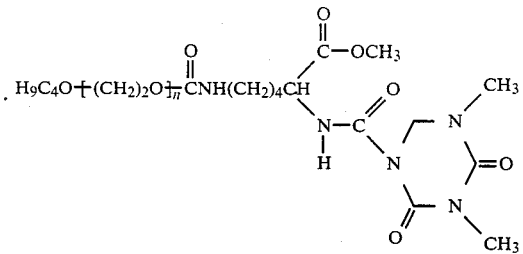

in which n=16.

EXAMPLE 24

7.3 g (0.01 mol) of the compound obtained according to Example 4 were reacted with 1.43 g (0.01 mol) of 1,3-dimethyl-(1H,2H,3H,4H,5H,6H)-triazine-2,4-dione analogously to Example 12. Subsequent stirring time: 70 minutes at 70° C.

8.9 g of a golden yellow viscous liquid were obtained. This active compound modified according to the invention was very readily soluble in water and/or lower alcohols and had the ideal formula

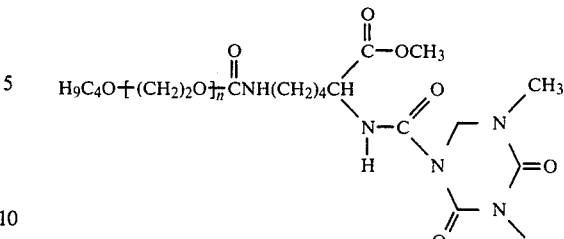

in which n=10.

EXAMPLE 25

100 g (0.045 mol) of the compound obtained according to Example 1(a) were reacted with 9.6 g (0.045 mol) of 4-amino-6-tert.-butyl-3-(methylthio)-1,2,4-triazin-5-(4H)-one analogously to Example 9. Subsequent stirring time: 180 minutes at 110° C.

109.6 g of a yellow solid were obtained. This new active compound modified according to the invention was very readily soluble in water and/or lower alcohols and had the ideal formula

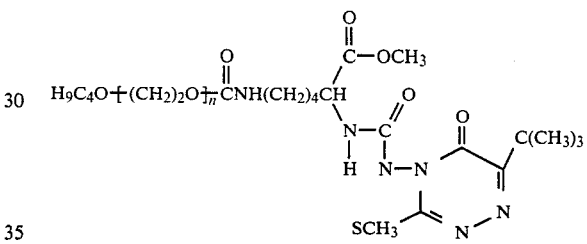

in which n=43.

EXAMPLE 26

60.6 g (0.05 mol) of the compound obtained according to Example 2(a) were reacted with 10.7 g (0.05 mol) of 4-amino-6-tert.-butyl-3-(mehylthio)-1,2,4-triazin-5-(4H)-one analogously to Example 10. Subsequent stirring time: 105 minutes at 110° C.

71.3 g of a yellow, deliquescent product were obtained. This active compound modified according to the invention was very readily soluble in water and/or lower alcohols and had the ideal formula

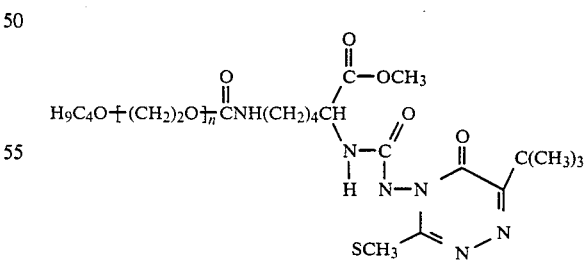

in which n=21.

EXAMPLE 27

49.6 g (0.05 mol) of the compound obtained according to Example 3(a) were reacted with 10.7 g (0.05 mol) of 4-amino-6-tert.-butyl-3-(methylthio)-1,2,4-triazin-5-(4H)-one analogously to Example 11. Subsequent stirring time: 115 minutes at 90° C.

60.3 g of a dark yellow highly viscous liquid were obtained. This active compound modified according to the invention was readily soluble in water and/or lower alcohols and had the ideal formula

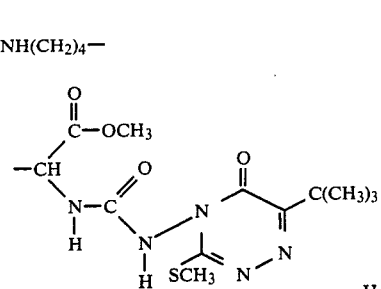

in which n=16.

EXAMPLE 28

36.6 g (0.05 mol) of the compound obtained according to Example 4 were reacted with 10.7 g (0.05 mol) of 4-amino-6-tert.-butyl-3(methylthio)-1,2,4-triazin-5-(4H)-one analogously to Example 12. Subsequent stirring time: 140 minutes at 70° C.

47.3 g of a red-yellow viscous liquid were obtained. This active compound modified according to the invention was readily soluble in water and/or lower alcohols and had the ideal formula

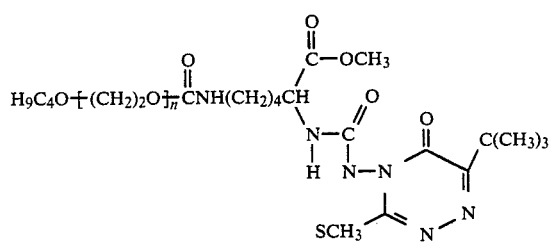

in which n=10.

EXAMPLE 29

18.7 g (0.05 mol) of the compound obtained according to Example 5 were reacted with 10.7 g (0.05 mol) of 4-amino-6-tert.-butyl-3-(methylthio)-1,2,4-triazin-5-(4H)-one analogously to Example 13. Subsequent stirring time: 12 hours at 75° C.

29.2 g of a dark yellow, highly viscous liquid were obtained. This active compound modified according to the invention was readily soluble in water and/or the lower alcohols and had the ideal formula

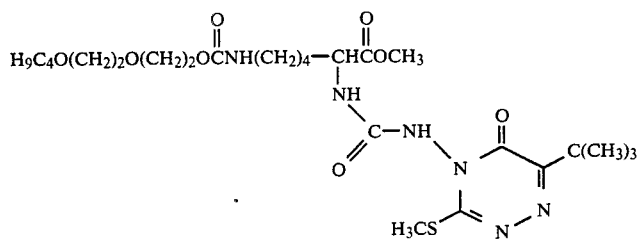

EXAMPLE 30

17.3 g (0.05 mol) of the compound obtained according to Example 6 were reacted with 10.7 g (0.05 mol) of 4-amino-6-tert.-butyl-3-(methylthio)-1,2,4-triazin-5-(4H)-one analogously to Example 13. Subsequent stirring time: 16 hours at 75° C.

27.4 g of a pale yellow, viscous liquid were obtained. This active compound modified according to the invention was readily soluble in water and methanol and had the ideal formula

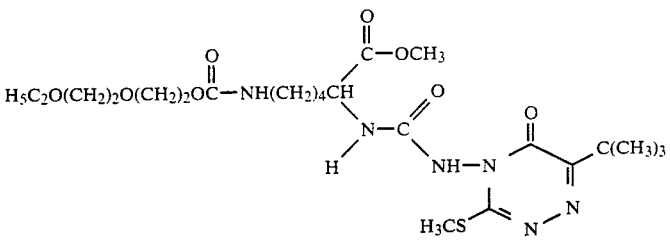

EXAMPLE 31

16.6 g (0.05 mol) of the compound obtained according to Example 7 were reacted with 10.7 g (0.05 mol) of 4-amino-6-tert.-butyl-3-(methylthio)-1,2,4-triazin-5-(4H)-one analogously to Example 13. Subsequent stirring time: 21 hours at 75° C.

26 g of a yellow, viscous liquid were obtained. This active compound modified according to the invention was readily soluble in water and/or methanol and had the ideal formula

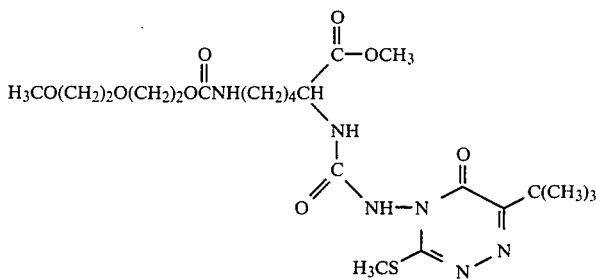

EXAMPLE 32

18.0 g (0.05 mol) of the compound obtained according to Example 8 were reacted with 10.7 g (0.05 mol) of 4-amino-6-tert.-butyl-3-(methylthio)-1,2,4-triazin-5-(4H)-one analogously to Example 13. Subsequent stirring time: 3 hours at 80° C.

27.4 g of a golden yellow, viscous liquid were obtained. This active compound modified according to the invention was readily soluble in water and/or methanol and ethanol and had the ideal formula

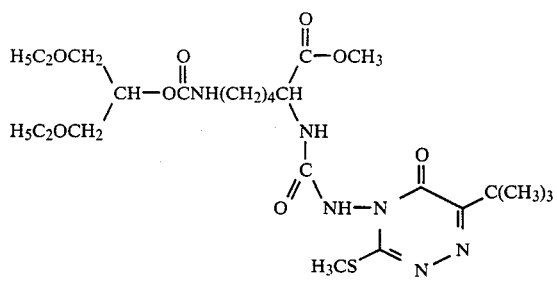

EXAMPLE 33

22.1 g (0.01 mol) of the compound obtained according to Example 1(a) were reacted with 3.5 g (0.01 mol) of N,N'-bis-[3,4-dichlorophenyl]-urea analogously to Example 9. Subsequent stirring time: 22 hours at 110° C.

24.9 g of a pale yellow solid were obtained. This active compound modified according to the invention was readily soluble in water and lower alcohols and had the ideal formula

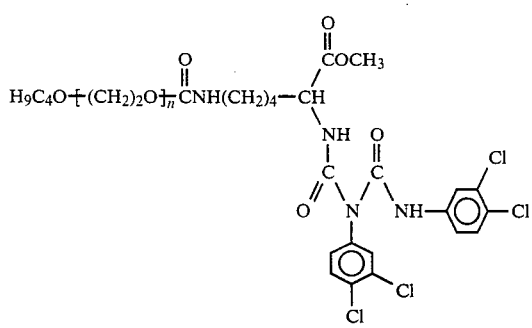

in which n=43.

EXAMPLE 34

12.1 g (0.01 mol) of the compound obtained according to Example 2(a) were reacted with 3.5 g (0.01 mol) of N,N'-bis-[3,4-dichlorophenyl]-urea analogously to Example 10. Subsequent stirring time: 95 minutes at 110° C.

14 g of a pale yellow solid were obtained. This active compound modified according to the invention was readily soluble in water and methanol and had the ideal formula

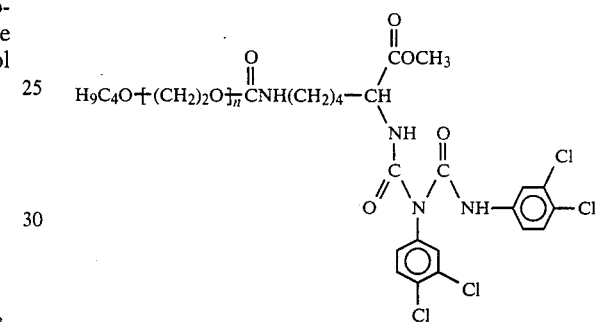

in which n=21.

EXAMPLE 35

9.9 g (0.01 mol) of the compound obtained according to Example 3(a) were reacted with 3.5 g (0.01 mol) of N,N'-bis-(3,4-dichlorophenyl)-urea analogously to Example 11. Subsequent stirring time: 5 hours of 90° C.

12.1 g of a yellow, soap-like solid were obtained. This active compound modified according to the invention was readily soluble in water and methanol and had the ideal formula

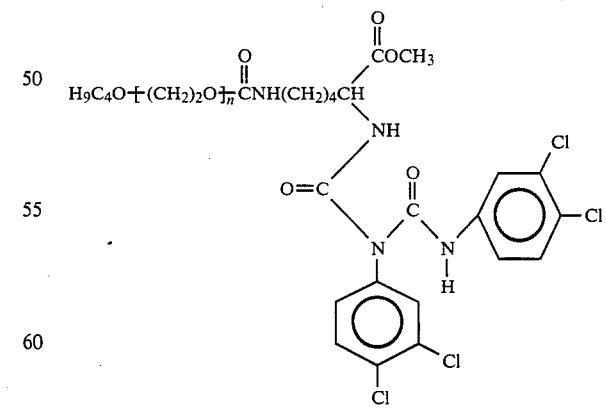

in which n=16.

EXAMPLE 36

7.3 g (0.01 mol) of the compound obtained according to Example 4 were reacted with 3.5 g (0.01 mol) of N,N'-bis-[3,4-dichlorophenyl]-urea analogously to Example 12. Subsequent stirring time: 6 hours at 70° C.

10.2 g of a dark yellow, viscous liquid were obtained. This active compound modified according to the invention was readily soluble in water and/or methanol and ethanol and had the ideal formula

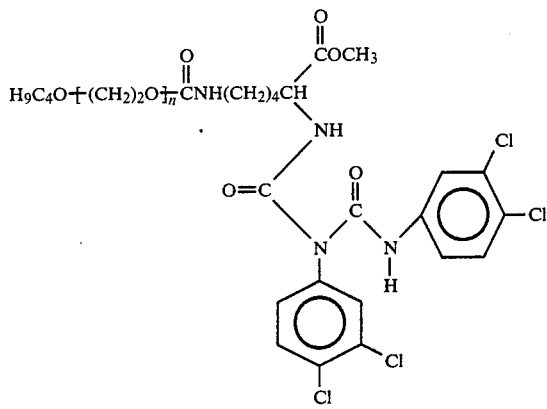

in which n=10.

EXAMPLE 37

7.3 g (0.01 mol) of the compound obtained according to Example 4 were reacted with 3.2 g (0.01 mol) of N-p-chlorophenyl-N'-o,o'-dichlorophenylurea analogously to Example 12. Subsequent stirring time: 14 hours at 70° C.

9.8 g of a light brown, viscous liquid were obtained. This active compound modified according to the invention was readily soluble in water and methanol and had the ideal formula in which n=10.

EXAMPLE 38

7.3 g (0.01 mol) of the compound obtained according to Example 4 were reacted with 1.5 g (0.01 mol) of phenylthiourea analogously to Example 12. Subsequent stirring time: 2 hours at 75° C.

7.8 g of a reddish-yellow, viscous liquid were obtained. This active compound modified according to the invention was readily soluble in water and/or lower alcohols and had the ideal formula in which n=10.

EXAMPLE 39

22.1 g (0.01 mol) of the compound obtained according to Example 1(a) were reacted with 2.0 g (0.01 mol) of α-naphthylthiourea analogously to Example 9. Subsequent stirring time: 3 hours at 110° C.

23.4 g of a yellow-brown solid were obtained. This active compound modified according to the invention was readily soluble in water and methanol and had the ideal formula in which n=43.

EXAMPLE 40

22.1 g (0.01 mol) of the compound obtained according to Example 1(a) were reacted with 2.9 g (0.01 mol) of N,N-dimethyl-N'-[p-(p-chlorophenoxy)phenyl]-urea analogously to Example 9. Subsequent stirring time: 6 hours at 110° C.

23.8 g of a dark yellow solid were obtained. This active compound modified according to the invention was readily soluble in water and methanol and had the ideal formula in which n=43.

EXAMPLE 41

22.1 g (0.01 mol) of the compound obtained according to Example 1(a) were reacted with 2.3 g (0.01 mol) of N-(3-trifluoromethylphenyl)-N',N'-dimethylurea analogously to Example 9. Subsequent stirring time: 8 hours at 110° C.

23.9 g of a dark yellow solid were obtained. This active compound modified according to the invention was readily soluble in water and/or lower alcohols and had the ideal formula

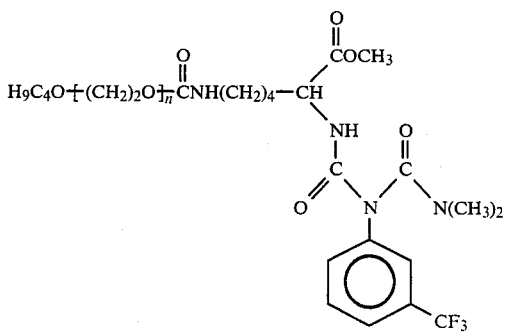

in which n=43.

EXAMPLE 42

22.1 g (0.01 mol) of the compound obtained according to Example 1(a) were reacted with 2.1 g (0.01 mol) of N-(4-chlorophenyl)-N'-methoxy-N'-methylurea analogously to Example 9. Subsequent stirring time: 5 hours at 115° C.

23.7 g of a pale yellow solid were obtained. This active compound modified according to the invention was readily soluble in water and/or methanol and ethanol and had the ideal formula

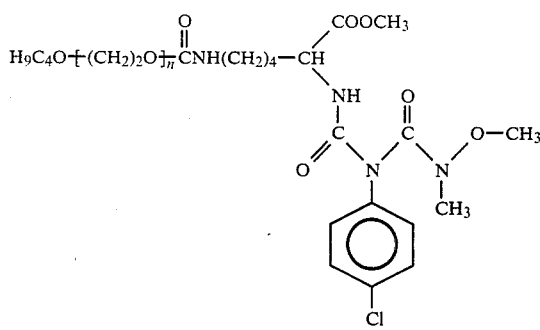

in which n=43.

EXAMPLE 43

22.1 g (0.01 mol) of the compound obtained according to Example 1(a) were reacted with 2.1 g (0.01 mol) of N-(2-benzothiazolyl)-N'-methylurea analogously to Example 9. Subsequent stirring time: 6 hours at 110° C.

24.0 g of a golden yellow solid were obtained. This active compound modified according to the invention was readily soluble in water and/or methanol and had the ideal formula

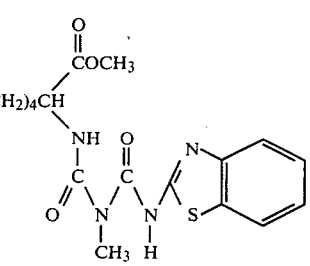

in which n=43.

EXAMPLE 44

14.6 g (0.02 mol) of the compound obtained according to Example 4 were reacted with 2.8 g (0.02 mol) of phenylurea analogously to Example 12. Subsequent stirring time: 14 hours at 70° C.

15.2 g of a brown-yellow solid were obtained. This active compound modified according to the invention was readily soluble in water and/or lower alcohols and had the ideal formula

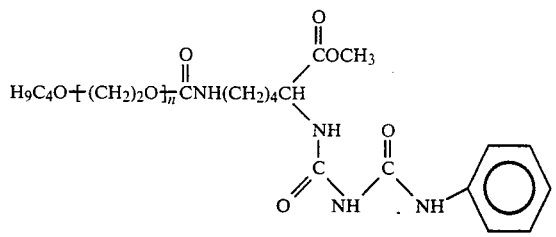

in which n=10.

EXAMPLE 45

12.1 g (0.01 mol) of the compound obtained according to Example 2(a) were reacted with 2.9 g (0.01 mol) of N-(4-bromo-3-chlorophenyl)-N'-methoxy-N'-methylurea analogously to Example 10. Subsequent stirring time: 16 hours at 95° C.

14.7 g of a dark brown solid were obtained. This active compound modified according to the invention was readily soluble in water and lower alcohols and had the ideal formula

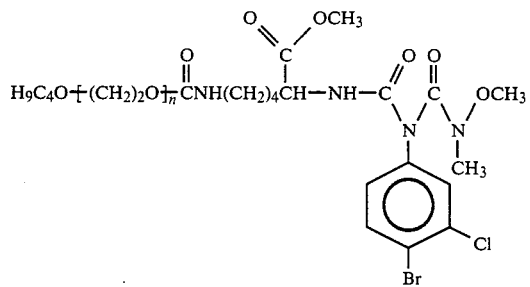

in which n=21.

EXAMPLE 46

12.1 g (0.01 mol) of the compound obtained according to Example 2(a) were reacted with 1.9 g (0.01 mol) of N-3-tolyl-N',N'-dimethylurea analogously to Example 10. Subsequent stirring time: 12 hours at 105° C.

13.8 g of a yellow solid were obtained. This active compound modified according to the invention was readily soluble in water and lower alcohols and had the ideal formula

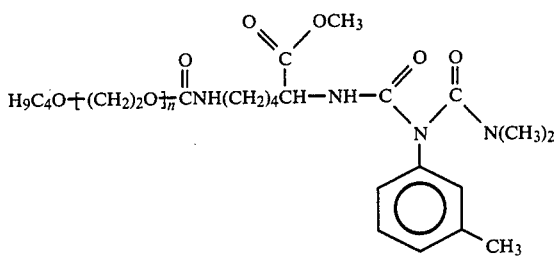

in which n=21.

EXAMPLE 47

22.1 g (0.01 mol) of the compound obtained according to Example 1(a) were reacted with 2.2 g (0.01 mol) of N-(2-benzothiazolyl)-N-methyl-N'-methyl-urea analogously to Example 9. Subsequent stirring time: 34 hours at 80° C.

23.7 g of a golden yellow solid were obtained. This active compound modified according to the invention was readily soluble in water and/or lower alcohols and had the ideal formula

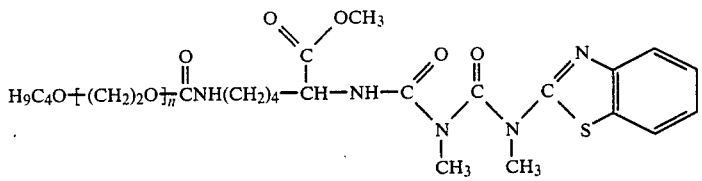

in which n=43.

EXAMPLE 48

12.1 g (0.01 mol) of the compound obtained according to Example 2(a) were reacted with 2.2 g (0.01 mol) of N-(2-benzothiazolyl)-N,N'-dimethylurea analogously to Example 10. Subsequent stirring time: 38 hours at 85° C.

14.0 g of a light yellow solid were obtained. This active compound modified according to the invention was readily soluble in water and lower alcohols and had the ideal formula

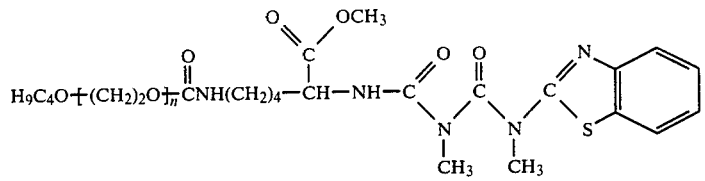

in which n=21.

EXAMPLE 49

9.9 g (0.01 mol) of the compound obtained according to Example 3(a) were reacted with 2.2 g (0.01 mol) of N-(2-benzothiazolyl)-N,N'-dimethylurea analogously to Example 11. Subsequent stirring time: 32 hours at 75° C.

11.7 g of a pale yellow, highly viscous product were obtained. This active compound modified according to the invention was readily soluble in water and lower alcohols and had the ideal formula

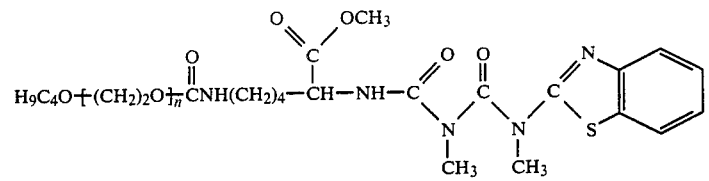

in which n=16.

EXAMPLE 50

22.1 g (0.01 mol) of the compound obtained according to Example 1(a) were reacted with 2.0 g (0.01 mol) of 3-methyl-4-amino-6-phenyl-1,2,4-triazin-5(4H)-one analogously to Example 9. Subsequent stirring time: 8 hours at 105° C.

23.7 g of a gray-yellow solid were obtained. This active compound modified according to the invention was readily soluble in water and/or lower alcohols and had the ideal formula

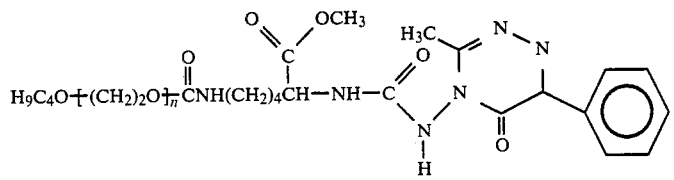

in which n=43.

EXAMPLE 51

9.9 g (0.01 mol) of the compound obtained according to Example 3(a) were reacted with 2.0 g (0.01 mol) of 3-methyl-4-amino-6-phenyl-1,2,4-triazin-5(4H)-one analogously to Example 11. Subsequent stirring time: 12 hours at 95° C.

11.6 g of a grey-golden coloured, highly viscous product were obtained. This active compound modified according to the invention was readily soluble in water and/or lower alcohols and had the ideal formula

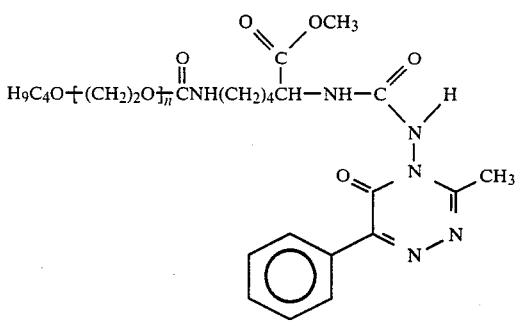

in which n=16.

EXAMPLE 52

22.1 g (0.01 mol) of the compound obtained according to Example 1(a) were reacted with 2.6 g (0.01 mol) of 1-amino-3-(1-methylpropyl)-5-bromo-6-methyl-1,3-diazine-(5H)-2,4-dione analogously to Example 9. Subsequent stirring time: 16 hours at 100° C.

24.4 g of a dark yellow solid were obtained. This active compound modified according to the invention was readily soluble in water and/or lower alcohols and had the ideal formula

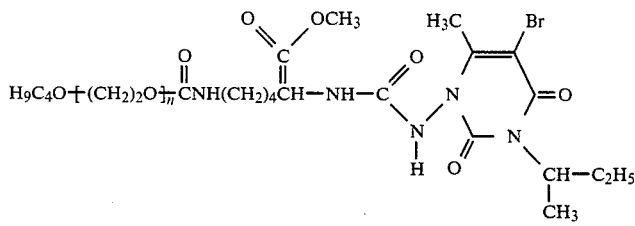

in which n=43.

EXAMPLE 53

9.9 g (0.01 mol) of the compound obtained according to Example 3(a) were reacted with 2.6 g (0.01 mol) of 1-amino-3-(1-methyl-propyl)-5-bromo-6-methyl-1,3-diazine-(5H)-2,4-dione analogously to Example 11. Subsequent stirring time: 14 hours at 110° C.

12.1 g of a dark yellow, highly viscous product were obtained. This active compound modified according to the invention was readily soluble in water and lower alcohols and had the ideal formula

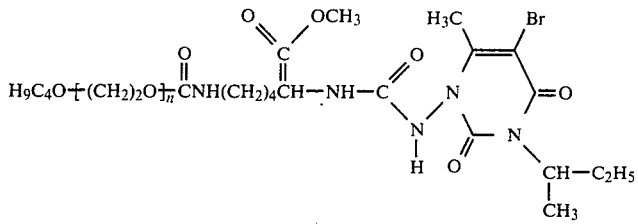

in which n=16.

EXAMPLE 54

22.1 g (0.01 mol) of the compound obtained according to Example 1(a) were reacted with 3.1 g (0.01 mol) of N-o,o'-difluorobenzoyl-N'-p-chlorophenylurea analogously to Example 9. Subsequent stirring time: 6 hours at 110° C.

24.6 g of a dark brown solid were obtained. This active compound modified according to the invention was readily soluble in water and/or lower alcohols and had the ideal formula in which n=43.

EXAMPLE 55

22.1 g (0.01 mol) of the compound obtained according to Example 1(a) were reacted with 3.7 g (0.01 mol) of 3-(3,4-dichlorophenyl)-6-(2,6-difluorophenyl)-1-oxa-3,5-diazine-(3H,5H)-2,4-dione analogously to Example 9. Subsequent stirring time: 8 hours at 100° C.

25.1 g of a greenish-yellow solid were obtained. This active compound modified according to the invention was readily soluble in water and/or lower alcohols and had the ideal formula

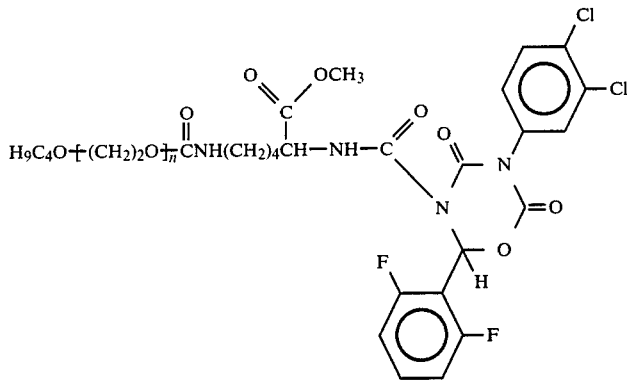

in which n=43.

EXAMPLE 56

12.1 g (0.01 mol) of the compound obtained according to Example 2(a) were reacted with 3.7 g (0.01 mol) of 3-(3,4-dichlorophenyl)-6-(2,6-difluorophenyl)-1-oxa-3,5-diazine-(3H,4H)-2,4-dione analogously to Example 10. Subsequent stirring time: 10 hours at 95° C.

15.2 g of a green-brown solid were obtained. This active compound modified according to the invention was readily soluble in water and/or lower alcohols and had the ideal formula

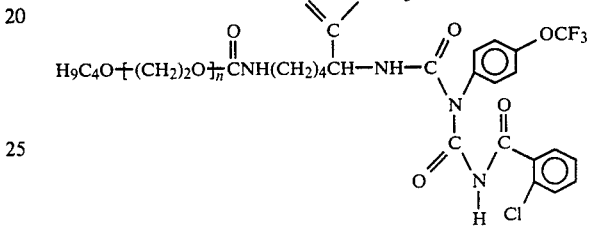

in which n=43.

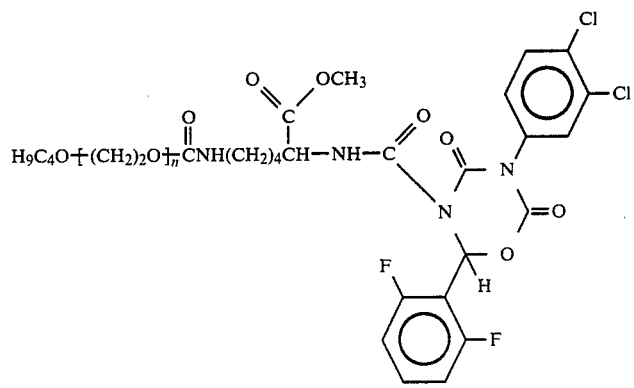

in which n=21.

EXAMPLE 57

22.1 g (0.01 mol) of the compound obtained according to Example 1(a) were reacted with 3.4 g of N-(2-chlorobenzoyl)-N'-(4-trifluoromethoxyphenyl)-urea analogously to Example 9. Subsequent stirring time: 10 hours at 105° C.

25.1 g of a golden yellow solid were obtained. This active compound modified according to the invention was readily soluble in water and/or lower alcohols and had the ideal formula

EXAMPLE 58

22.1 g (0.01 mol) of the compound obtained according to Example 1(a) were reacted with 2.1 g (0.01 mol) of 4-benzothienyl N-methylcarbamate analogously to Example 9. Subsequent stirring time: 8 hours at 90° C.

23.6 g of a yellow solid were obtained. This active compound modified according to the invention was readily soluble in water and lower alcohols and had the ideal formula

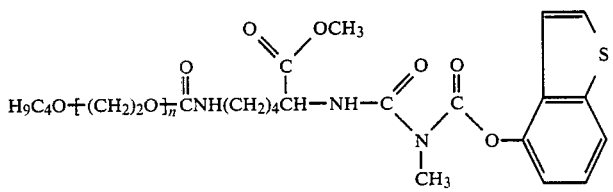

in which n=43.

EXAMPLE 59

12.1 g (0.01 mol) of the compound obtained according to Example 2(a) were reacted with 2.0 g (0.01 mol) of 1-naphthyl N-methylcarbamate analogously to Example 10. Subsequent stirring time: 9 hours at 90° C.

13.8 g of a golden yellow solid were obtained. This active compound modified according to the invention was readily soluble in water and lower alcohols and had the ideal formula

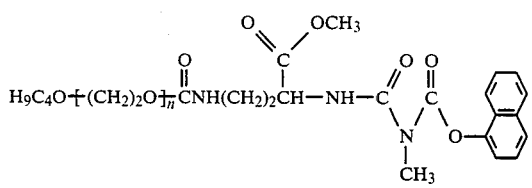

in which n=21.

EXAMPLE 60

9.9 g (0.01 mol) of the compound obtained according to Example 3(a) were reacted with 1.8 g (0.01 mol) of 3,4-dimethylphenyl N-methylcarbamate analogously to Example 11. Subsequent stirring time: 7 hours at 95° C.

10.2 g of a pale yellow, highly viscous product were obtained. This active compound modified according to the invention was readily soluble in water and lower alcohols and had the ideal formula

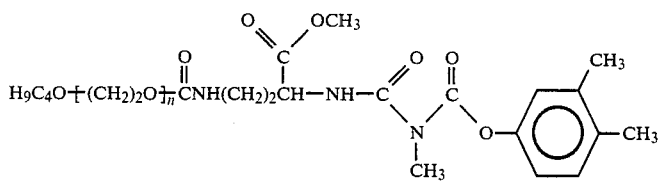

in which n=16.

EXAMPLE 61

12.2 g (0.01 mol) of the compound obtained according to Example 1(a) were reacted with 3.1 g (0.01 mol) of p-chlorophenyl N-(2,6-difluorobenzoyl)-carbamate analogously to Example 9. Subsequent stirring time: 16 hours at 110° C.

24.7 g of a yellowish brown solid were obtained. This active compound modified according to the invention was readily soluble in water and lower alcohols and had the ideal formula

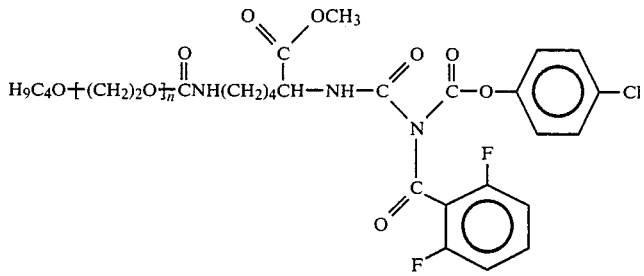

in which n=43.

EXAMPLE 62

9.9 g (0.01 mol) of the compound obtained according to Example 3(a) were reacted with 3.5 g (0.01 mol) of o,o'-dichlorophenyl N-(2,6-difluorobenzoyl)-carbamate analogously to Example 11. Subsequent stirring time: 20 hours at 95° C.

11.5 g of a dark brown, highly viscous product were obtained. This active compound modified according to the invention was readily soluble in water and lower alcohols and had the ideal formula

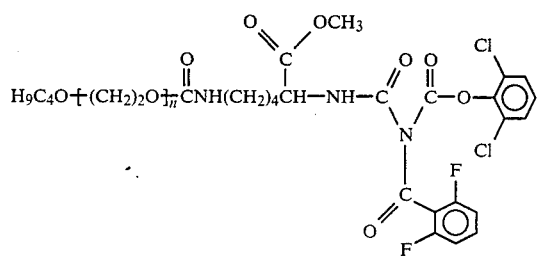

in which n=16.

EXAMPLE 63

22.1 g (0.01 mol) of the compound obtained according to Example 1(a) were reacted with 3.2 g (0.01 mol) of 7-nitrophenyl N-(2,6-difluorobenzoyl)-carbamate analogously to Example 9. Subsequent stirring time: 12 hours at 100° C.

25.1 g of a yellow solid were obtained. This active compound modified according to the invention was readily soluble in water and lower alcohols and had the ideal formula

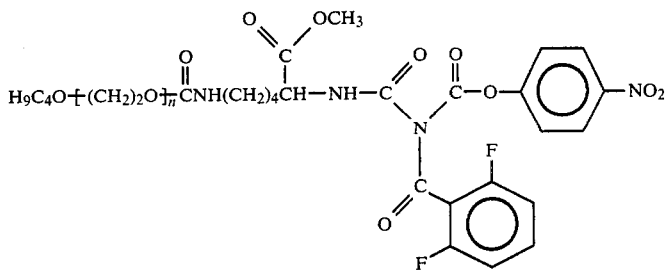

in which n=43.

EXAMPLE 64

9.9 g (0.01 mol) of the compound obtained according to Example 3(a) were reacted with 3.6 g (0.01 mol) of 2-chloro-4-nitrophenyl N-(2,6-difluorobenzoyl)-carbamate analogously to Example 11. Subsequent stirring time: 16 hours at 80° C.

12.7 g of a dark brown, viscous product were obtained. This active compound modified according to the invention was readily soluble in water and methanol as well as ethanol and had the ideal formula

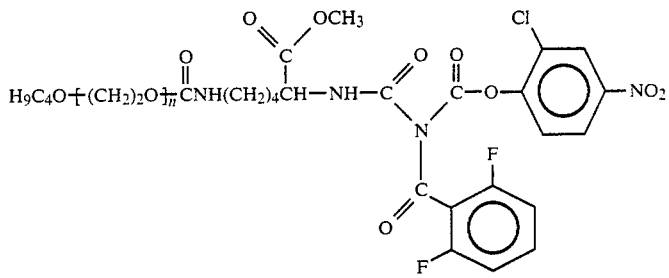

in which n=16.

EXAMPLE 65

22.1 g (0.01 mol) of the compound obtained according to Example 1(a) were reacted with 3.3 g (0.01 mol) of p-chlorophenyl N-(2,6-difluorobenzoyl)-thiocarbamate analogously to Example 9. Subsequent stirring time: 8 hours at 90° C.

25.3 g of a light brown solid were obtained. This active compound modified according to the invention was readily soluble in water and/or lower alcohols and had the ideal formula

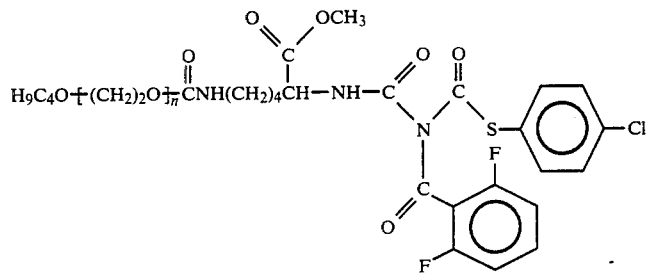

in which n=43.

EXAMPLE 66

22.1 g (0.01 mol) of the compound obtained according to Example 1(a) were reacted with 2.1 g (0.01 mol) of 2-isopropoxyphenyl N-methylcarbamate analogously to Example 9. Subsequent stirring time: 6 hours at 110° C.

24.0 g of a golden yellow solid were obtained. This active compound modified according to the invention was readily soluble in water and/or lower alcohols and had the ideal formula

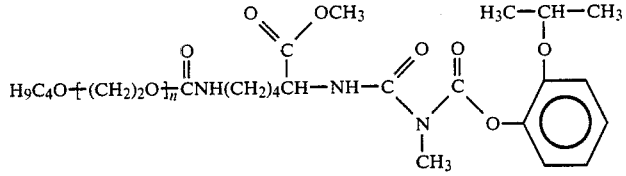

in which n=43.

EXAMPLE 67

12.1 g (0.01 mol) of the compound obtained according to Example 2(a) were reacted with 2.1 g (0.01 mol) of 2-isopropoxyphenyl N-methylcarbamate analogously to Example 10. Subsequent stirring time: 7 hours at 95° C.

13.7 g of a dark yellow solid of a wax-like consistency were obtained. This active compound modified according to the invention was readily soluble in water and lower alcohols and had the ideal formula

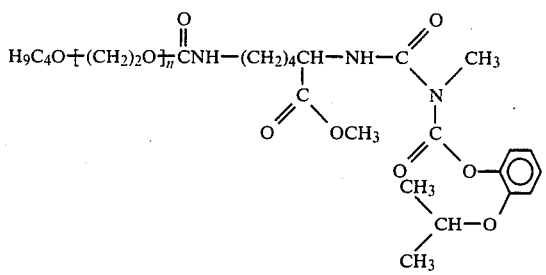

in which n=21.

EXAMPLE 68

9.9 g (0.01 mol) of the compound obtained according to Example 3(a) were reacted with 2.1 g (0.01 mol) of 2-isopropoxyphenyl N-methylcarbamate analogously to Example 11. Subsequent stirring time: 8 hours at 80° C.

11.6 g of a grey-yellow, viscous product were obtained. This active compound modified according to the invention was readily soluble in water and lower alcohols and had the ideal formula

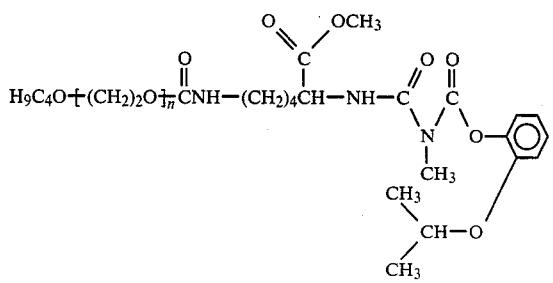

in which n=16.

EXAMPLE 69

22.1 g (0.01 mol) of the compound obtained according to Example 1(a) were reacted with 2.2 g (0.01 mol) of 2,3-dihydro-2,2-dimethyl-7-benzofuranyl N-methylcarbamate analogously to Example 3. Subsequent stirring time: 6 hours at 110° C.

23.7 g of a pale yellow solid were obtained. This active compound modified according to the invention was readily soluble in water and/or lower alcohols and had the ideal formula

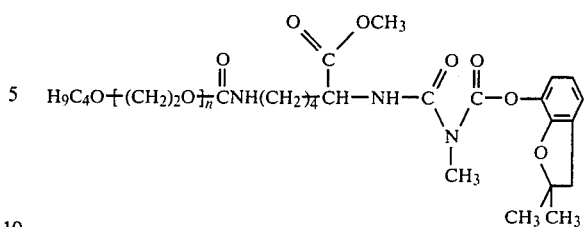

in which n=43.

EXAMPLE 70

12.1 g (0.01 mol) of the compound obtained according to Example 2(a) were reacted with 2.2 g (0.01 mol) of 2,3-dihydro-2,2-dimethyl-7-benzofuranyl N-methylcarbamate analogously to Example 10. Subsequent stirring time: 8 hours at 90° C.

13.5 g of a yellow solid were obtained. This active compound modified according to the invention was readily soluble in water and/or lower alcohols and had the ideal formula

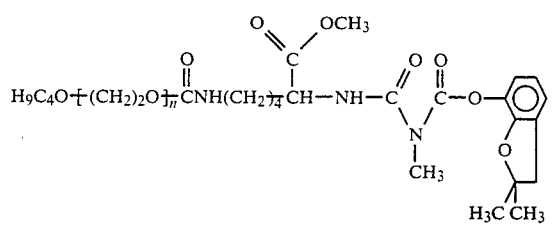

in which n=21.

EXAMPLE 71

12.1 g (0.01 mol) of the compound obtained according to Example 2(a) were reacted with 2.25 g (0.01 mol) of 3,5-dimethyl-4-methylmercapto-phenyl N-methylcarbamate analogously to Example 10. Subsequent stirring time: 11 hours at 105° C.

13.9 g of a brownish solid were obtained. This active compound modified according to the invention was readily soluble in water and/or lower alcohols and had the ideal formula

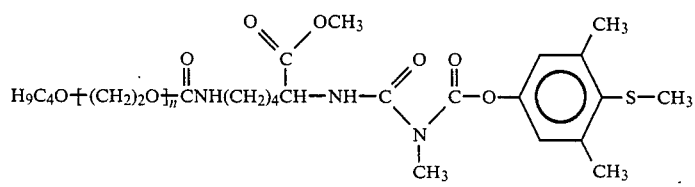

in which n=21.

EXAMPLE 72

9.9 g (0.01 mol) of the compound obtained according to Example 3(a) were reacted with 2.25 g (0.01 mol) of 3,5-dimethyl-4-methylmercapto-phenyl N-methylcarbamate analogously to Example 11. Subsequent stirring time: 16 hours at 80° C.

11.7 g of a dark yellow, viscous product were obtained. This active compound modified according to the invention was readily soluble in water and/or lower alcohols and had the ideal formula

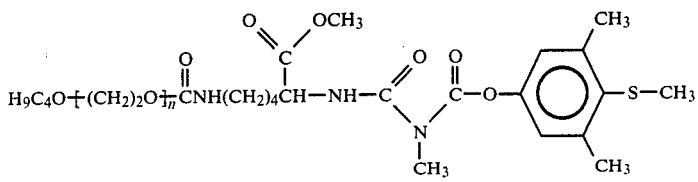

in which n=16.

EXAMPLE 73

22.1 g (0.01 mol) of the compound obtained according to Example 1(a) were reacted with 2.1 g (0.01 mol) of 3-amino-2,5-dichlorobenzoic acid analogously to Example 9. Subsequent stirring time: 1 hour at 80° C.

23.8 g of a colorless solid were obtained. This active compound modified according to the invention was readily soluble in water and had the ideal formula

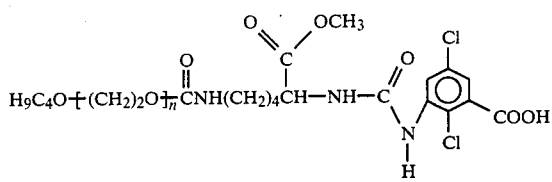

in which n=43.

EXAMPLE 74

22.1 g (0.01 mol) of the compound obtained according to Example 1(a) were reacted with 2.9 g (0.01 mol) of 3-(d-tetralyl)-4-hydroxycoumarin analogously to Example 10. Subsequent stirring time: 4 hours at 80° C.

24.6 g of a dark yellow solid were obtained. This active compound modified according to the invention was readily soluble in water and lower alcohols and had the ideal formula

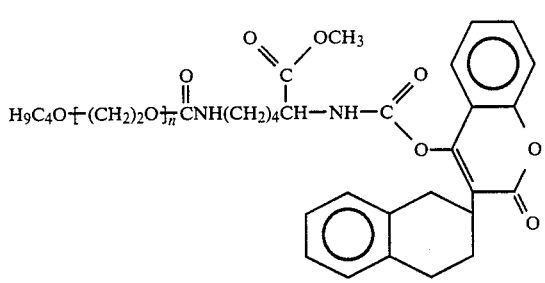

in which n=43.

EXAMPLE 75

9.9 g (0.01 mol) of the compound obtained according to Example 3(a) were reacted with 2.9 g (0.01 mol) of 3-(d-tetralyl)-4-hydroxycoumarin analogously to Example 11. Subsequent stirring time: 2 hours at 110° C.

13.4 g of a dark yellow-bronw, viscous product were obtained. This active compound modified according to the invention was readily soluble in water and lower alcohols and had the ideal formula

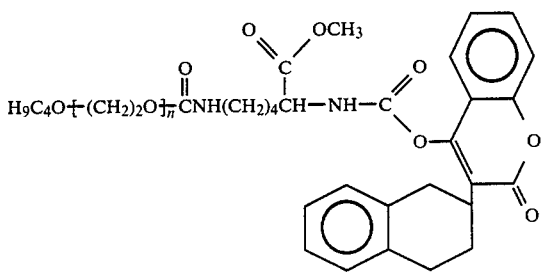

in which n=16.

EXAMPLE 76

12.1 g (0.01 mol) of the compound obtained according to Example 2(a) were reacted with 3.1 g (0.01 mol) of 3-(1'-phenyl-2'-acetylethyl)-4-hydroxycoumarin analogously to Example 10. Subsequent stirring time: 3 hours at 105° C.

14.7 g of a brown-pink solid of a wax-like consistency were obtained. This active compound modified according to the invention was readily soluble in water and lower alcohols and had the ideal formula

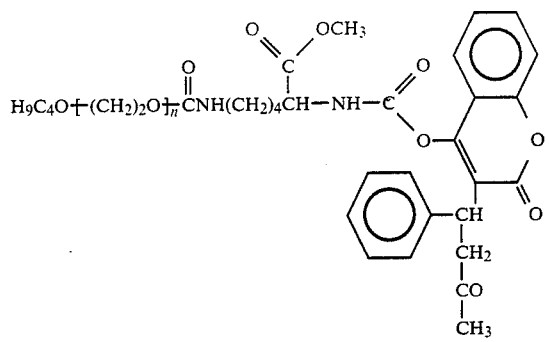

in which n=21.

EXAMPLE 77

22.1 g (0.01 mol) of the compound obtained according to Example 1(a) were reacted with 1.2 g (0.01 mol) of 4-aminoperhydro-1,2-oxazin-3-one analogously to Example 9. Subsequent stirring time: 30 minutes at 90° C.

22.9 g of a yellow solid were obtained. This active compound modified according to the invention was readily soluble in water and/or lower alcohols and had the ideal formula

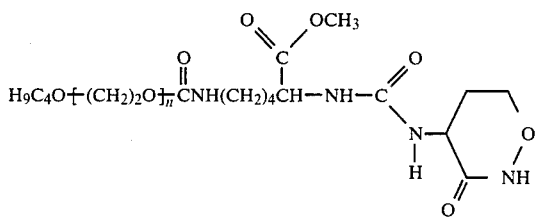

in which n=43.

EXAMPLE 78

12.1 g (0.01 mol) of the compound obtained according to Example 2(a) were reacted with 1.2 g (0.01 mol) of allylthiourea analogously to Example 10. Subsequent stirring time: 36 hours at 70° C.

22.7 g of a golden yellow solid were obtained. This active compound modified according to the invention was readily soluble in water and lower alcohols and had the ideal formula

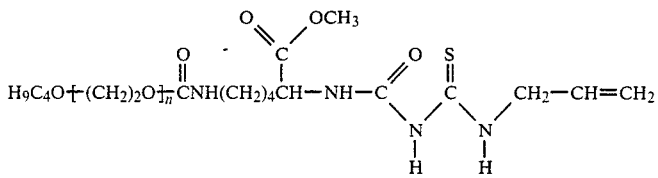

in which n=21.

EXAMPLE 79

9.9 g (0.01 mol) of the compound obtained according to Example 3(a) were reacted with 1.2 g (0.01 mol) of nicotinic acid amide analogously to Example 11. Subsequent stirring time: 20 hours at 105° C.

10.4 g of a dark yellow-red, viscous product were obtained. This new active compound modified according to the invention was readily soluble in water and methanol as well as ethanol and had the ideal formula

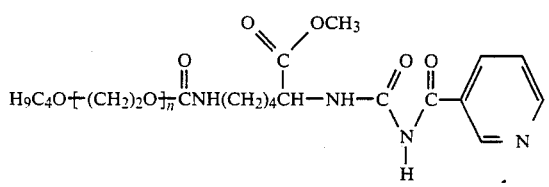

in which n=16.

EXAMPLE 80

22.1 g (0.01 mol) of the compound obtained according to Example 1(a) were reacted with 1.3 g (0.01 mol) of isonicotinic acid hydrazide analogously to Example 9. Subsequent stirring time: 2 hours at 95° C.

22.8 g of a light yellowish-white solid were obtained. This active compound modified according to the invention was readily soluble in water and/or lower alcohols and had the ideal formula

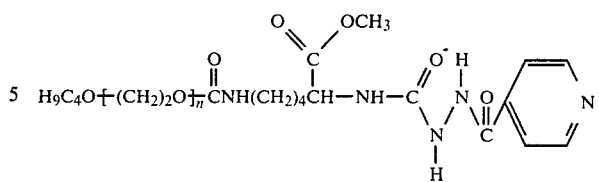

in which n=43.

EXAMPLE 81

12.1 g (0.01 mol) of the compound obtained according to Example 2(a) were reacted with 1.3 g (0.01 mol) of isonicotinic acid hydrazide analogously to Example 10. Subsequent stirring time: 2 hours at 95° C.

12.9 g of a yellow-white solid were obtained. This active compound modified according to the invention was readily soluble in water and/or lower alcohols and had the ideal formula

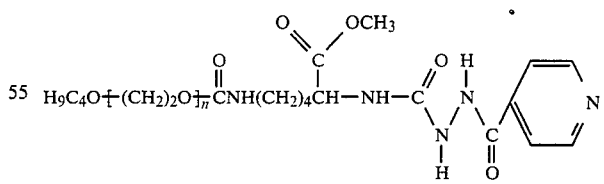

in which n=21.

EXAMPLE 82

9.9 g (0.01 mol) of the compound obtained according to Example 3(a) were reacted with 1.3 g (0.01 mol) of isonicotinic acid hydrazide analogously to Example 11. Subsequent stirring time: 2 hours at 95° C.

10.9 g of a golden yellow, viscous product were obtained. This active compound modified according to the invention was readily soluble in water and methanol as well as ethanol and had the ideal formula in which n=16.

EXAMPLE 83

22.1 g (0.01 mol) of the compound obtained according to Example 1(a) were reacted with 1.8 g (0.01 mol) of 1,3-dimethylpurine-2,6-(1H,3H)-dione analogously to Example 9. Subsequent stirring time: 1 hour at 80° C.

23.6 g of a dark yellow solid were obtained. This active compound modified according to the invention was readily soluble in water and/or lower alcohols and had the ideal formula

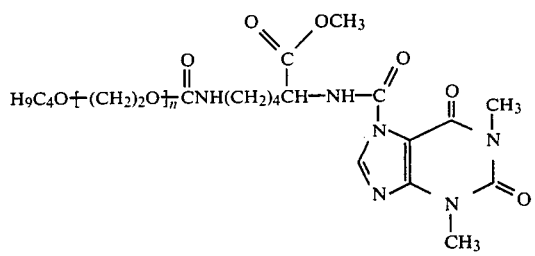

in which n=43.

EXAMPLE 84

12.1 g (0.01 mol) of the compound obtained according to Example 2(a) were reacted with 2.4 g (0.01 mol) of 4-amino-1-ribofuranosyl-1,3,5-triazin-2(1H)-one analogously to Example 10. Subsequent stirring time: 2 hours at 55° C.

14.2 g of an almost colorless solid were obtained. This active compound modified according to the invention was outstandingly soluble in water and had the ideal formula

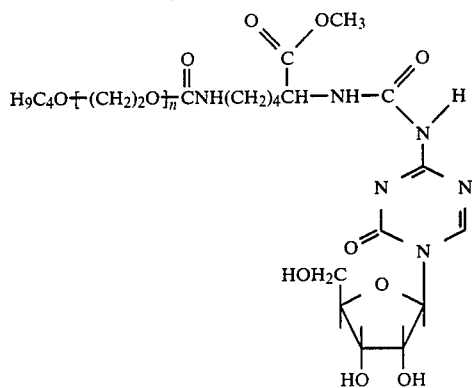

in which n=21.

EXAMPLE 85

22.1 g (0.01 mol) of the compound obtained according to Example 1(a) were reacted with 2.6 g (0.01 mol) of 2-sulphanilamidothiazole analogously to Example 9. Subsequent stirring time: 30 minutes at 70° C.

24.3 g of a yellow solid were obtained. This active compound modified according to the invention was readily soluble in water and/or lower alcohols and had the ideal formula

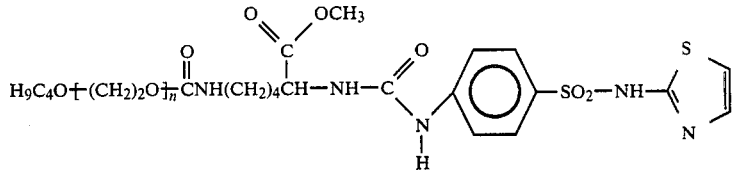

in which n=43.

EXAMPLE 86

22.1 g (0.01 mol) of the compound obtained according to Example 1(a) were reacted with 2.6 g (0.01 mol) of 3(5)-ribofuranosyl-4-hydroxypyrazole-5(3)-carboxamide analogously to Example 9. Subsequent stirring time: 9 hours at 50° C.

24.2 g of a dark yellow-red solid were obtained. This active compound modified according to the invention was readily soluble in water and/or lower alcohols and had the ideal formula

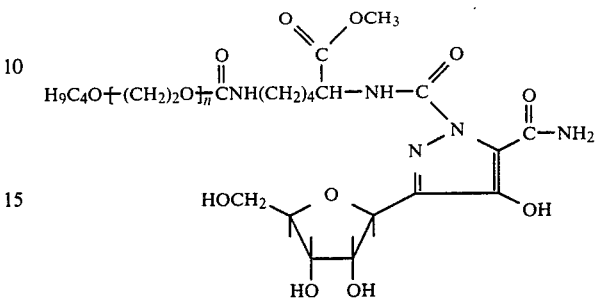

in which n=43.

EXAMPLE 87

44.2 g (0.02 mol) of the compound obtained according to Example 1(a) were reacted with 2.2 g (0.01 mol) of 2-methyl-2-n-propyl-trimethylene dicarbamate analogously to Example 9. Subsequent stirring time: 17 hours at 110° C.

45.7 g of a brown-yellow solid were obtained. This active compound modified according to the invention was outstandingly soluble in water and/or lower alcohols and had the ideal formula

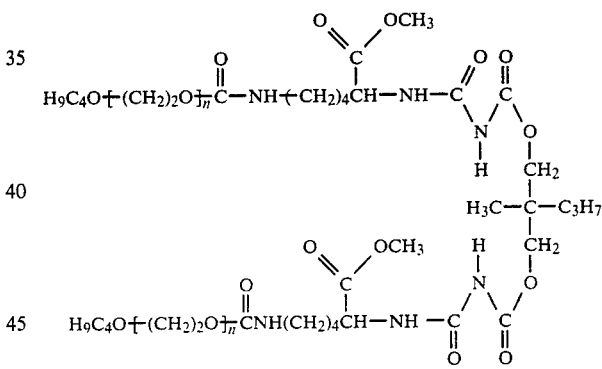

in which n=43.

EXAMPLE 88

19.8 g (0.02 mol) of the compound obtained according to Example 3(a) were reacted with 2.2 g (0.01 mol) of 2-n-propyl-trimethylene dicarbamate analogously to Example 11. Subsequent stirring time: 17 hours at 110° C.

21.6 g of a brown-red, viscous product were obtained. This active compound modified according to the invention was readily soluble in water and/or lower alcohols and had the ideal formula

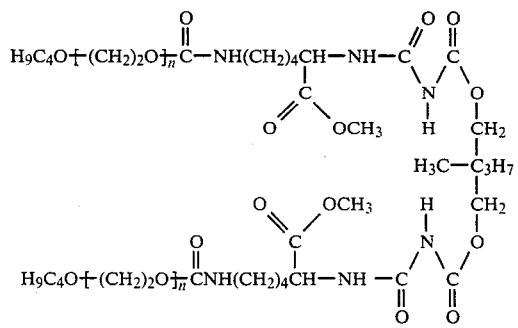

in which n=16.

EXAMPLE 89

22.1 g (0.01 mol) of the compound obtained according to Example 1(a) were reacted with 2.2 g (0.01 mol) of D(−)-threo-1-(p-nitrophenyl)-2-dichloroacetamido-1,3-propanediol analogously to Example 9. Subsequent stirring time: 6 hours at 95° C.

24.0 g of a golden yellow solid were obtained. This active compound modified according to the invention was readily soluble in water and/or lower alcohols and had the ideal formula

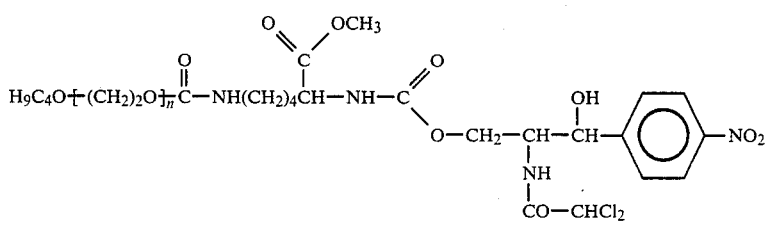

in which n=43.

EXAMPLE 90

9.9 g (0.01 mol) of the compound obtained according to Example 3(a) were reacted with 2.2 g (0.01 mol) of D(−)-threo-1-(p-nitrophenyl)-2-dichloroacetamido-1,3-propanediol analogously to Example 11. Subsequent stirring time: 5 hours at 85° C.

11.7 g of a pink-yellow, viscous product were obtained. This active compound modified according to the invention was readily soluble in water and/or lower alcohols and had the ideal formula

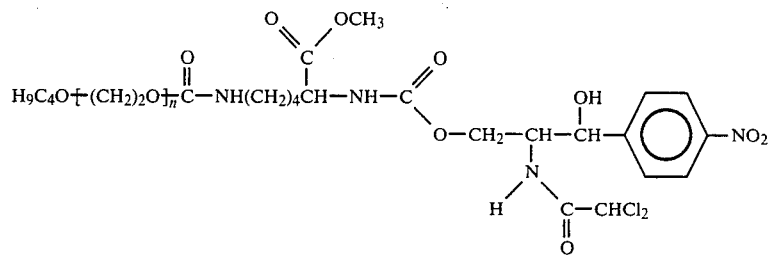

in which n=16.

EXAMPLE 91

12.1 g (0.01 mol) of the compound obtained according to Example 2(a) were reacted with 2.2 g (0.01 mol) of 5,6-dihydro-2-(2,6-xylidino)-4H-1,3-thiazine analogously to Example 10. Subsequent stirring time: 1 hour at 75° C.

14.0 g of a dark yellow solid were obtained. This active compound modified according to the invention was readily soluble in water and lower alcohols and had the ideal formula

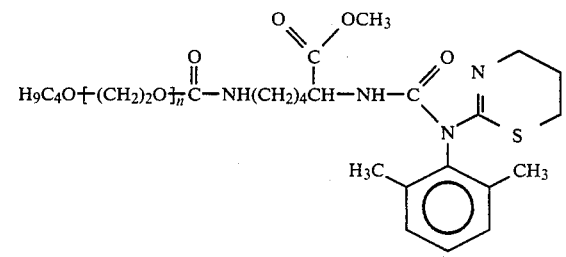

in which n=21.

EXAMPLE 92

22.1 g (0.01 mol) of the compound obtained according to Example 1(a) were reacted with 3.9 g (0.01 mol) of N-(4-chloro-3-sulphamoylbenzenesulphonyl)-N-methyl-2-aminomethyl-2-methyltetrahydrofuran analogously to Example 9. Subsequent stirring time: 18 hours at 95° C.

25 g of a brown-yellow solid were obtained. This active compound modified according to the invention was readily soluble in water and lower alcohols and had the ideal formula

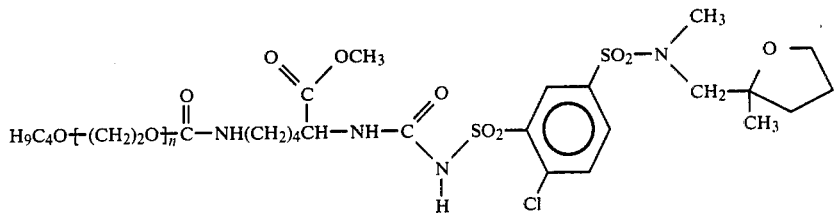

in which n=43.

EXAMPLE 93

12.1 g (0.01 mol) of the compound obtained according to Example 2(a) were reacted with 2.4 g (0.01 mol) of 2-diethylaminoethyl p-aminobenzoate analogously to Example 10. Subsequent stirring time: 30 minutes at 70° C.

14.2 g of a colorless solid of wax-like consistency were obtained. This active compound modified according to the invention was readily soluble in water and/or lower alcohols and had the ideal formula

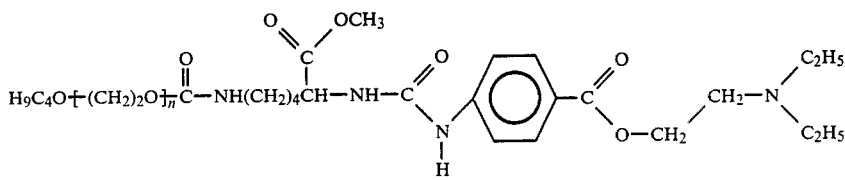

in which n=21.

EXAMPLE 94

22.1 g (0.01 mol) of the compound obtained according to Example 1(a) were reacted with 3.6 g (0.01 mol) of D(+)-6-(5-amino-5-carboxyvaleramido)-3,3-dimethyl-7-oxo-4-thia-1-azabicyclo-[3,2,0]-heptane-2-carboxylic acid analogously to Example 9. Subsequent stirring time: 2 hours at 55° C.

25.3 g of a pale yellow solid were obtained. This active compound modified according to the invention was readily soluble in water and/or lower alcohols and had the ideal formula in which n=43.

EXAMPLE 95

9.9 g (0.01 mol) of the compound obtained according to Example 3(a) were reacted with 3.2 g (0.01 mol) of 1-phenyl-5-sulphanilamidopyrazole analogously to Example 11. Subsequent stirring time: 45 minutes at 85° C.

12.8 g of a pink-yellow, viscous product were obtained. This active compound modified according to the invention was readily soluble in water and/or methanol as well as ethanol and had the ideal formula

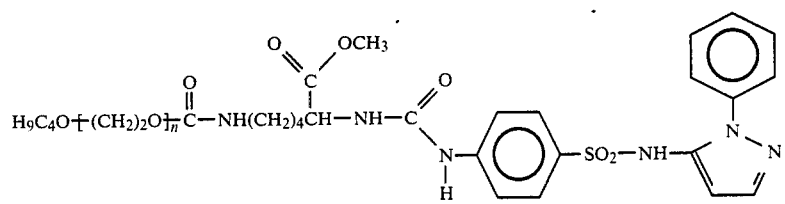

in which n=16.

EXAMPLE 96

22.1 g (0.01 mol) of the compound obtained according to Example 1(a) were reacted with 3.8 g (0.01 mol) of D-7-amino-2-phenylacetamido)-3-methyl-8-oxo-5-thia-1-azabicyclo-[4,2,0]oct-2-ene-2-carboxylic acid analogously to Example 9. Subsequent stirring time: 3 hours at 55° C.

25.6 g of a pale yellow solid were obtained. This active compound modified according to the invention was readily soluble in water and/or lower alcohols and had the idela formula

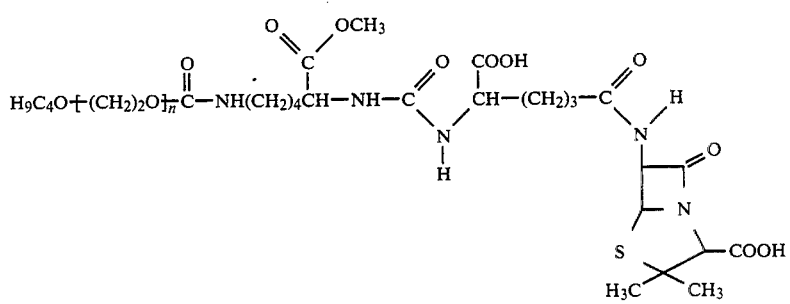

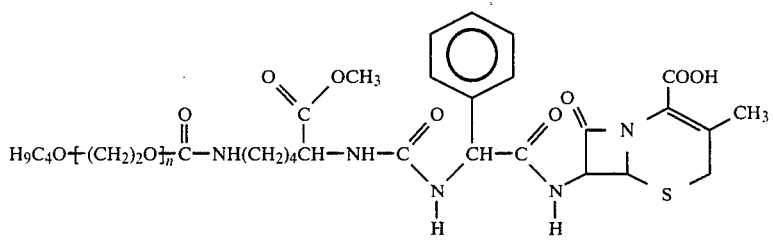

in which n=43.

EXAMPLE 97

12.1 g (0.01 mol) of the compound obtained according to Example 2(a) were reacted with 3.5 g (0.01 mol) of D(−)-6-(α-aminophenylacetamido)-3,3-dimethyl-7-oxo-4-thia-1-azabicyclo-[3,2,0]-heptane-2-carboxylic acid analogously to Example 10. Subsequent stirring time: 45 minutes at 60° C.

15.3 g of a pale yellow solid were obtained. This active compound modified according to the invention was readily soluble in water and/or alcohols and had the ideal formula gously to Example 11. Subsequent stirring time: 1 hour at 70° C. 13.1 g of a yellow-red viscous product were obtained. This active compound modified according to the invention was readily soluble in water and/or ethanol and had the ideal formula

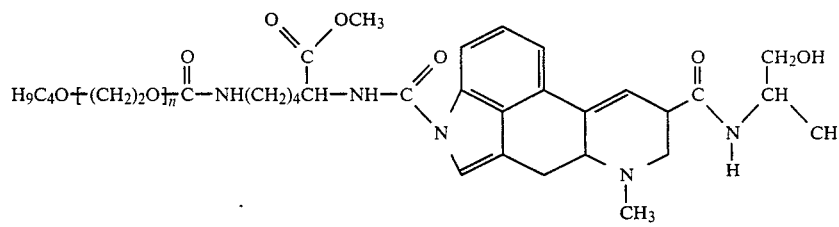

in which n=16.

EXAMPLE 99

22.1 g (0.01 mol) of the compound obtained according to Example 1(a) were reacted with 5.3 g (0.01 mol) of 9-acetyl-7,8,9,10-tetrahydro-6,7,9,11-tetrahydroxy-4-methoxy-5,12-naphthacenequinone-7-(3-amino-5-methyl-2,3-dideoxy-α-lyxopyranoside) analogously to Example 9. Subsequent stirring time: 2 hours at 55° C.

27.0 g of a pale yellow solid were obtained. This active compound modified according to the invention was readily soluble in water and/or lower alcohols and had the ideal formula

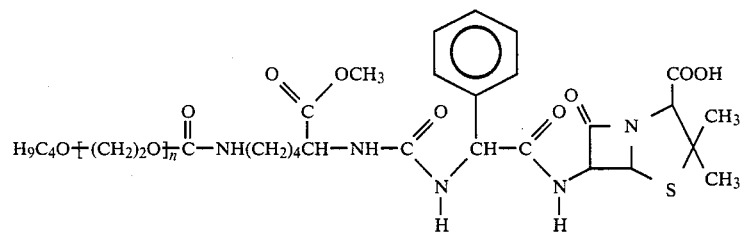

in which n=21.

EXAMPLE 98

9.9 g (0.01 mol) of the compound obtained according to Example 3(a) were reacted with 3.3 g (0.01 mol) of D(+)-lysergic acid β-hydroxyisopropylamide analo-

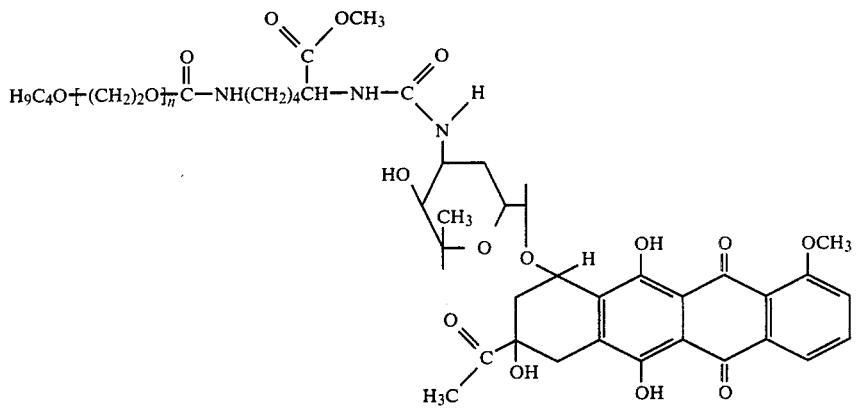

in which n=43.

EXAMPLE 100

22.1 g (0.01 mol) of the compound obtained according to Example 1(a) were reacted with 1.7 g (0.01 mol) of 6-aminopurine-8-thiol analogously to Example 9. Subsequent stirring time: 15 minutes at 45° C.

23.4 g of a red-yellow solid were obtained. This active compound modified according to the invention was readily soluble in water and/or lower alcohols and had the ideal formula

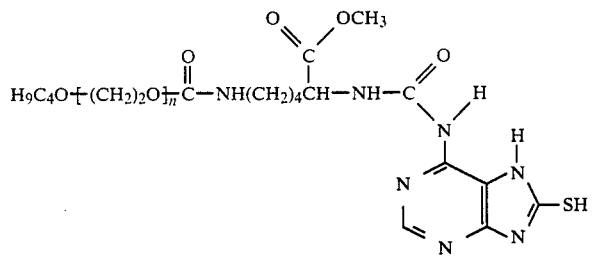

in which n=43.

EXAMPLE 101

22.1 g (0.01 mol) of the compound obtained according to Example 1(a) were reacted with 2.2 g (0.01 mol) of 6-amino-3,3-dimethyl-7-oxo-4-thia -1-azabicyclo- [3,2,0]-heptane-carboxylic acid analogously to Example 9. Subsequent stirring time: 30 minutes at 60° C.

24.0 g of a whitish-yellow solid were obtained. This active compound modified according to the invention was readily soluble in water and/or lower alcohols as well as ethyl acetate and acetone and had the idea formula

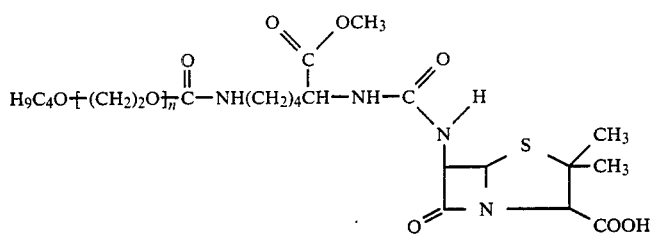

in which n=43.

EXAMPLE 102

9.9 g (0.01 mol) of the compound obtained according to Example 3(a) were reacted with 2.4 g (0.01 mol) of 2-ethyl-2-bromobutyryl-urea analogously to Example 11. Subsequent stirring time: 36 hours at 95° C.

12 g of a red-brown, viscous product were obtained. This active compound modified according to the invention was readily soluble in water and methanol as well as ethanol and had the ideal formula

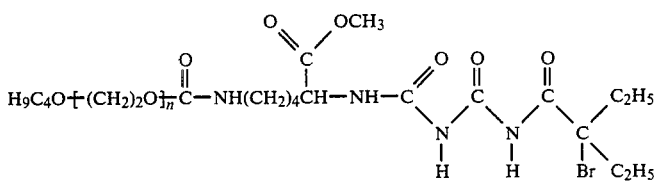

in which n=16.

EXAMPLE 103

12.1 g (0.01 mol) of the compound obtained according to Example 2(a) were reacted with 2.3 g (0.01 mol) of 4-amino-benzenesulphothiocarbamide analogously to Example 10. Subsequent stirring time: 20 minutes at 85° C.

14.1 g of a red-golden, wax-like solid were obtained. This active compound modified according to the invention was readily soluble in water and/or lower alcohols and had the ideal formula

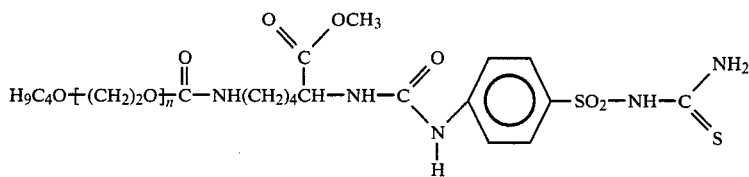

in which n=21.

EXAMPLE 104

22.1 g (0.01 mol) of the compound obtained according to Example 1(a) were reacted with 3.5 g (0.01 mol) of 2,6-dimethyl-3,5-dimethoxycarbonyl-4-o-nitrophenyl-1,4-dihydropyridine analogously to Example 9. Subsequent stirring time: 1 hour at 70° C.

25.3 g of a dark yellow solid were obtained. This active compound modified according to the invention was readily soluble in water and/or lower alcohols and had the ideal formula

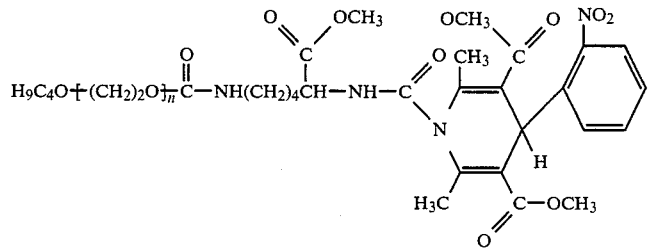

in which n=43.

EXAMPLE 105

12.1 g (0.01 mol) of the compound obtained according to Example 2(a) were reacted with 3.5 g (0.01 mol) of 2,6-dimethyl-3,5-dimethoxycarbonyl-4-o-nitrophenyl-1,4-dihydropyridine analogously to Example 10. Subsequent stirring time: 1 hour at 70° C.

15.1 g of a dark yellow, wax-like solid were obtained. This active compound modified according to the invention was readily soluble in water and/or lower alcohols and had the ideal formula

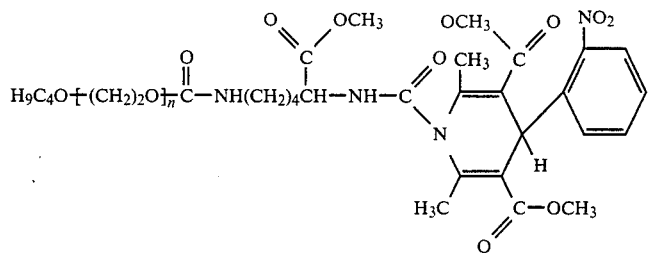

in which n=21.

EXAMPLE 106

9.9 g (0.01 mol) of the compound obtained according to Example 3(a) were reacted with 3.5 g (0.01 mol) of 2,6-dimethyl-3,5-dimethoxycarbonyl-4-o-nitrophenyl-1,4-dihydropyridine analogously to Example 11. Subsequent stirring time: 1 hour at 70° C.

13.0 g of a reddish-yellow, viscous product were obtained. This active compound modified according to the invention was readily soluble in water and/or lower alcohols and had the ideal formula

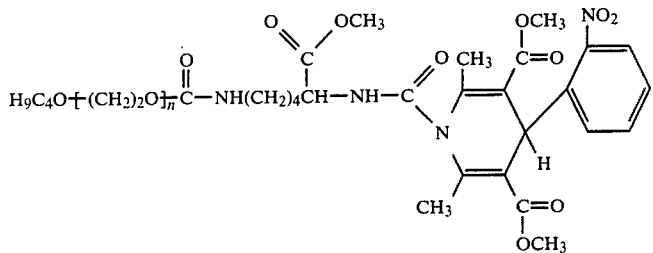

in which n=16.

EXAMPLE 107

22.1 g (0.01 mol) of the compound obtained according to Example 1(a) were reacted with 2.8 g (0.01 mol) of 2-sulphanilamido-5-methoxypyrimidine analogously to Example 9. Subsequent stirring time: 30 minutes at 75° C.

24.7 g of a pale yellow solid were obtained. This active compound modified according to the invention was readily soluble in water and/or lower alcohols and had the ideal formula

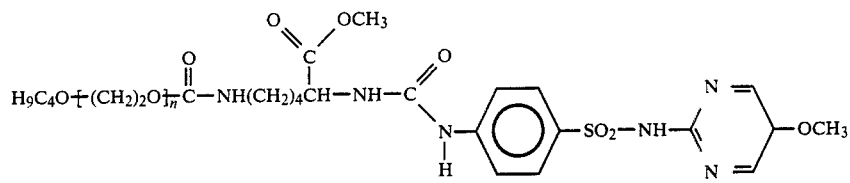

in which n=43.

EXAMPLE 108

108.4 g (0.05 mol) of the compound obtained according to Example 1(b) were reacted with 10.7 g (0.05 mol) of 4-amino-6-tert.-butyl-3-(methylthio)-1,2,4-triazin-5(4H)-one analogously to Example 25. Subsequent stirring time: 3 hours at 105° C.

117.4 g of a yellow solid were obtained. This active compound modified according to the invention was very readily soluble in water and/or lower alcohols and had the ideal formula

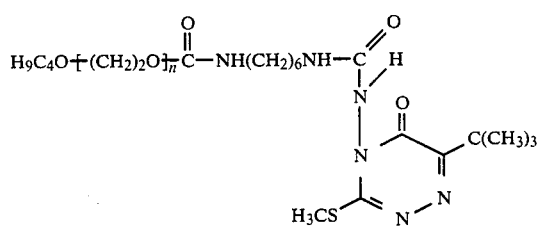

in which n=43.

EXAMPLE 109

58.4 g (0.05 mol) of the compound obtained according to Example 2(b) were reacted with 10.7 g (0.05 mol) of 4-amino-6tert.-butyl-3-(methylthio)-1,2,4-triazin-5(4H)-one analogously to Example 26. Subsequent stirring time: 2 hours at 100° C.

68.3 g of a dark yellow, wax-like solid were obtained. This active compound modified according to the invention was readily soluble in water and/or lower alcohols and had the ideal formula

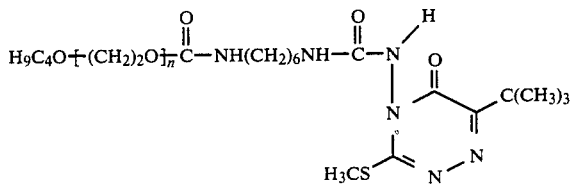

in which n=21.

EXAMPLE 110

47.6 g (0.05 mol) of the compound obtained according to Example 3(b) were reacted with 10.7 g (0.05 mol) of 4-amino-6-tert.-butyl-3-(methylthio)-1,2,4-triazin-5(4H)-one analogously to Example 27. Subsequent stirring time: 115 minutes at 115° C.

58.1 g of a dark yellow-red, viscous product were obtained. This active compound modified according to the invention was very readily soluble in water and/or lower alcohols and had the ideal formula

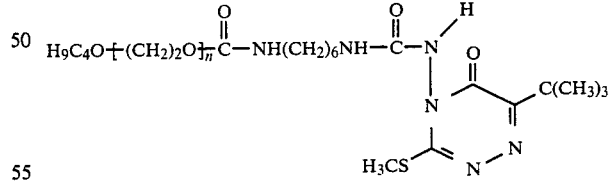

in which n=16.

EXAMPLE 111

21.7 g (0.01 mol) of the compound obtained according to Example 1(b) were reacted with 2.2 g (0.01 mol) of N-(2-benzothiazolyl)-N,N'-dimethyl-urea analogously to Example 47. Subsequent stirring time: 27 hours at 95° C.

23.5 g of a dark grey-yellow, wax-like solid were obtained. This active compound modified according to the invention was readily soluble in water and/or lower alcohols and had the ideal formula

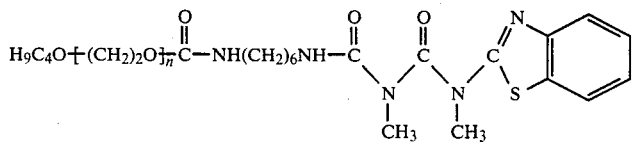

in which n=43.

EXAMPLE 112

11.7 g (0.01 mol) of the compound obtained according to Example 2(b) were reacted with 2.2 g (0.61 mol) of N-(2-benzothiazolyl)-N,N'-dimethylurea analogously to Example 48. Subsequent stirring time: 31 hours at 85° C.

13.4 g of a dark yellow-brown, wax-like solid were obtained. This active compound modified according to the invention was readily soluble in water and/or lower alcohols and had the ideal formula

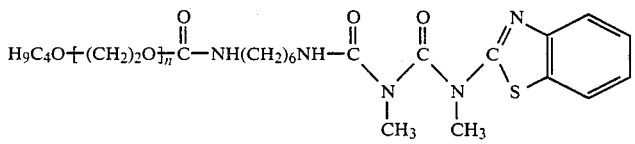

in which n=21.

EXAMPLE 113

9.5 g (0.01 mol) of the compound obtained according to Example 3(b) were reacted with 2.2 g (0.01 mol) of N-(2-benzothiazolyl)-N,N'-dimethylurea analogously to Example 49. Subsequent stirring time: 32 hours at 75° C.

11.4 g of a brown-yellow, viscous product were obtained. This active compound modified according to the invention was readily soluble in water and methanol as well as ethanol and had the ideal formula in which n=16.

EXAMPLE 114

11.7 g (0.01 mol) of the compound obtained according to Example 2(b) were reacted with 2.6 g (0.01 mol) of 1-amino-3-(1-methyl-propyl)-5-bromo-6-methyl-1,3-diazine-(5H)-2,4-dione analogously to Example 52. Subsequent stirring time: 17 hours at 100° C.

13.9 g of a dark yellow-grey solid were obtained. This active compound modified according to the invention was readily soluble in water and/or lower alcohols and had the ideal formula

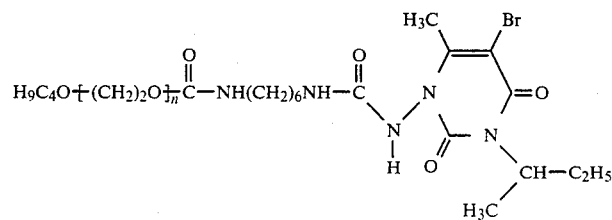

in which n=21.

EXAMPLE 115

11.7 g (0.01 mol) of the compound obtained according to Example 2(b) were reacted with 3.1 g (0.01 mol) of N-(o,o'-difluorobenzcyl)-N'-(p-chlorophenyl)-urea analogously to Example 54. Subsequent stirring time: 18 hours at 110° C.

14.5 g of a dark brown, wax-like solid were obtained. This active compound modified according to the invention was readily soluble in water and/or lower alcohols and had the ideal formula

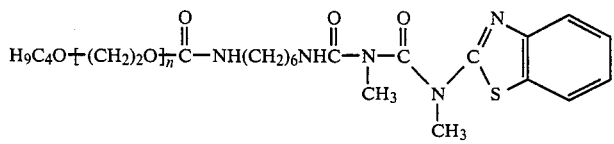

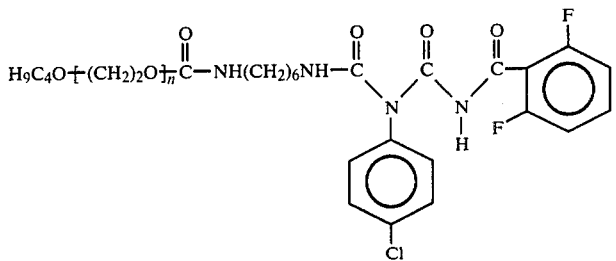

in which n=21.

EXAMPLE 116

9.5 g (0.01 mol) of the compound obtained according to Example 3(b) were reacted with 3.7 g (0.01 mol) of 3-(3,4-dichlorophenyl)-6-(2,6-difluorophenyl)-1-oxa-3,5-diazine-(3H,5H)-2,4-dione analogously to Example 55. Subsequent stirring time: 12 hours at 95° C.

12.7 g of a grey-green-brown, viscous product were obtained. This active compound modified according to the invention was readily soluble in water and methanol as well as ethanol and ethyl acetate and had the ideal formula

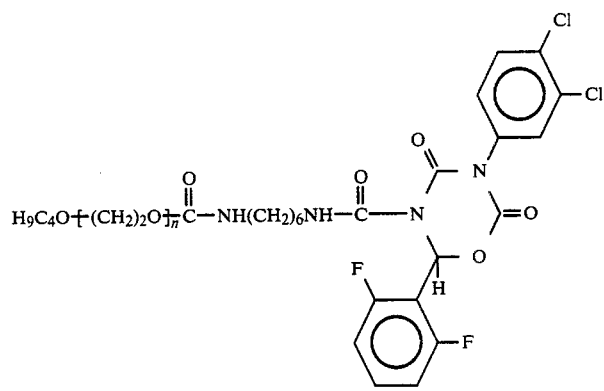

in which n=16.

EXAMPLE 117

21.7 g (0.01 mol) of the compound obtained according to Example 1(b) were reacted with 2.1 g (0.01 mol) of 2-isopropoxyphenyl N-methylcarbamate analogously to Example 66. Subsequent stirring time: 7 hours at 105° C.

23.6 g of a golden yellow solid were obtained. This active compound modified according to the invention was readily soluble in water and/or lower alcohols and had the ideal formula

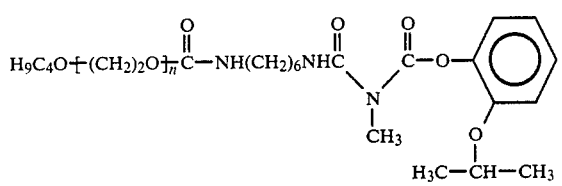

in which n=43.

EXAMPLE 118

11.7 g (0.01 mol) of the compound obtained according to Example 2(b) were reacted with 2.1 g (0.01 mol) of 2-isopropoxyphenyl N-methylcarbamate analogously to Example 67. Subsequent stirring time: 6 hours at 100° C.

13.3 g of a dark yellow-grey solid of wax-like consistency were obtained. This active compound modified according to the invention was readily soluble in water and/or lower alcohols and had the ideal formula

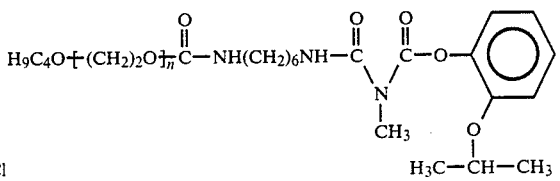

in which n=21.

EXAMPLE 119

9.5 g (0.01 mol) of the compound obtained according to Example 3(b) were reacted with 2.1 g (0.01 mol) of 2-isopropoxyphenol N-methylcarbamate analogously to Example 68. Subsequent stirring time: 9 hours at 75° C.

11.2 g of a grey-yellow, viscous product were obtained. This active compound modified according to the invention was readily soluble in water and lower alcohols and had the ideal formula

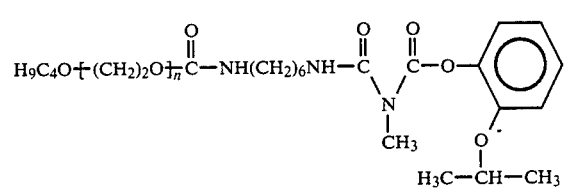

in which n=16.

EXAMPLE 120

21.7 g (0.01 mol) of the compound obtained according to Example 1(b) were reacted with 2.25 g (0.01 mol) of 3,5-dimethyl-4-methylmercapto-phenyl N-methyl-carbamate analogously to Example 71. Subsequent stirring time: 12 hours at 95° C.

23.7 g of a brown-grey solid were obtained. This active compound modified according to the invention was readily soluble in water and/or lower alcohols and had the ideal formula

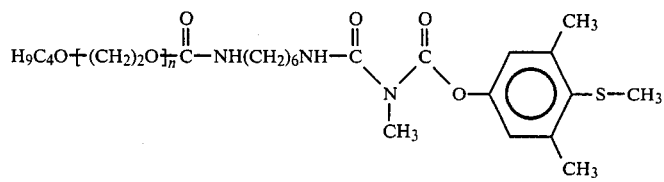

in which n=43.

EXAMPLE 121

11.7 g (0.01 mol) of the compound obtained according to Example 2(b) were reacted with 2.9 g (0.01 mol) of 3-(d-tetralyl)-4-hydroxycoumarin analogously to Example 74. Subsequent stirring time: 3 hours at 90° C.

14.1 g of a dark pink-yellow solid were obtained. This active compound modified according to the invention was readily soluble in water and/or lower alcohols and had the ideal formula

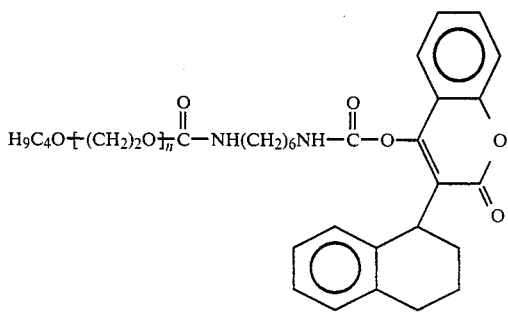

in which n=21.

EXAMPLE 122

21.7 g (0.01 mol) of the compound obtained according to Example 3(b) were reacted with 3.1 g (0.01 mol) of 3-(1'-phenyl-2'-acetylethyl)-4-hydroxycoumarin analogously to Example 76. Subsequent stirring time: 3 hours at 105° C.

24.3 g of a red-brown solid were obtained. This active compound modified according to the invention was very readily soluble in water and/or lower alcohols and had the ideal formula

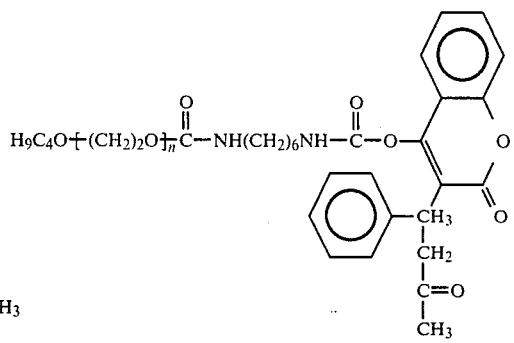

in which n=43.

EXAMPLE 123

21.7 g (0.01 mol) of the compound obtained according to Example 1(b) were reacted with 1.3 g (0.01 mol) of isonicotinic acid hydrazide analogously to Example 80. Subsequent stirring time: 3 hours at 90° C.

22.7 g of a grey-white solid were obtained. This active compound modified according to the invention was readily soluble in water and/or lower alcohols and had the ideal formula

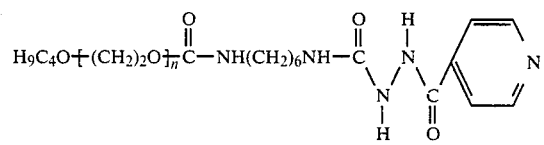

in which n=43.

EXAMPLE 124

11.7 g (0.01 mol) of the compound obtained according to Example 2(b) were reacted with 2.6 g (0.01 mol) of 2-sulphanilamidothiazole analogously to Example 85. Subsequent stirring time: 30 minutes at 70° C.

13.0 g of a grey-yellow solid were obtained. This active compound modified according to the invention was readily soluble in water and/or lower alcohols and had the ideal formula

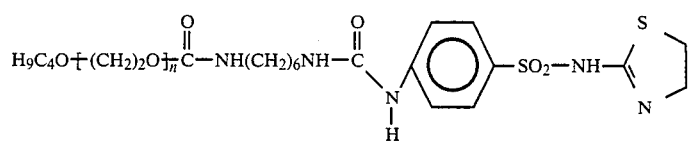

in which n=21.

EXAMPLE 125

11.7 g (0.01 mol) of the compound obtained according to Example 2(b) were reacted with 2.2 g (0.01 mol) of D(−)-threo-1-(p-nitrophenyl)-2-dichloroacetamido- 1,3-propanediol analogously to Example 89. Subsequent stirring time: 7 hours at 85° C.

13.5 g of a red-golden colored solid of wax-like consistency were obtained. This active compound modified according to the invention was readily soluble in water and/or lower alcohols and had the ideal formula

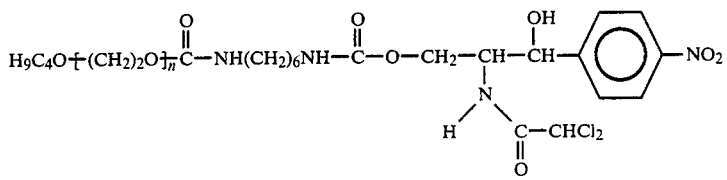

in which n=21.

EXAMPLE 126

11.7 g (0.01 mol) of the compound obtained according to Example 2(b) were reacted with 3.9 g (0.01 mol) of N-(4-chloro-3-sulphamoylbenzenesulphonyl)-N-methyl-2-aminomethyl-2-methyltetrahydrofuran analogously to Example 92. Subsequent stirring time: 16 hours at 100° C.

15.5 g of a brown-yellow solid of wax-like consistency were obtained. This active compound modified according to the invention was readily soluble in water and/or lower alcohols and had the ideal formula

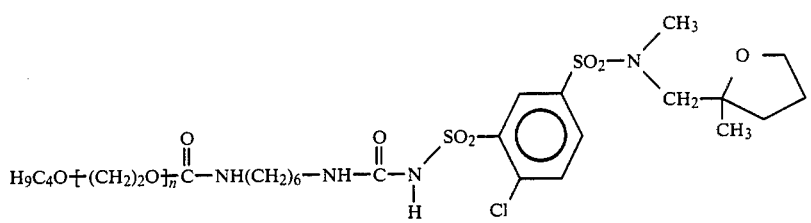

in which n=21.

EXAMPLE 127

11.7 g (0.01 mol) of the compound obtained according to Example 2(b) were reacted with 3.6 g (0.01 mol) of D(+)-6-(5-amino-5-carboxyvaleramido)-3,3-dimethyl-7-oxo-4-thia-1-azabicyclo-[3,2,0]-heptane-2-carboxylic acid analogously to Example 94. Subsequent stirring time: 90 minutes at 60° C.

14.8 g of a grey-yellow solid were obtained. This active compound modified according to the invention was readily soluble in water and/or lower alcohols and had the ideal formula

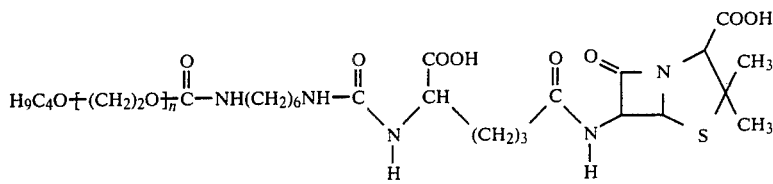

in which n=21.

EXAMPLE 128

21.7 g (0.01 mol) of the compound obtained according to Example 1(b) were reacted with 3.2 g (0.01 mol) of 1-phenyl-5-sulphanilamidopyrazole analogously to Example 95. Subsequent stirring time: 30 minutes at 80° C.

24.5 g of a grey-pink colored product were obtained. This active compound modified according to the invention was readily soluble in water and/or lower alcohols and had the ideal formula

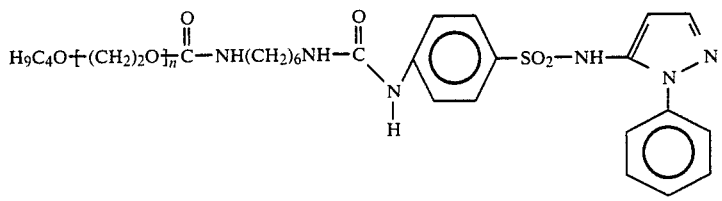

in which n=43.

EXAMPLE 129

9.5 g (0.01 mol) of the compound obtained according to Example 3(b) were reacted with 3.8 g (0.01 mol) of D(−)-7-(α-amino-phenylacetamido)-3-methyl-8-oxo-5-thia-1-azabicyclo[4,2,0]-oct-2-ene-2-carboxylic acid analogously to Example 96. Subsequent stirring time: 4 hours at 50° C.

12.9 g of a pale yellow, viscous product were obtained. This active compound modified according to the invention was readily soluble in water and/or lower alcohols and had the ideal formula

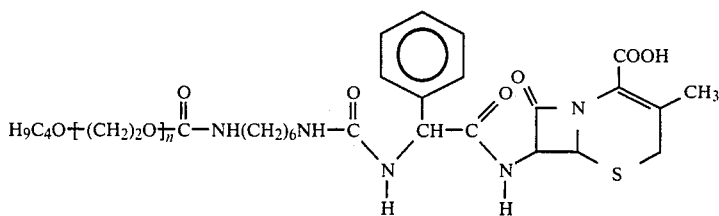

in which n=16.

EXAMPLE 130

21.7 g (0.01 mol) of the compound obtained according to Example 1(b) were reacted with 3.5 g (0.01 mol) of D(−)-6-(α-aminophenylacetamido)-3,3-dimethyl-7-oxo-4-thia-1-azabicyclo-[3,2,0]-heptane-2-carboxylic acid analogously to Example 97. Subsequent stirring time: 35 minutes at 60° C.

24.7 g of a pale yellow solid were obtained. This active compound modified according to the invention was readily soluble in water and/or lower alcohols and had the ideal formula

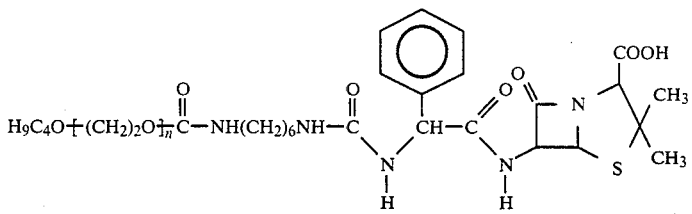

in which n=43.

EXAMPLE 131

11.7 g (0.01 mol) of the compound obtained according to Example 2(b) were reacted with 5.3 g (0.01 mol) of 9-acetyl-7,8,9,10-tetrahydro-6,7,9,11-tetrahydroxy-4-methoxy-5,12-naphthacenequinone-7-(3-amino-5-methyl-2,3-dideoxy-α-lyxopyranoside) analogously to Example 99. Subsequent stirring time: 105 minutes at 55° C.

16.6 g of a pale grey-yellow solid were obtained. This active compound modified according to the invention was readily soluble in water and/or lower alcohols and had the ideal formula

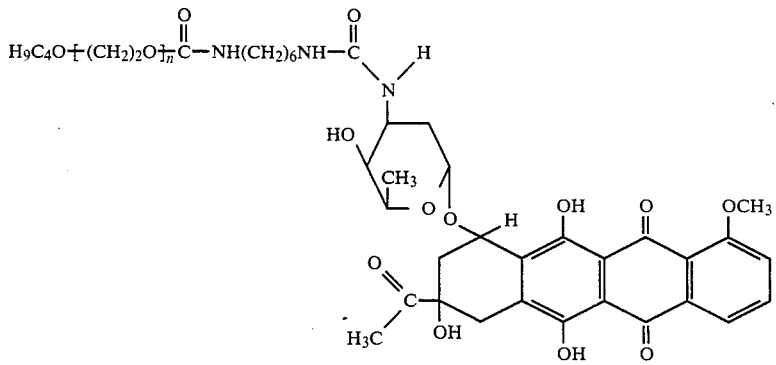

in which n=21.

EXAMPLE 132

11.7 g (0.01 mol) of the compound obtained according to Example 2(b) were reacted with 1.7 g (0.01 mol) of 6-aminopurine-8-thiol analogously to Example 100. Subsequent stirring time: 15 minutes at 45° C.

13.0 g of a red-yellow, wax-like solid were obtained. This active compound modified according to the invention was readily soluble in water and/or lower alcohols and had the ideal formula

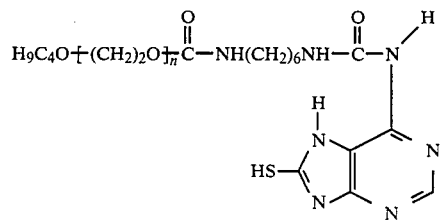

in which n=21.

EXAMPLE 133

11.7 g (0.01 mol) of the compound obtained according to Example 2(b) were reacted with 2.2 g (0.01 mol) of 6-amino-3,3-dimethyl-7-oxo-4-thia-1-azabicyclo-[3,2,0]-heptanecarboxylic acid analogously to Example 101. Subsequent stirring time: 20 minutes at 60° C.

13.6 g of a whitish-yellow, wax-like solid were obtained. This active compound modified according to the invention was readily soluble in water and/or lower alcohols and had the ideal formula

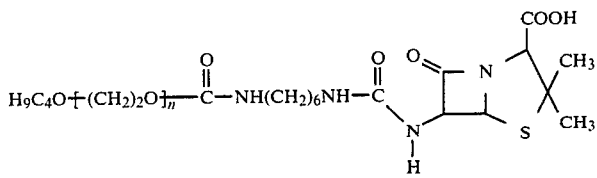

in which n=21.

EXAMPLE 134

21.7 g (0.01 mol) of the compound obtained according to Example 1(b) were reacted with 2.3 g (0.01 mol) of 4-amino-benzenesulphothiocarbamide analogously to Example 103. Subsequent stirring time: 15 minutes at 85° C.

23.6 g of a reddish-yellow solid were obtained. This active compound modified according to the invention was readily soluble in water and/or lower alcohols and had the ideal formula

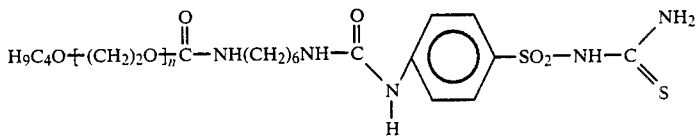

in which n=43.

EXAMPLE 135

21.7 g (0.01 mol) of the compound obtained according to Example 1(b) were reacted with 3.5 g (0.01 mol) of 2,6-dimethyl-3,5-dimethoxycarbonyl-4-o-nitrophenyl-1,4-dihydropyridine analogously to Example 104. Subsequent stirring time: 45 minutes at 75° C.

24.7 g of a grey-yellow solid were obtained. This active compound modified according to the invention was readily soluble in water and/or lower alcohols and had the ideal formula

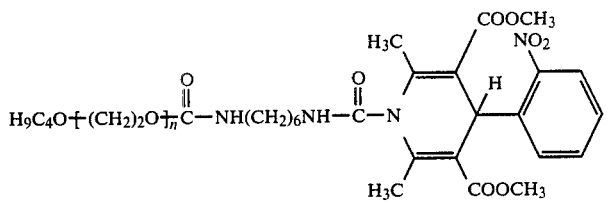

in which n=43.

EXAMPLE 136

11.7 g (0.01 mol) of the compound obtained according to Example 2(b) were reacted with 3.5 g (0.01 mol) of 2,6-dimethyl-3,5-dimethoxycarbonyl-4-o-nitrophenyl-1,4-dihydropyridine analogously to Example 105. Subsequent stirring time: 55 minutes at 75° C.

14.8 g of a dark yellow, wax-like solid were obtained. This active compound modified according to the invention was readily soluble in water and lower alcohols and had the ideal formula

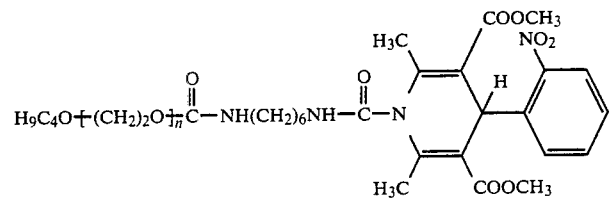

in which n=21.

EXAMPLE 137

9.5 g (0.01 mol) of the compound obtained according to Example 3(b) were reacted with 3.5 g (0.01 mol) of 2,6-dimethyl-3,5-dimethoxycarbonyl-4-o-nitrophenyl-1,4-dihydropyridine analogously to Example 106. Subsequent stirring time: 80 minutes at 65° C.

12.6 g of a reddish grey-yellow viscous product were obtained. This active compound modified according to the invention was readily soluble in water and methanol as well as ethanol and had the ideal formula

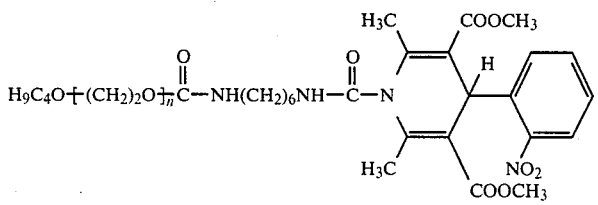

in which n=16.

EXAMPLE 138

11.7 g (0.01 mol) of the compound obtained according to Example 2(b) were reacted with 2.8 g (0.01 mol) of 2-sulphanilamido-5-methoxypyrimidine analogously to Example 107. Subsequent stirring time: 20 minutes at 65° C.

13.1 g of a grey-yellow solid of wax-like consistency were obtained. This active compound modified according to the invention was readily soluble in water and/or lower alcohols and had the ideal formula

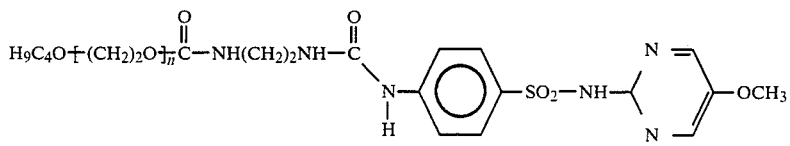

in which N=21.

EXAMPLE 139

21.4 g (0.01 mol) of the product obtained according to Example 1(c) were dissolved in 100 ml of absolute toluene. A solution of 2.14 g (0.01 mol) of 4-amino-6-tert.-butyl-3-(methylthio)-1,2,4-triazin-5(4H)-one in 50 ml of toluene was added dropwise to this solution at 105° C. in the course of half an hour. Methanol formed was distilled off over a Claisen attachment during and after the dropwise addition until the reaction had ended. The temperature of the bath was then increased to 120° C. and the solvent was distilled off. Subsequent stirring time: 8 hours at a bath temperature of 120° C.

The mixture was then allowed to cool to 80° C. and was evacuated to 25 mbars, whereby the last traces of methanol and solvent were removed. The mixture was cooled to room temperature, flushing with nitrogen was carried out and 23.3 g of a brown-red solid were obtained. This new active compound modified according to the invention was readily soluble in water and/or lower alcohols and had the ideal formula

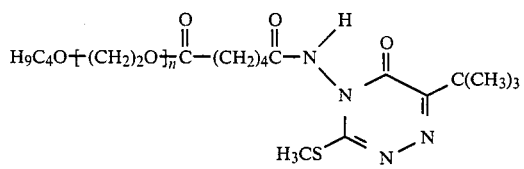

in which n=43.

EXAMPLE 140

9.2 g (0.01 mol) of the product obtained according to Example 3(c) were dissolved in 50 ml of absolute toluene. A solution of 3.4 g (0.01 mol) of 1,3-di-p-chlorophenyl-(1H,2H,3H,4H,5H,6H)-1,3,5-triazine-2,4-dione in 50 ml of absolute acetone was added dropwise to this solution at 80° C. in the course of 1 hour, while stirring vigorously, most of the acetone being distilled off over a Claisen attachment during the dropwise addition. The temperature of the bath was increased to 120° C. and methanol formed during the reaction was distilled off over a Vigreux column. Subsequent stirring time: 24 hours at a bath temperature of 120° C.

The solvent was then distilled off and thereafter the residue was freed from residues of methanol and solvent in vacuo (25 mbars).

12.2 g of a dark brown, viscous product were obtained. This active compound modified according to the invention was readily soluble in water and methanol as well as ethanol and had the ideal formula

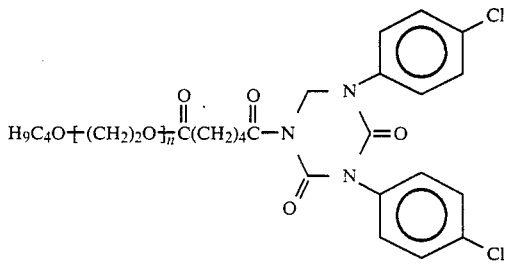

in which n=16.

EXAMPLE 141

21.4 g (0.01 mol) of the product obtained according to Example 1(c) were reacted with 2.14 g (0.01 mol) of 4-amino-6-tert.-butyl-3-(methylthio)-1,2,4-triazin-5(4H)-one analogously to Example 139. However, when the dropwise addition had ended, 0.1 g of sodium metal was also added. Further treatment of the mixture was as indicated in Example 139. Subsequent stirring time: 2 hours at a bath temperature of 120° C.

After cooling, 50 ml of methanol and 0.5 ml of concentrated hydrochloric acid were added to the residue. The insoluble material was filtered off and the methanol was then removed from the filtrate by concentrating the filtrate in vacuo (200 mbars).

23.2 g of a brown-yellow solid were obtained. This active compound modified according to the invention was readily soluble in water and/or lower alcohols and had the ideal formula

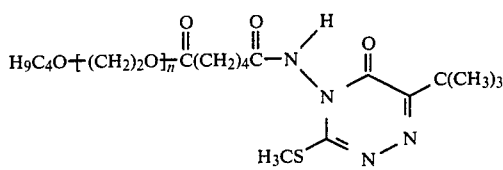

in which n=43.

EXAMPLE 142

9.2 g (0.01 mol) of the product obtained according to Example 3(c) were reacted with 3.4 g (0.01 mol) of 1,3-di-p-chlorophenyl-(1H,2H,3H,4H,5H,6H)-1,3,5-triazin-2,4-dione analogously to Example 140. However, after the acetone had been distilled off and before the temperature was increased to 130° C., 0.1 g of sodium metal were also added. Further treatment of the mixture was as indicated in Example 140. Subsequent stirring time: 40 hours at a bath temperature of 120° C.

After cooling, 50 ml of methanol and 0.5 ml of concentrated hydrochloric acid were added to the residue. The insoluble material was filtered off tne the methanol was removed from the filtrate by concentrating the filtrate in vacuo.

12.1 g of a red-brown, viscous product were obtained. This active compound modified according to the invention was readily soluble in water and/or methanol as well as ethanol and had the ideal formula

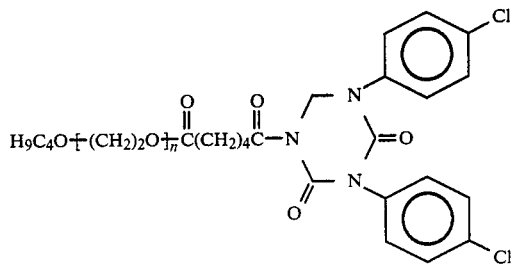

in which n=16.

EXAMPLE 143

21.4 g (0.01 mol) of the compound obtained according to Example 1(c) were reacted with 2.0 g (0.01 mol) of 3-methyl -4-amino-6-phenyl-1,2,4-triazin-5(4H)-one analogously to Example 141. Subsequent stirring time: 2 hours at 120° C.

22./8 g of a dark yellow solid were obtained. This active compound modified according to the inmention was readily soluble in water and/or lower alcohols and had the ideal formula

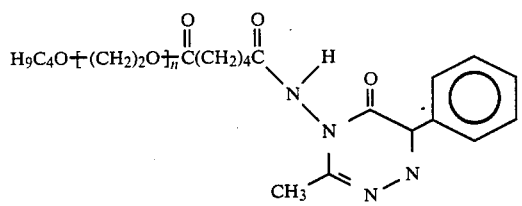

in which n=43.

EXAMPLE 144

9.2 g (0.01 mol) of the compound obtained according to Example 3(c) were reacted with 3.1 g (0.01 mol) of N-(o,o'-difluorobenzoyl)-N'-(p-chlorophenyl)-urea analogously to Example 142. Subsequent stirring time: 326 hours at 120° C.

11.6 g of a dark brown, viscous product were obtained. This active compound modified according to the invention was readily soluble in water and/or lower alcohols and had the ideal formula

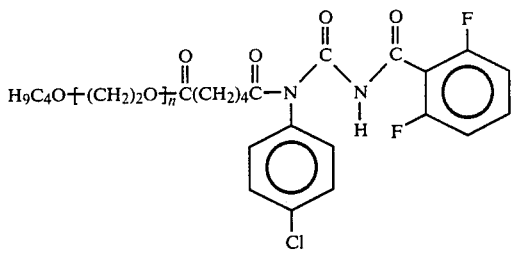

in which n=16.

EXAMPLE 145

21.4 g (0.01 mol) of the compound obtained according to Example 1(c) were reacted with 3.7 g (0.01 mol) of 3-(3,4-dichlorophenyl)-6-(2,6-difluorophenyl)-1-oxa-3,5-diazine-(3H,5H)-2,4-dione analogously to Example 141. Subsequent stirring time: 22 hours at 190° C.

24.6 g of a dark, greenish-brown solid were obtained. This active compound modified according to the invention was readily soluble in water and/or lower alcohols and had the ideal formula

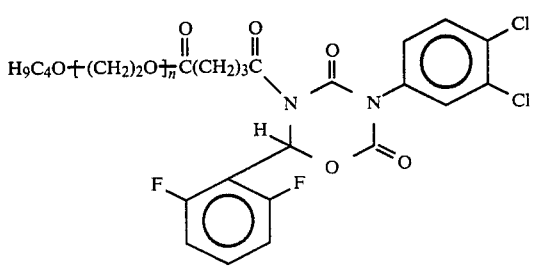

in which n=43.

EXAMPLE 146

21.4 g (0.01 mol) of the compound obtained according to Example 1(c) were reacted with 2.1 g (0.01 mol) of 2-iso-propoxyphenyl N-methylcarbamate analogously to Example 141. Subsequent stirring time: 48 hours at 120° C.

23.1 g of a dark brown solid were obtained. This active compound modified according to the invention was readily soluble in water and/or lower alcohols and had the ideal formula

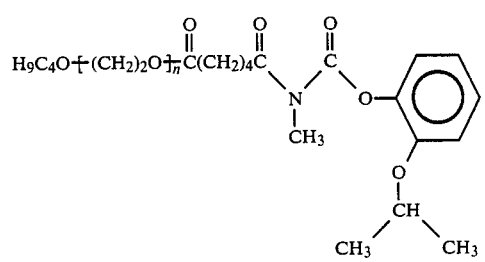

in which n=43.

EXAMPLE 147

9.2 g (0.01 mol) of the compound obtained according to Example 3(c) were reacted with 2.6 g (0.01 mol) of 2-sulphanilamidothiazole analogously to Example 142. Subsequent stirring time: 2 hours at 120° C.

11.3 g of a golden yellow, viscous product were obtained. This active compound modified according to the invention was readily soluble in water and methanol as well as ethanol and had the idel formula

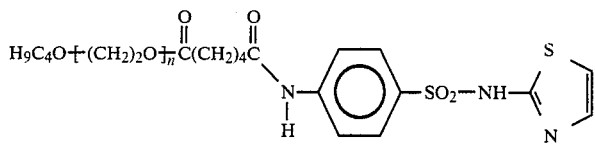

in which n=16.

EXAMPLE 148

21.4 g (0.01 mol) of the compound obtained according to Example 1(c) were reacted with 2.2 g (0.01 mol) of D(−)-threo-1-(p-nitrophenyl)-2-dichloroacetamido-1,3-propanediol analogusly to Example 139. Subsequent stirring time: 17 hours at 105° C.

23.0 g of a red-golden colored, wax-like solid were obtained. This active compound modified according to the invention was readily soluble in water and/or lower alcohols and had the ideal formula

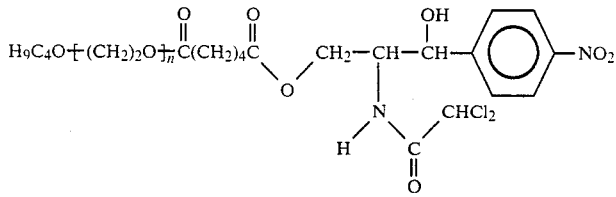

in which n=43.

EXAMPLE 149

9.4 g (0.01 mol) of the compound obtained according to Example 3(c) were reacted with 2.3 g (0.01 mol) of 4-amino-benzenesulphothiocarbamide analogously to Example 142. Subsequent stirring time: 45 minutes at 120° C.

11.1 g of a red-yellow, viscous product were obtained. This active compound modified according to the invention was readily soluble in water and methanol as well as ethanol and had the ideal formula

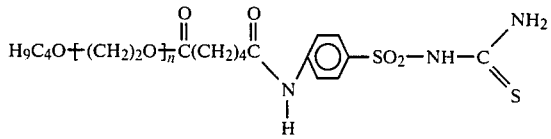

in which n=16.

EXAMPLE 150

21.4 g (0.01 mol) of the compound obtained according to Example 1(c) were reacted with 2.8 g (0.01 mol) of 2-sulphanilamido-5-methoxypyrimidine analogously to Example 141. Subsequent stirring time: 155 minutes at 120° C.

23.5 g of a dark yellow solid were obtained. This active compound modified according to the invention was readily soluble in water and/or lower alcohols and had the ideal formula

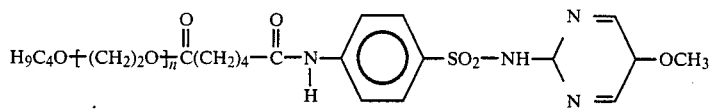

in which n=43.

EXAMPLE 151

864 g (0.4 mol) of an ethylene oxide polyether started from n-butanol and having an average molecular weight of 2,160 (average number of ethylene oxide units n=42) with a terminal p-isocyanatophenylurethane group (CO content: 1.94% by weight) were initially introduced at 40° C. 85.2 g (0.4 mol) of 4-amino-6-tert.-butyl-3-(methylthio)-1,2,4-triazin-5(4H)-one, which had been dissolved in 300 ml of absolute toluene, were added dropwise in the course of 2 hours, while stirring rapidly. When the dropwise addition had ended, the mixture was stirred for 10 minutes at 40° C. Thereafter NCO was no longer detectable in the reaction mixture by IR spectroscopy. The solvent was then distilled off in vacuo.

946 g of a light yellow solid were obtained. This active compound modified according to the invention was very readily soluble in water and/or lower alcohols and had the ideal formula

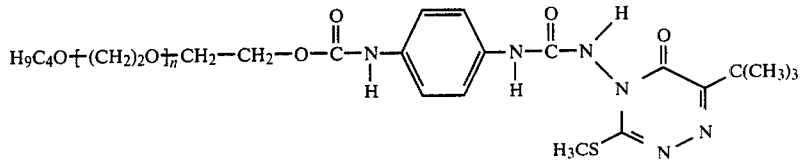

in which n=42.

EXAMPLE 152

33.6 g (0.2 mol) of hexamethylene disocyanate were stirred under dry nitrogen with 69.0 g (0.2 mol) of O-ethyl-o-(2-iso-propoxy-carbonyl)-phenyl-N-isopropylamidothiophosphate at 170° C. till the NCO content had fallen to the calculated value of 8.2% by weight. The mixture was cooled and 92.4 g of a yellow product of the ideal formula

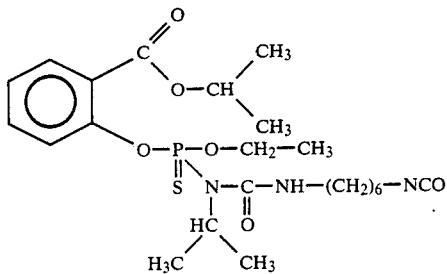

were obtained. To this product was added 140.4 g (0.18 mol) of dry monofunctinal ethylene oxide polyether started from n-butanol and having an average molecular weight of 784, (average number of ethylene oxide units n=16 and an OH number of 71.6) and the mass was stirred at 140° C. for 60 minutes. After this time the NCO content had fallen to 0% by weight. 223.5 g of a yellow paste were obtained of the ideal formula

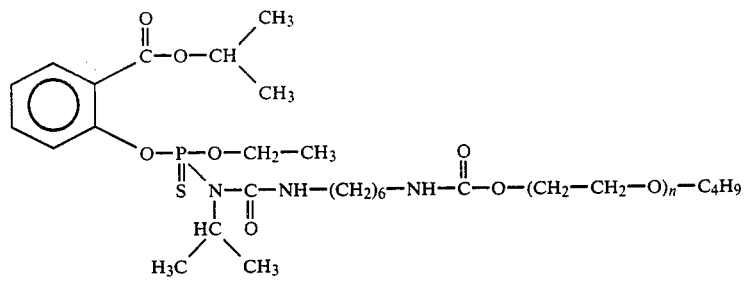

in which n=16

It will be appreciated that the instant specification and examples are set forth by way of illustration and not limitation, and that various modifications and changes may be made without departing from the spirit and scope of the present invention.

What we claim is:

1. A process for improving the solubility in water and or lower aliphatic alcohols of a sparingly soluble biologically active compound which has at least one hydrogen atom active in Zerewitinoff reactions comprising reacting (a) a hydrophilic polyether that contains one OH, NH or NH2 group and having a water absorption capcity of at least 15%, relative to the weight of the polyether with (b) an organic compound having at least two groups that are reactive towards hydrogen atoms that are active in Zerewitinoff reactions, in the ratio (m−1):m for the number of the OH, NH or NH2 equivalents of the polyether (a) to the number of the equivalents of groups in the organic compound (b) that are reactive towards hydrogen atoms that are active in Zerewitinoff reactions and reacting that product with an equivalent amount of (c) the biologically active compound.

2. A process for improving the solubility in water and or lower aliphatic alcohols of a sparingly soluble biologically active compound which has at least one hydrogen atom active in Zerewitinoff reactions, comprising reacting (b) an organic compound having m groups that are reactive towards hydrogen atoms that are active in Zerewitinoff reactions, m being at least two, with an approximately equimolar amount of (c) the biologically active compound and reacting that product with (a) a hydrophilic polyether containing one OH, NH or NH2 group and having a water absorption capacity of at least 15%, relative to the weight of the polyether the ratio of (a) to product of (b)+(c) being m:(m−1).

3. A process for improving the solubility in water and or lower aliphatic alcohols of a sparingly soluble biologically active compound which has at least one hydrogen atom active in Zerewitinoff reactions, comprising reacting (a) a hydrophilic ether that contains one OH, NH or NH2 group and having a water absorption capacity of at least 15% relative to the weight of the polyether with (b) an organic compound having at least two groups that are reactive towards hydrogen atoms that are active in Zerewitinoff reactions, in the ratio (m−1):m for the number of the OH, NH or NH2 equivalents of the polyether (a) to the number of the equivalents of groups in the organic compound (b) that are reactive towards hydrogen atoms that are active in Zerewitinoff reactions and with (c) the biologically active compound, the ratio of (b):(a):(c) being 1:m:(m−1) wherein m is the number of reactive hydrogen atoms in (b).

4. A compound produced by the process of claims 1, 2, or 3 of the formula

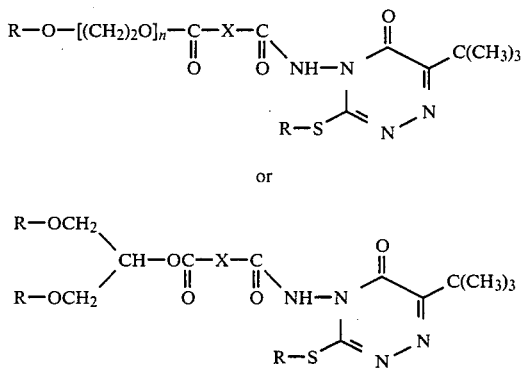

or

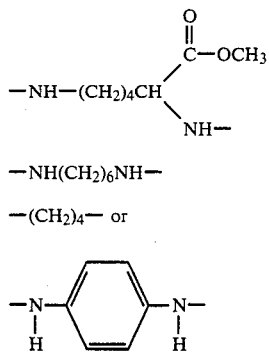

in which
R is alkyl of 1 to 4 carbon atoms,
n=1 to 90, and
X is $$-NH-(CH_2)_4CH\begin{matrix}C-OCH_3\\ \| \\ O\\ NH-\end{matrix}$$

$-NH(CH_2)_6NH-$ $-(CH_2)_4-$ or

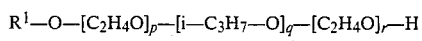

5. A compound produced by the process of claim 1, 2 or 3, wherein the polyether is of the formula $$R^1-O-[C_2H_4O]_p-[i-C_3H_7-O]_q-[C_2H_4O]_r-H$$

in which
$R^1$ is the radical of a starter molecule whih has an alkoxylatable hydrogen atom, and
p, q and r each is an integer from 0–400, provided that at least one of p and r is greater than 2, and provided that the ratio (p+r):q is not less than 0.5.

6. A compound produced by the process of claim 2 or 3, wherein the polyether is of the formula $$R^1-O-(CH_2CH_2O)_n-CH_2CH_2OH$$

in which
$R^1$ is the radical of a monoalcohol with 1–6 C atoms, and
n is an integer from 1 to 160.

7. A compound according to claim 6, wherein $R^1$ is n-butyl and n is from 1 to 90.

8. A compound produced by the process of claim 1, 2, or 3, wherein the organic compounds is of the formula

in which
$R^2$ is a divalent aliphatic hydrocarbon radical with 2–40 C atoms, which is optionally substituted by halogen, cyano, nitro, optionally substituted alkyl- or arylmercapto, alkoxycarbonyl, alkoxysulphonyl alkoxyphosphoryl, halogenocarbonyl, amidoyl, alkoxyphosphoryl, a 'aryl' denoting phenyl or naphthyl, either of which is optionally substituted by $C_{1-6}$-alkyl, halogen, cyano, nitro, optionally substituted alkoxy, alkylmercapto, arylmercapto or halogenoalkyl; or $R^2$ is a cycloaliphatic hydrocarbon radical with 4–15 C atoms or an aromatic hydrocarbon radical with 6–15 C atoms, which in either case is optionally monosubstituted or polysubstituted by alkyl with 1 to 20 C atoms (which is optionally monosubstituted or polysubstituted by halogen, cyano, nitro, optionally substituted alkylmercapto, aryl (aryl denoting phenyl or naphthyl, either of which is optionally monosubstituted or polysubstituted by alkyl with 1–6 C atoms, halogen, cyano, optionally substituted alkoxy, alkylmercapto, arylmercapto or halogenoalkyl), alkoxycarbonyl, alkoxysulphonyl alkoxyphosphoryl, halogenocarbonyl, amidoyl, alkoxy, aryloxy, arylmercapto, aryloxycarbonyl, aryloxysulphonyl or aryloxyphosphoryl, aryl in each case having the meaning indicated above), by cycloalkyl with 5–20 C atoms (which is optionally monosubstituted or polysubstituted by alkyl with 1–6 C atoms, halogen, cyano, nitro, optionally substituted alkylmercapto, alkoxycarbonyl, alkoxysulphonyl, alkoxyphosphoryl, halogenocarbonyl, amidoyl, alkoxy, aryl aryloxy, arylmercapto, aryloxycarbonyl, aryloxysulphonyl or aryloxyphosphoryl, aryl in each case having the meaning indicated above), by phenyl or naphthyl (either of which is optionally monosubstituted or polysubstituted by alkyl, halogen, CN, optionally substituted alkoxy, alkylmercapto, alkoxycarbonyl, alkoxysulphonyl, alkoxyphosphoryl, halogenocarbonyl, amidoyl, aryloxy, arylmercapto, aryloxycarbonyl aryloxysulphon-1 or aryloxyphosphoryl, aryl having the meaning indicated above), or by halogen, cyano, nitro, alkoxycarbonyl, alkoxysulphonyl, alkoxyphosphoryl, halogenocarbonyl, amidoyl, optionally substituted alkoxy, alkylmercapto, aryloxy, arylmercapto, aryloxycarbonyl, aryloxysulphonyl or arylphosphoryl, aryl in each case having the meaning indicated above, or $R^2$ represents hydrocarbon radicals with 7–15 C atoms, one of the radicals X or Y being bonded to the aliphatic part and the other radical X or Y being bonded to the aromatic part, or both radicals X and Y being bonded to the aliphatic part, and/or the aromatic part optionally being substituted by any of the substituents indicated above in the case of the aromatic hydrocarbons, and X and Y each independently is halogenocarbonyl alkoxycarbonyl, carboxyl, carboxylic acid anhydride sulphonic acid, sulphonic acid halide, sulphonic aeid alkyl ester, phosphoric acid, phosphoric acid halide, phosphoric acid alkyl ester, isothiocyanate, isocyanate or isocyanide dihalide.

9. A compound produced by the process of claim 1, 2 or 3, wherein the organic compound is of the formula

in which
$R^2$ is a divalent aliphatic hydrocarbon radical with 2–18 C atoms, which is optionally substituted by halogen, cyano nitro, alkoxycarbonyl, alkoxysulphonyl, alkoxyphosphoryl alkoxy, aryloxy, aryloycarbonyl, aryloxysulphonyl or aryloxyphosphoryl, "aryl" denoting phenyl or naphthyl, either of which is optionally substituted by $C_{1-6}$-alkyl halogen, cyano, nitro, optionally substituted alkoxy, alkylmercapto, aryloxy, arylmercapto or halogenoalkyl; or $R^2$ is a divalent cycloaliphatic hydrocarbon radical with 5–10 C atoms or an aromatic hydrocarbon radical with 6–13 C atoms, which is in either case optionally monosubstituted or polysubstituted by alkyl with 1–4 C atoms, which is optionally substituted as indicated in claim 6, and/or by halogen, cyano, nitro, alkoxycarbonyl, alkoxysulphonyl, alkoxyphosphoryl, alkoxy, aryloxy, aryloxycarbonyl, aryloxysulphonyl or aryloxyphosphoryl, aryl having the meaning indicated; or $R^2$ represents a divalent araliphatic radical with 8–13 C atoms, which is in each case optionally monosubstituted or polysubstituted by halogen, cyano, nitro, alkoxycarbonyl, alkoxysulphonyl, alkoxyphosphoryl, optionally substituted alkoxy, alkylmercapto, aryloxy, arylmercapto, aryloxycarbonyl, aryloxysulphonyl or aryloxyphosphoryl, aryl having the meaning indicated above, and in addition to the aforesaid substituents, the aromatic part of the araliphatic radical can be substituted by $C_{1-4}$-alkyl or ahlogenoalkyl, and X and Y each independently is halogenocarbonyl, alkoxycarbonyl, carboxyl, carboxylic acid anhydride or isocyanate.

10. A compound produced by the process of claim 1, 2 or 3, wherein the organic compound is of the formula $$X-R^2-Y$$

in which $R^2$ is a divalent aliphatic hydrocarbon radical with 2–8 C atoms, which is optionally monosubstituted or polysubstituted by $C_{1-4}$-alkoxycarbonyl, and X and Y each is isocyanate.

11. A compound according to claim 9, wherein the polyether is of the formula $$R^1-O-(CH_2CH_2O)_n-CH_2CH_2OH$$

in which $R^1$ is the radical of a monoalcohol with 1–6 C atoms, and n is an integer from 1 to 160.

12. A compound according to claim 11, wherein $R^1$ is n-butyl, n is from 1 to 90, $R^2$ is a divalent aliphatic hydrocarbon radical with 2–8 C atoms, which is optionally monosubstituted or polysubstituted by $C_{1-4}$-alkoxycarbonyl and X and Y each is isocyanate.

* * * * *

UNITED STATES PATENT AND TRADEMARK OFFICE
CERTIFICATE OF CORRECTION

PATENT NO. : 4,684,728

DATED : August 4, 1987

INVENTOR(S) : Edgar Möhring, et al.

It is certified that error appears in the above-identified patent and that said Letters Patent is hereby corrected as shown below:

| | |
|---|---|
| Title Page, under "U.S. Patent Documents", line 4 | Delete "Mohring" and substitute --Möhring-- |
| Col. 2, line 1 | Delete "leat" and substitute --least-- |
| Col. 3, lines 25 and 26; Col. 20, line 28 | Delete "p" and "r" and substitute --$\underline{p}$-- and --$\underline{r}$-- |
| Col. 3, line 25; line 28 | Delete "q" and substitute --$\underline{q}$-- |
| Col. 3, line 59 | Correct spelling of --butylaniline-- |
| Col. 4, line 3 | Delete "n" and substitute --$\underline{n}$--, et seq. |
| Col. 5, line 2 | Delete "amidoyl, optionally substituted alkoxy, alkylmercapto," |
| Col. 7, line 44 | Delete "1,3,4" and substitute --1,3,5-- |
| Col. 7, line 49 | After "benzothiadiazine" delete "." |
| Col. 8, line 4 | Delete "dimethoxyloxazole" and substitute --dimethyloxazole-- |
| Col. 8, line 6 | Delete "4,5" and substitute --4,6-- |
| Col. 9, line 28 | Delete "60" and substitute --$\alpha$-- |
| Col. 9, line 32 | Delete "acetamide" and substitute --acetamido-- |
| Col. 9, lines 36-37 | Correct spelling of --cinnamoyloxyphenyl-- |
| Col. 10, line 31 | Delete "4²" and substitute --$\Delta^2$-- |

UNITED STATES PATENT AND TRADEMARK OFFICE
CERTIFICATE OF CORRECTION

PATENT NO. : 4,684,728
DATED : August 4, 1987
INVENTOR(S) : Edgar Möhring, et al.

It is certified that error appears in the above-identified patent and that said Letters Patent is hereby corrected as shown below:

| | |
|---|---|
| Col. 11, line 5 | Correct spelling of --penicillanic-- |
| Col. 14, line 66 | Delete "chloride" and substitute --chlorides-- |
| Col. 15, line 15 | After "time" insert --the-- |
| Col. 15, line 20 | Correct spelling of --monochlorocarbonic-- |
| Col. 15, line 33 | Correct spelling of --hydrochloride-- |
| Col. 18, line 68 | Delete "the" before "process" |
| Col. 20, line 34 | Delete "n-nitrophenyl" and substitute --p-nitrophenyl-- |
| Col. 20, line 42 | Delete "had" and substitute --has-- |
| Col. 21, line 9, | Delete "samples" and substitute --examples-- |
| Col. 21, line 44 | After "of" delete "the" and substitute --a-- |
| Col. 21, line 58 | Insert --were obtained-- |
| Col. 24, line 33 | End of formula delete "-C" and substitute -- -CH -- 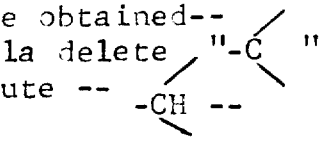 |
| Col. 25, line 27 | Delete "Example 9" and substitute --Example 8-- |
| Col. 32, line 10 | Insert -- ∥O -- at end of formula as follows: |

UNITED STATES PATENT AND TRADEMARK OFFICE
CERTIFICATE OF CORRECTION

PATENT NO. : 4,684,728

DATED : August 4, 1987

INVENTOR(S) : Edgar Möhring, et al.

It is certified that error appears in the above-identified patent and that said Letters Patent is hereby corrected as shown below:

| | |
|---|---|
| Col. 32, line 21 | Delete "4 H" and substitute --4H-- |
| Col. 33, line 6 | Delete "mole" and substitute --mol-- |
| Col. 33, line 64 | Delete "8.9" and substitute --8.7-- |
| Col. 34, line 33; Col. 35, line 63 | Insert --$\overset{\mid}{\underset{H}{\phantom{x}}}$-- at end of formula as follows: 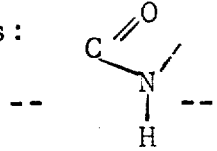 |
| Col. 34, line 42 | Correct spelling of --methylthio-- |
| Col. 35, line 51 | After "3" insert -- - -- |
| Col. 60, line 53 | After "2-" insert --methyl-2- -- |
| Col. 68, line 24 | Delete "idea" and substitute --ideal-- |
| Col. 71, line 64 | After "6" insert -- - -- |
| Col. 74, line 52 | Delete "difluorobenzcyl" and substitute --difluorobenzoyl-- |
| Col. 76, line 53 | Delete "-isoproxyphenol" and substitute -- -isopropoxyphenyl-- |
| Col. 87, line 23 | Delete "tne" and substitute --the-- |
| Col. 88, line 3 | Delete "326 hours" and substitute --36 hours-- |

UNITED STATES PATENT AND TRADEMARK OFFICE
CERTIFICATE OF CORRECTION

PATENT NO. : 4,684,728

DATED : August 4, 1987

INVENTOR(S) : Edgar Möhring, et al.

It is certified that error appears in the above-identified patent and that said Letters Patent is hereby corrected as shown below:

| | |
|---|---|
| Col. 88, line 27 | Delete "190°C" and substitute --120°C-- |
| Col. 89, line 11 | Delete "idel" and substitute --ideal-- |
| Col. 90, line 56 | Insert additional space after "C." |
| Col. 91, line 67; Col. 92, lines 29, 38 | After "polyether" insert --,-- |
| Col. 92, line 15 | After "reactions" insert --,-- |
| Col. 92, lines 18 and 31 | After "and" insert --/-- |
| Col. 92, line 26 | After "compound" insert --,-- |
| Col. 92, line 37 | After "15%" insert --,-- |
| Col. 93, line 4 | After "claim" insert --1,-- |
| Col. 93, line 59 | Delete "compounds" and substitute --compound-- |
| Col. 94, line 1 | Delete "a 'aryl'" and substitute -- "aryl" -- |
| Col. 94, line 45 | Before "hydrocarbon" insert --araliphatic-- |

UNITED STATES PATENT AND TRADEMARK OFFICE
CERTIFICATE OF CORRECTION

PATENT NO. : 4,684,728

DATED : August 4, 1987

INVENTOR(S) : Edgar Möhring, et al.

It is certified that error appears in the above-identified patent and that said Letters Patent is hereby corrected as shown below:

Col. 96, lines 26-27          After "alkoxycarbonyl" insert --,--

Signed and Sealed this

Eleventh Day of April, 1989

Attest:

DONALD J. QUIGG

Attesting Officer          Commissioner of Patents and Trademarks